(12) United States Patent
Tomura et al.

(10) Patent No.: US 8,207,330 B2
(45) Date of Patent: Jun. 26, 2012

(54) TWO-PHOTON ABSORPTION MATERIAL AND APPLICATION THEREOF

(75) Inventors: Tatsuya Tomura, Tokyo (JP); Tsutomu Sato, Yokohama (JP); Takeshi Miki, Tokyo (JP); Mikiko Takada, Kawasaki (JP); Hisamitsu Kamezaki, Yokosuka (JP)

(73) Assignee: Ricoh Company, Ltd., Tokyo (JP)

( * ) Notice: Subject to any disclaimer, the term of this patent is extended or adjusted under 35 U.S.C. 154(b) by 439 days.

(21) Appl. No.: 12/423,475

(22) Filed: Apr. 14, 2009

(65) Prior Publication Data
US 2010/0056775 A1 Mar. 4, 2010

(30) Foreign Application Priority Data

Aug. 26, 2008 (JP) .................................. 2008-217276
Jan. 20, 2009 (JP) .................................. 2009-009719

(51) Int. Cl.
*C07B 47/00* (2006.01)
*C07D 487/22* (2006.01)
(52) U.S. Cl. ..................................................... 540/145
(58) Field of Classification Search .................... 540/145
See application file for complete search history.

(56) References Cited

U.S. PATENT DOCUMENTS

| 2003/0030718 | A1 | 2/2003 | Maeda |
| 2003/0236400 | A1* | 12/2003 | Zhang et al. ................... 540/145 |
| 2008/0092310 | A1 | 4/2008 | Miki et al. |

FOREIGN PATENT DOCUMENTS

| JP | 6-28672 | 2/1994 |
| JP | 6-118306 | 4/1994 |
| JP | 8-320422 | 12/1996 |
| JP | 9-230246 | 9/1997 |
| JP | 10-142507 | 5/1998 |
| JP | 2000-512061 | 9/2000 |
| JP | 2001-508221 | 6/2001 |
| JP | 2001-522119 | 11/2001 |
| JP | 2001-524245 | 11/2001 |
| JP | 2004-168690 | 6/2004 |
| JP | 2004-534849 | 11/2004 |
| JP | 2004-339435 | 12/2004 |
| JP | 2005-500394 | 1/2005 |
| JP | 2005-82507 | 3/2005 |
| JP | 2005-100606 | 4/2005 |
| JP | 2005-134873 | 5/2005 |
| JP | 2005-165212 | 6/2005 |
| JP | 2005-517769 | 6/2005 |
| JP | 2005-213434 | 8/2005 |
| JP | 2005-263738 | 9/2005 |
| JP | 2006-178399 | 7/2006 |
| JP | 2006-209059 | 8/2006 |
| JP | 2006-251351 | 9/2006 |
| JP | 2007-91684 | 4/2007 |
| JP | 2007-119443 | 5/2007 |
| JP | 2007-178585 | 7/2007 |
| JP | 2007-241168 | 9/2007 |
| JP | 2007-241170 | 9/2007 |
| JP | 2007-246422 | 9/2007 |
| JP | 2007-246463 | 9/2007 |
| JP | 2007-246790 | 9/2007 |
| JP | 2008-69294 | 3/2008 |
| JP | 2008-163184 | 7/2008 |
| JP | 2008-214303 | 9/2008 |
| WO | WO 98/25268 | 6/1998 |
| WO | WO 98/31018 | 7/1998 |
| WO | WO 98/53448 | 11/1998 |
| WO | WO 99/23650 | 5/1999 |

(Continued)

OTHER PUBLICATIONS

Drobizhev et al., J. Phys. Chem. vol. 110, (2006) pp. 9802-9814.*

(Continued)

*Primary Examiner* — Paul V. Ward
(74) *Attorney, Agent, or Firm* — Oblon, Spivak, McClelland, Maier & Neustadt, L.L.P.

(57) ABSTRACT

A two-photon absorption material represented by the following General Formula (I):

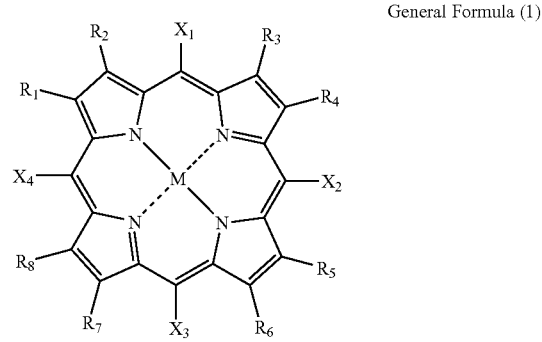

General Formula (1)

where $R_1$ to $R_8$ each represent hydrogen, halogen, a carboxyl group, a carboxylic acid ester group, a substituted or unsubstituted aryl group, or a substituted or unsubstituted alkyl group; one to three of $X_1$ to $X_4$ each represent a substituted or unsubstituted amino group, a substituted or unsubstituted aminophenyl group, a substituted or unsubstituted dialkylaminophenyl group, a substituted or unsubstituted N,N-diphenyl-aminophenyl group, a substituted or unsubstituted indolyl group, or a substituted or unsubstituted azulenyl group, and the other represents or the others each represent hydrogen, halogen, a carboxyl group, a carboxylic acid ester group, a substituted or unsubstituted aryl group, a substituted or unsubstituted pyridinyl group, a substituted or unsubstituted alkyl group or a perhalogenoalkyl group; and M represents two hydrogen atoms or a divalent, trivalent or tetravalent metal atom which may have oxygen or halogen.

16 Claims, 10 Drawing Sheets

FOREIGN PATENT DOCUMENTS

| | | | |
|---|---|---|---|
| WO | WO 03/006450 | | 1/2003 |
| WO | WO 03/017846 | * | 3/2003 |
| WO | WO 03/070689 | | 8/2003 |
| WO | WO 2008/119950 A1 | | 10/2008 |

OTHER PUBLICATIONS

M khail Drobizhev, et al., "Strong Two-Photon Absorption in New Asymmetrically Substituted Porphyrins: Interference between Charge-Transfer and Intermediate-Resonance Pathways", J. Phys. Chem. B, American Chemical Society, vol. 110, XP-002535703, May 2, 2006, pp. 9802-9814.

Guangyao Y. Gao, et al., "General and Efficient Synthesis of Arylamino- and Alkylamino-Substituted Diphenylporphyrins and Tetraphenylporphyrins via Palladium-Catalyzed Multiple Amination Reactions", J. Org. Chem., JOC Article, vol. 68, XP-002535704, Jul. 9, 2003, pp. 6215-6221.

Francis D'Souza, et al., "Multi-Triphenylamine-Substituted Porphyrin-Fullerene Conjugates as Charge Stabilizing "Antenna-Reaction Center" Mimics", J. Phys. Chem. A, American Chemical Society, vol. 111, XP-002535705, Jul. 4, 2007, pp. 8552-8560.

John N. Clifford, et al., "Molecular control of recombination dynamics in dye sensitised nanocrystalline $TiO_2$, films", Chem. Comm., The Royal Society of Chemistry, XP-002535706, May 9, 2002 pp. 1260-1261.

Kazuya Ogawa, et al., "Strong Two-Photon Absorption of Self-Assembled Butadiyne-Linked Bisporphyrin", J. Am. Chem. Soc. (JACS) Communications, XP-002599402, vol. 125, 2003, pp. 13356-13357.

Search Report issued Sep. 22, 2010, in European Patent Application No. 10170353.6-1211.

Science, vol. 281, www.sciencemag.org., Sep. 11, 1998, pp. 1653-1656.

Ju-Won Seo, et al., "Octupolar Trisporphyrin Conjugates Exhibiting Strong Two-Photon Absorption", Tetrahedron, Elsevier, Science Direct, XP022477052, vol. 64, No. 12, Jan. 19, 2008, pp. 2733-2739.

Shitao Fu, et al., "Synthesis, Structures and Optical Power Limiting of Some Transition Metal and Lanthanide Monoporphyrinate Complexes Containing Electron-Rich Diphenylamino Substituents", European Journal of Inorganic Chemistry, XP002548671 Nov. 14, 2007, pp. 2004-2013.

* cited by examiner

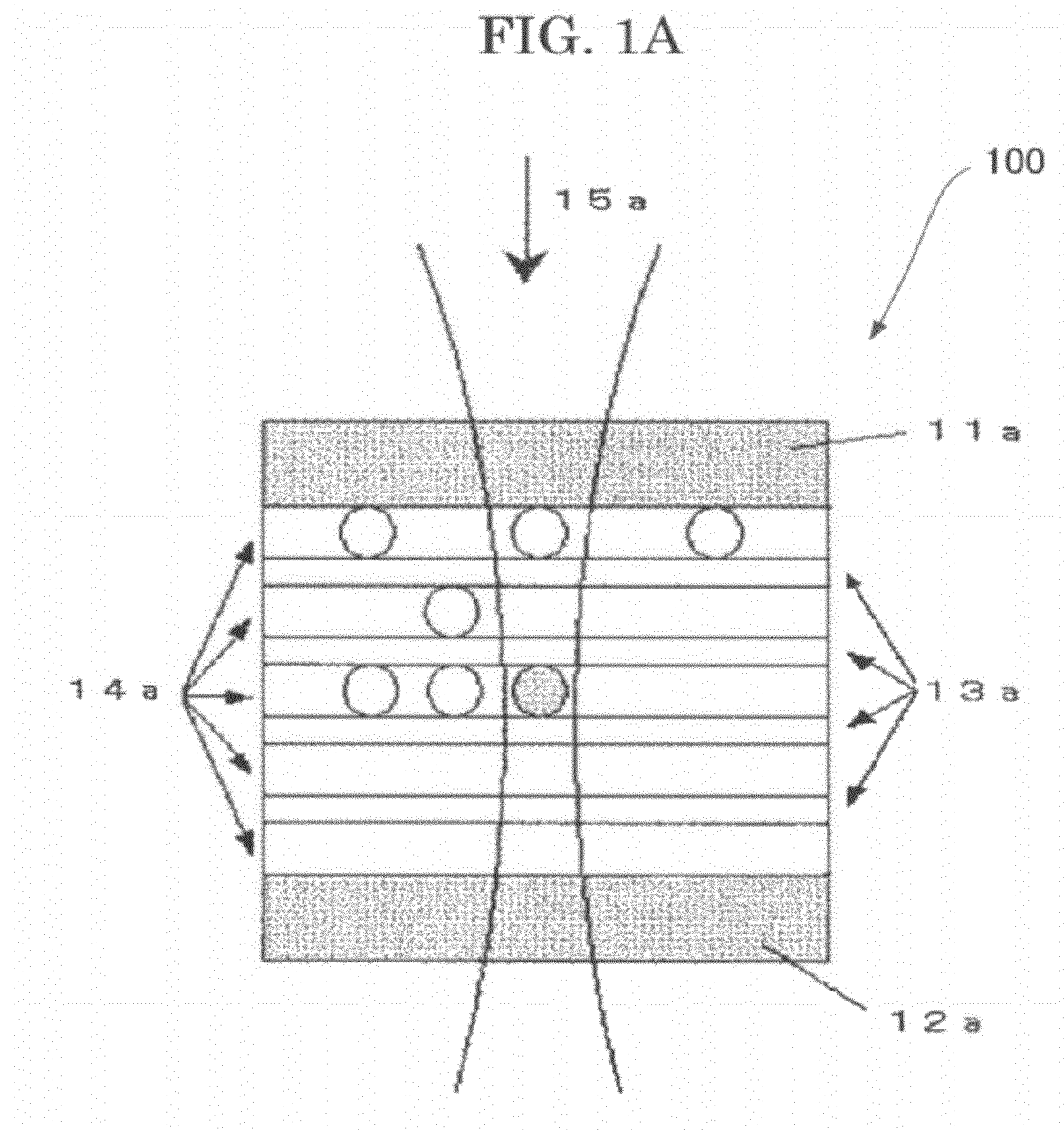

TWO-PHOTON ABSORPTION MATERIAL AND APPLICATION THEREOF

BACKGROUND OF THE INVENTION

1. Field of the Invention

The present invention relates to a two-photon absorption material, in particular, a two-photon absorption material having a large two-photon absorption cross-sectional area, which is applied to, for example, materials for various organic electronics devices such as three-dimensional memory materials, light restricting materials, photocurable resins for optical molding (curable materials), materials for photo-chemotherapy, and fluorescent dyes for two-photon fluorescence microscopy.

2. Description of the Related Art

Two-photon absorption is a type of three-dimensional nonlinear optical effects. This is a phenomenon in which one molecule absorbs two photons simultaneously to transit from the ground state to the excited state. The two-photon absorption has been known for a long period of time. In recent years, studies on materials having two-photon absorptivity have been advanced, since Jean-Luc Bredas et al. unraveled the relationship between the molecular structure and the mechanism (Science, 281, 1653 (1998)).

Two-photon absorption materials can be excited with light having a wavelength falling within a non-resonant region. The actual excited state thereof is at an energy level about twice as much as that of photons used for the excitation. The efficiency of transition caused by two-photon absorption is proportional to the square of the intensity of an optical field applied (square-law characteristics of two-photon absorption).

Thus, when a laser beam is applied, two-photon absorption occurs only at a position where the electric field intensity is high; i.e., the center of a laser spot, and two-photon absorption does not occur at all at a position where the electric field intensity is low; i.e., the peripheral portion.

Hitherto, Japanese Patent Application Laid-Open (JP-A) Nos. 2005-213434, 2005-82507, 2004-168690, 2007-178585 and other patent literatures disclose two-photon absorption materials.

Also, JP-A Nos. 2005-500394, 2004-168690, 2004-339435, 2005-263738, 2006-178399, 2006-209059, 2006-251351, 2007-91684, 2007-119443 and other patent literatures disclose porphyrin derivatives serving as two-photon absorption materials.

In a three-dimensional space, two-photon absorption occurs only at an area where the electric field intensity is high; i.e., a focal point of the laser beam condensed by a lens. Meanwhile, two-photon absorption does not occur at all at an area where the electric field intensity is low; i.e., an area other than the focal point.

Compared with one-photon linear absorption in which excitation occurs at all the positions proportionally to the intensity of the optical field applied, for two-photon absorption, excitation occurs only at a pinpoint region in the space by virtue of the square-law characteristics. Thus, spatial resolution is remarkably improved.

By utilizing the above characteristics, three-dimensional memory has been studied which records bit data by changing spectrum, refractive index, or polarized light at predetermined positions of recording media. And, attempts have been made to apply two-photon absorption materials to three-dimensional multi-layer memory.

For example, networks (e.g., the Internet) and high-vision TVs become popular rapidly, and high-definition television (HDTV) broadcast is starting soon. Thus, demand for mass-storage recording media has been increasing, in order to record image information of 50 GB or higher (preferably 100 GB or higher) inexpensively and simply in consumer use.

Hitherto, JP-A Nos. 2005-100606, 2005-517769, 2004-534849 and other patent literatures disclose such three-dimensional memory media (materials).

Also, JP-A No. 08-320422 and other patent literatures disclose a light restricting device (material).

Also, JP-A No. 2005-134873 and other patent literatures disclose optical molding.

Also, JP-A Nos. 09-230246, 10-142507, 2005-165212 and other patent literatures disclose (fluorescent) microscopes utilizing two-photon absorption.

Separately, the present inventors have previously developed and proposed techniques relating to two-photon absorption materials (see JP-A Nos. 2007-246463, 2007-246790, 2008-69294, 2008-214303, 2007-241170, 2007-246422 and 2008-163184).

Furthermore, optical recording media have been demanded for business applications (e.g., computer and broadcast backups) in order to inexpensively record mass information of about 1 TB or higher at high speed. Under such circumstances, the capacity of conventional two-dimensional optical recording media (e.g., CDs and DVDs) is at most about 25 GB on physical principles, even if a recording/reproducing wavelength is shortened. This capacity is not enough considering use thereof in future.

In view of this, three-dimensional optical recording media have been prominently expected as ultimate high-density, high-capacity recording media.

In the three-dimensional optical recording media, information can be recorded in the form of several tens or several hundreds of superposed layers in a three-dimensional (thickness) direction to achieve ultra high-density, ultra high-capacity recording which is several ten or several hundred times higher than conventional two-dimensional recording media.

To provide three-dimensional optical recording media, information needs to be written with access to a predetermined area in a three-dimensional (thickness) direction. To achieve this, a two-photon absorption material or holography (interference) may be employed.

In three-dimensional optical recording media using a two-photon absorption material, so-called bit recording, which can record information several ten or several hundred times as much as conventional recording, can be attained based on the aforementioned physical principles, thereby achieving higher-density recording. Thus, the three-dimensional optical recording media are ultimately high-density, high-capacity optical recording media.

Regarding three-dimensional optical recording media using a two-photon absorption material, there have been proposed a method of reading information through fluorescence by using a fluorescent compound during recording/reproducing (JP-A Nos. 2001-524245 and 2000-512061); a method of reading information through absorption or fluorescence by using a photochromic compound (JP-A Nos. 2001-522119 and 2001-508221); and other methods. However, any of these literatures do not specifically but abstractly describe two-photon absorption compounds such as two-photon absorption compounds with extremely small two-photon absorption efficiency.

Moreover, the photochromic compounds described in these patent literatures are reversible materials and thus, there are problems in nondestructive readout, long-term archivability of recorded information, an S/N ratio concerning reproduction, and the like. Thus, the photochromic compounds are not suitably used for optical recording media in practical use. In terms of, among others, nondestructive readout and long-term archivability of recorded information, irreversible materials are preferably used since reproduction can be performed based on change in reflectivity (indices of refraction and absorptivity) or luminescence intensity. However, none of them specifically discloses two-photon absorption materials having such properties.

Also, JP-A Nos. 06-28672 and 06-118306 disclose three-dimensional recording apparatuses, reproducing apparatuses therefor, readout methods therefor, and the like, but do not describe a method using a two-photon absorption, three-dimensional optical recording material.

Two-photon absorption can be applied to various applications requiring very high spatial resolution. But, two-photon absorption compounds available at the present time have low two-photon absorptivity and thus, requires expensive, extremely high-power laser as a light source used for causing two-photon absorption. Therefore, in order to employ a small-scale, inexpensive laser to realize practical uses based on two-photon absorption, it is required to develop highly sensitive two-photon absorption materials.

In the above-described porphyrin-based two-photon absorption materials, two-photon absorptivity is imparted to them, for example, as follows. Specifically, a specific color-developing moiety is introduced into a porphyrin skeleton (JP-A No. 2005-500394), porphyrin skeletons are linked to each other (JP-A No. 2004-168690), porphyrin skeletons are condensated with each other (JP-A Nos. 2005-263738 and 2006-178399), and a porphyrin skeleton is elongated (JP-A No. 2006-209059). However, any of the formed skeletons have complicated structures, making it difficult to produce compounds of interest on an industrial scale. In addition, they exhibit an insufficiently large two-photon absorption cross-sectional area.

Also, the present inventors have found that a specific aza-porphyrin, in which a carbon atom at a meso position of the porphyrin skeleton has been substituted with a nitrogen atom, exhibits excellent two-photon absorptivity, and have previously disclosed it in JP-A No. 2008-163184. But, this compound does not exhibit a sufficiently large two-photon absorption cross-sectional area.

As described above, conventional compounds have a small two-photon absorption cross-sectional area, which indicates two-photon absorptivity per molecule. Particularly when a femtosecond pulse laser is used, most of the compounds exhibit a two-photon absorption cross-sectional area smaller than 200 GM (1 GM=$1 \times 10^{-50}$ $cm^4 \cdot s \cdot molecule^{-1} \cdot photon^{-1}$). Thus, industrial applications of these compounds have not been made yet.

As described above, two-photon absorption can be applied to various applications requiring very high spatial resolution. But, two-photon absorption compounds available at the present time have low two-photon absorptivity and thus, requires expensive, extremely high-power laser as a light source used for causing two-photon absorption.

Therefore, in order to employ a small-scale, inexpensive laser to realize practical uses based on two-photon absorption, it is required to develop highly sensitive two-photon absorption materials.

But, two-photon absorption compounds available at the present time have low two-photon absorptivity. Thus, it is necessary to use an extremely high-power laser as a light source, and it takes a long period of time for information recording.

In particular, in use thereof in three-dimensional optical recording media, in order to achieve a high transfer rate, it is necessary to design a two-photon absorption, three-dimensional optical recording material which attains recording with high sensitivity based on the differences in optical characteristics (e.g., luminescence and reflection) through two-photon absorption. To achieve this, a material containing a two-photon absorption compound and a recording component is effective, wherein the two-photon absorption compound can be at an excited state by absorbing two photons with high efficiency, and the recording component can efficiently form the differences of optical characteristics (e.g., luminescence and reflection) of the two-photon absorption optical recording material by a method utilizing the excited state of the two-photon absorption compound. But, such a material has been hardly disclosed, and demand has arisen for the material and the method for designing it.

BRIEF SUMMARY OF THE INVENTION

An object of the present invention is to provide a two-photon absorption optical recording material and a recording medium formed therefrom which contain at least a two-photon absorption compound having a large two-photon absorption cross-sectional area, the recording medium achieving recording/reproducing characterized in that information recording is performed in a non-rewritable mode by utilizing two-photon absorption of the two-photon absorption compound, and then information reproducing is performed by irradiating the medium with light to detect the differences in the intensities of luminescence, reflection, etc.

Specifically, the present invention provides the following:

(1) an organic material which changes in spectrum, refractive index and/or polarization state with high sensitivity and which effectively absorbs two photons; i.e., an organic material having a large two-photon absorption cross-sectional area;

(2) a material which has a porphyrin skeleton exhibiting good two-photon absorptivity and which can be relatively readily produced on an industrial scale;

(3) a two-photon absorption material which can provide a recording medium in which information recording is performed in a non-rewritable mode by utilizing two-photon absorption of the two-photon absorption material (compound), and then information reproducing is performed by irradiating the medium with light to detect the differences in optical characteristics between recorded portions and unrecorded portions.

(4) an optical molding material containing, as part of a photocurable resin, the two-photon absorption material of the present invention, and an optical molding apparatus requiring reduced light irradiation energy;

(5) a material for a light restricting device, the material containing, as part of the light restricting device, the two-photon absorption material of the present invention, and a light restricting device/apparatus requiring reduced light irradiation energy; and (6) a two-photon excitation fluorescent material in which an analyte selectively carrying the two-photon absorption material of the present invention is analyzed through two-photon excitation fluorescence detection, and a two-photon excitation fluorescence detection apparatus requiring reduced light irradiation energy.

Means for solving the above problems pertinent in the art are as follows.

<1> A two-photon absorption material represented by the following General Formula (I):

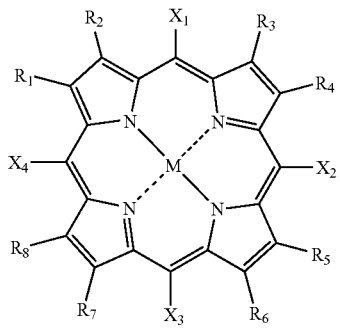

General Formula (1)

where $R_1$ to $R_8$ each represent a hydrogen atom, a halogen atom, a carboxyl group, a carboxylic acid ester group, a substituted or unsubstituted aryl group, or a substituted or unsubstituted alkyl group; one to three of $X_1$ to $X_4$ each represent a substituted or unsubstituted amino group, a substituted or unsubstituted aminophenyl group, a substituted or unsubstituted dialkylaminophenyl group, a substituted or unsubstituted N,N-diphenyl-aminophenyl group, a substituted or unsubstituted indolyl group, or a substituted or unsubstituted azulenyl group, and the other represents or the others each represent a hydrogen atom, a halogen atom, a carboxyl group, a carboxylic acid ester group, a substituted or unsubstituted aryl group, a substituted or unsubstituted pyridinyl group, a substituted or unsubstituted alkyl group or a perhalogenoalkyl group; and M represents two hydrogen atoms or a divalent, trivalent or tetravalent metal atom which may have an oxygen atom or a halogen atom.

<2> The two-photon absorption material according to <1> above, wherein one to three of $X_1$ to $X_4$ each represent a substituted or unsubstituted amino group, a substituted or unsubstituted aminophenyl group, a substituted or unsubstituted dialkylaminophenyl group, a substituted or unsubstituted N,N-diphenyl-aminophenyl group, a substituted or unsubstituted indolyl group, or a substituted or unsubstituted azulenyl group, and the other is or the others each are a trifluoromethyl group.

<3> The two-photon absorption material according to any one of <1> and <2> above, wherein one to three of $X_1$ to $X_4$ each are a substituted or unsubstituted N,N-diphenyl-aminophenyl group.

<4> The two-photon absorption material according to <1> above, wherein at least one of $X_1$ and $X_3$ is a phenyl group having, as a substitutent, an alkyl group, an alkoxy group, a trifluoromethyl group, a nitro group, a cyano group or a carboxylic acid ester group, or a substituted or unsubstituted pyridinyl group, with the proviso that when only one of $X_1$ and $X_3$ is the phenyl group or the pyridinyl group, the other is a hydrogen atom or a halogen atom; and at least one of $X_2$ and $X_4$ is a substituent represented by (a) or (b) given below, with the proviso that when only one of $X_2$ and $X_4$ is the substitutent, the other is a hydrogen atom or a halogen atom,

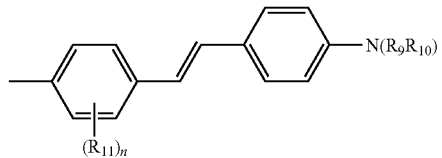

(a)

where $R_{11}$ represents an alkyl group or an alkoxy group, $R_9$ and $R_{10}$ each represent a hydrogen atom, an alkyl group or a substituted or unsubstituted phenyl group, and n is an integer of 1 or 2,

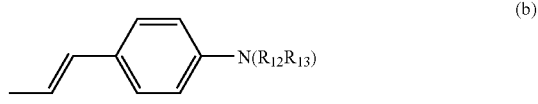

(b)

where $R_{12}$ and $R_{13}$ each represent a hydrogen atom, an alkyl group or a substituted or unsubstituted phenyl group.

<5> A two-photon absorption material represented by the following General Formula (A):

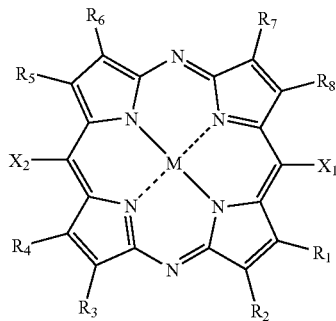

(A)

where $R_1$ to $R_8$ each represent a hydrogen atom, a halogen atom, a nitro group, a cyano group, a hydroxyl group, a carboxyl group, a substituted or unsubstituted alkyl group, a substituted or unsubstituted alkoxy group, a substituted or unsubstituted aryl group, a substituted or unsubstituted amino group, or a substituted or unsubstituted acyl group; $X_1$ and $X_2$ each represent a hydrogen atom, a halogen atom, a nitro group, a cyano group, a hydroxyl group, a carboxyl group, a substituted or unsubstituted alkyl group, a substituted or unsubstituted alkoxy group, a substituted or unsubstituted aryl group, a substituted or unsubstituted amino group, a substituted or unsubstituted acyl group, or a group having a substituted or unsubstituted triphenylamine structure which group may be bonded via a linking group to a diazaporphyrin skeleton; at least one of $X_1$ and $X_2$ represents the group having a substituted or unsubstituted triphenylamine structure which group may be bonded via a linking group to a diazaporphyrin skeleton; and M represents two hydrogen atoms, a divalent, trivalent or tetravalent metal atom which may have an oxygen atom or a halogen atom, or a metal atom which may have at least one selected from groups $(OR_9)a$, $(OSiR_{10}R_{11}R_{12})b$, $(OPOR_{13}R_{14})c$ and $(OCOR_{15})d$ (in the groups, $R_9$ to $R_{15}$ each represent a hydrogen atom or a substituted or unsubstituted aliphatic group or aromatic hydrocarbon group, and each of a, b, c and d is an integer of 0 to 2).

<6> The two-photon absorption material according to <5> above, wherein the two-photon absorption material is represented by the following formula (1):

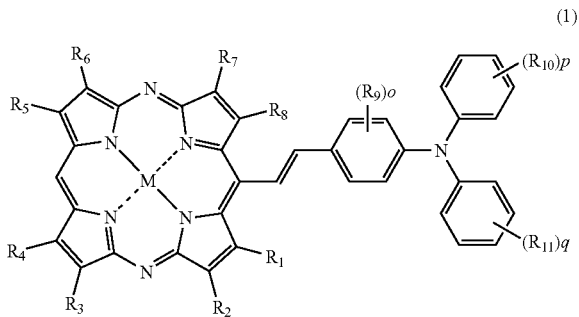

(1)

where $R_1$ to $R_8$ each represent a hydrogen atom, a halogen atom, a nitro group, a cyano group, a hydroxyl group, a carboxyl group, a substituted or unsubstituted alkyl group, a substituted or unsubstituted alkoxy group, a substituted or unsubstituted aryl group, a substituted or unsubstituted amino group, or a substituted or unsubstituted acyl group; $R_9$ to $R_{11}$ each represent a hydrogen atom, a substituted or unsubstituted alkyl group, or a substituted or unsubstituted alkoxy group; o is an integer of 1 to 4; each of p and q is an integer of 1 to 5; and M represents two hydrogen atoms, a divalent, trivalent or tetravalent metal atom which may have an oxygen atom or a halogen atom, or a metal atom which may have at least one selected from groups $(OR_9)a$, $(OSiR_{10}R_{11}R_{12})b$, $(OPOR_{13}R_{14})c$ and $(OCOR_{15})d$ (in the groups, $R_9$ to $R_{15}$ each represent a hydrogen atom or a substituted or unsubstituted aliphatic group or aromatic hydrocarbon group, and each of a, b, c and d is an integer of 0 to 2).

<7> The two-photon absorption material according to <5> above, wherein the two-photon absorption material is represented by the following formula (2):

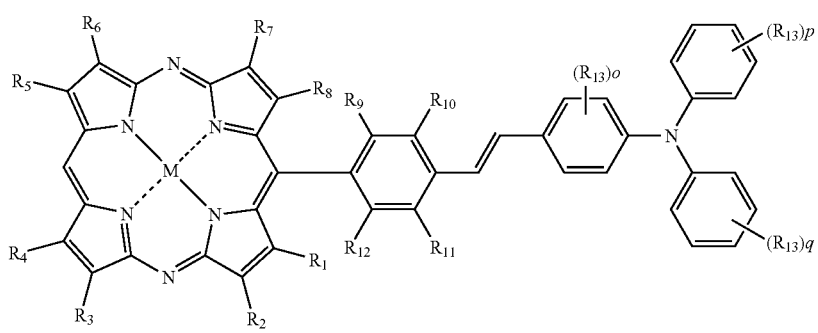

(2)

where $R_1$ to $R_8$ each represent a hydrogen atom, a halogen atom, a nitro group, a cyano group, a hydroxyl group, a carboxyl group, a substituted or unsubstituted alkyl group, a substituted or unsubstituted alkoxy group, a substituted or unsubstituted aryl group, a substituted or unsubstituted amino group, or a substituted or unsubstituted acyl group; $R_9$ to $R_{15}$ each represent a hydrogen atom, a substituted or unsubstituted alkyl group, or a substituted or unsubstituted alkoxy group; o is an integer of 1 to 4; each of p and q is an integer of 1 to 5; and M represents two hydrogen atoms, a divalent, trivalent or tetravalent metal atom which may have an oxygen atom or a halogen atom, or a metal atom which may have at least one selected from groups $(OR_9)a$, $(OSiR_{10}R_{11}R_{12})b$, $(OPOR_{13}R_{14})c$ and $(OCOR_{15})d$ (in the groups, $R_9$ to $R_{15}$ each represent a hydrogen atom or a substituted or unsubstituted aliphatic group or aromatic hydrocarbon group, and each of a, b, c and d is an integer of 0 to 2).

<8> The two-photon absorption material according to <5> above, wherein the two-photon absorption material is represented by the following formula (3):

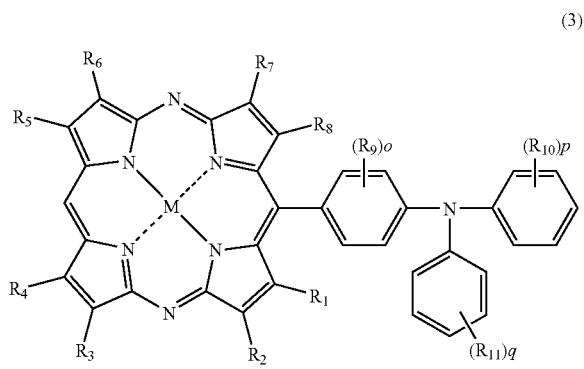

(3)

where $R_1$ to $R_8$ each represent a hydrogen atom, a halogen atom, a nitro group, a cyano group, a hydroxyl group, a carboxyl group, a substituted or unsubstituted alkyl group, a substituted or unsubstituted alkoxy group, a substituted or unsubstituted aryl group, a substituted or unsubstituted amino group, or a substituted or unsubstituted acyl group; $R_9$ to $R_{11}$ each represent a hydrogen atom, a substituted or unsubstituted alkyl group, or a substituted or unsubstituted alkoxy group; o is an integer of 1 to 4; each of p and q is an integer of 1 to 5; and M represents two hydrogen atoms, a divalent, trivalent or tetravalent metal atom which may have an oxygen atom or a halogen atom, or a metal atom which may have at least one selected from groups $(OR_9)a$, $(OSiR_{10}R_{11}R_{12})b$, $(OPOR_{13}R_{14})c$ and $(OCOR_{15})d$ (in the groups, $R_9$ to $R_{15}$ each represent a hydrogen atom or a substituted or unsubstituted aliphatic group or aromatic hydrocarbon group, and each of a, b, c and d is an integer of 0 to 2).

<9> The two-photon absorption material according to <5> above, wherein the two-photon absorption material is represented by the following formula (4):

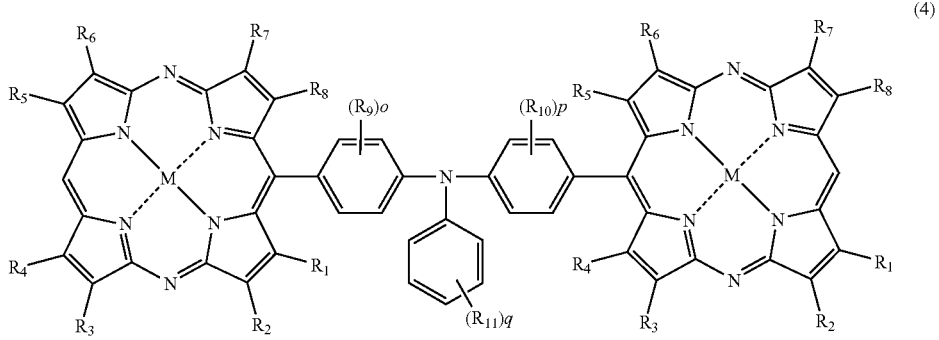
(4)

where $R_1$ to $R_8$ each represent a hydrogen atom, a halogen atom, a nitro group, a cyano group, a hydroxyl group, a carboxyl group, a substituted or unsubstituted alkyl group, a substituted or unsubstituted alkoxy group, a substituted or unsubstituted aryl group, a substituted or unsubstituted amino group, or a substituted or unsubstituted acyl group; $R_9$ to $R_{11}$ each represent a hydrogen atom, a substituted or unsubstituted alkyl group, or a substituted or unsubstituted alkoxy group; o is an integer of 1 to 4; each of p and q is an integer of 1 to 5; and M represents two hydrogen atoms, a divalent, trivalent or tetravalent metal atom which may have an oxygen atom or a halogen atom, or a metal atom which may have at least one selected from groups $(OR_9)a$, $(OSiR_{10}R_{11}R_{12})b$, $(OPOR_{13}R_{14})c$ and $(OCOR_{15})d$ (in the groups, $R_9$ to $R_{15}$ each represent a hydrogen atom or a substituted or unsubstituted aliphatic group or aromatic hydrocarbon group, and each of a, b, c and d is an integer of 0 to 2).

<10> The two-photon absorption material according to <5> above, wherein the two-photon absorption material is represented by the following formula (5):

where $R_1$ to $R_8$ each represent a hydrogen atom, a halogen atom, a nitro group, a cyano group, a hydroxyl group, a carboxyl group, a substituted or unsubstituted alkyl group, a substituted or unsubstituted alkoxy group, a substituted or unsubstituted aryl group, a substituted or unsubstituted amino group, or a substituted or unsubstituted acyl group; $R_9$ to $R_{14}$ each represent a hydrogen atom, a substituted or unsubstituted alkyl group, or a substituted or unsubstituted alkoxy group; each of o and r is an integer of 1 to 4; each of p, q, s and t is an integer of 1 to 5; and M represents two hydrogen atoms, a divalent, trivalent or tetravalent metal atom which may have an oxygen atom or a halogen atom, or a metal atom which may have at least one selected from groups $(OR_9)a$, $(OSiR_{10}R_{11}R_{12})b$, $(OPOR_{13}R_{14})c$ and $(OCOR_{15})d$ (in the groups, $R_9$ to $R_{15}$ each represent a hydrogen atom or a substituted or unsubstituted aliphatic group or aromatic hydrocarbon group, and each of a, b, c and d is an integer of 0 to 2).

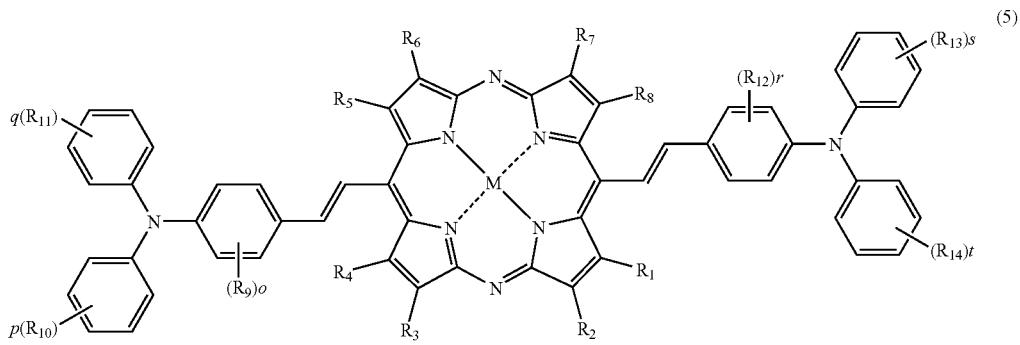
(5)

<11> The two-photon absorption material according to <5> above, wherein the two-photon absorption material is represented by the following formula (6):

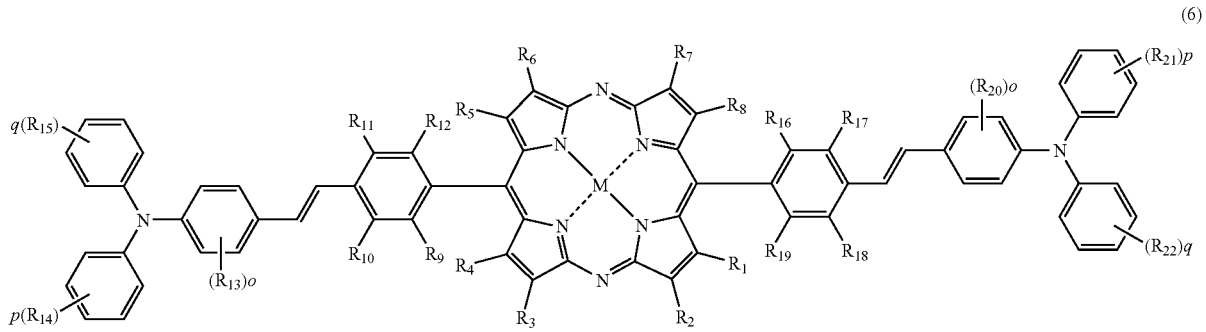

(6)

where $R_1$ to $R_8$ each represent a hydrogen atom, a halogen atom, a nitro group, a cyano group, a hydroxyl group, a carboxyl group, a substituted or unsubstituted alkyl group, a substituted or unsubstituted alkoxy group, a substituted or unsubstituted aryl group, a substituted or unsubstituted amino group, or a substituted or unsubstituted acyl group; $R_9$ to $R_{22}$ each represent a hydrogen atom, a substituted or unsubstituted alkyl group, or a substituted or unsubstituted alkoxy group; each of o and r is an integer of 1 to 4; each of p, q, s and t is an integer of 1 to 5; and M represents two hydrogen atoms, a divalent, trivalent or tetravalent metal atom which may have an oxygen atom or a halogen atom, or a metal atom which may have at least one selected from groups $(OR_9)a$, $(OSiR_{10}R_{11}R_{12})b$, $(OPOR_{13}R_{14})c$ and $(OCOR_{15})d$ (in the groups, $R_9$ to $R_{15}$ each represent a hydrogen atom or a substituted or unsubstituted aliphatic group or aromatic hydrocarbon group, and each of a, b, c and d is an integer of 0 to 2).

<12> The two-photon absorption material according to <5> above, wherein the two-photon absorption material is represented by the following formula (7):

where $R_1$ to $R_8$ each represent a hydrogen atom, a halogen atom, a nitro group, a cyano group, a hydroxyl group, a carboxyl group, a substituted or unsubstituted alkyl group, a substituted or unsubstituted alkoxy group, a substituted or unsubstituted aryl group, a substituted or unsubstituted amino group, or a substituted or unsubstituted acyl group; $R_9$ to $R_{14}$ each represent a hydrogen atom, a substituted or unsubstituted alkyl group, or a substituted or unsubstituted alkoxy group; each of o and r is an integer of 1 to 4; each of p, q, s and t is an integer of 1 to 5; and M represents two hydrogen atoms, a divalent, trivalent or tetravalent metal atom which may have an oxygen atom or a halogen atom, or a metal atom which may have at least one selected from groups $(OR_9)a$, $(OSiR_{10}R_{11}R_{12})b$, $(OPOR_{13}R_{14})c$ or $(OCOR_{15})d$ (in the groups, $R_9$ to $R_{15}$ each represent a hydrogen atom or a substituted or unsubstituted aliphatic group or aromatic hydrocarbon group, and each of a, b, c and d is an integer of 0 to 2).

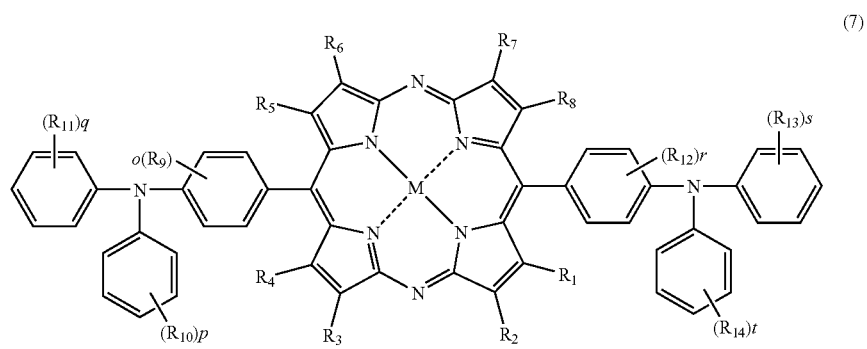

(7)

<13> A two-photon absorption material represented by the following General Formula (III):

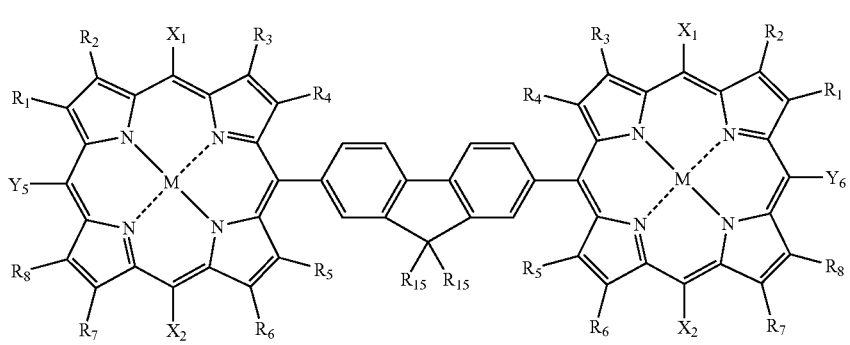

General Formula (III)

where $R_1$ to $R_8$ each represent a hydrogen atom, a halogen atom, a carboxyl group, a carboxylic acid ester group, a substituted or unsubstituted aryl group, or a substituted or unsubstituted alkyl group; $R_{15}$ represents an alkyl group or a hydrogen atom; at least one of $X_1$ and $X_2$ is a phenyl group having, as a substitutent, an alkyl group, an alkoxy group, a trifluoromethyl group, a nitro group, a cyano group or a carboxylic acid ester group, or a substituted or unsubstituted pyridinyl group, with the proviso that when only one of $X_1$ and $X_2$ is the phenyl group or the pyridinyl group, the other is a hydrogen atom or a halogen atom; $Y_5$ and $Y_6$ each represent a substituent represented by (a) or (b) given below, a hydrogen atom or a halogen atom; and M represents two hydrogen atoms or a divalent, trivalent or tetravalent metal atom which may have an oxygen atom or a halogen atom,

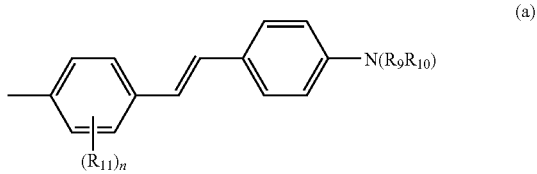

(a)

where $R_{11}$ represents an alkyl group or an alkoxy group, $R_9$ and $R_{10}$ each represent a hydrogen atom, an alkyl group or a substituted or unsubstituted phenyl group, and n is an integer of 1 or 2,

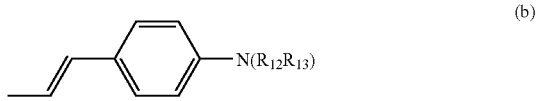

(b)

where $R_{12}$ and $R_{13}$ each represent a hydrogen atom, an alkyl group or a substituted or unsubstituted phenyl group.

<14> The two-photon absorption material according to any one of <1> to <13> above, wherein M is a zinc atom.

<15> The two-photon absorption material according to any one of <1> to <14> above, wherein the two-photon absorption material is used in any one of an optical recording material, an optical molding material, a light restricting material, a two-photon excitation fluorescence material and a three-dimensional optical recording medium.

<16> An optical molding method including:
irradiating a photocurable resin with light for optical molding,
wherein the photocurable resin contains, as at least part thereof, the two-photon absorption material according to any one of <1> to <15> above.

<17> A two-photon excitation fluorescence detection method including:
selectively carrying, on an analyte contained in a sample, the two-photon absorption material according to any one of <1> to <15> above, and
detecting the analyte by detecting two-photon fluorescent light emitted from the two-photon absorption material through light irradiation of the analyte.

<18> A light restricting method including:
restricting a signal light by using a device which restricts a path thereof with a control light,
wherein the device uses, as at least part thereof, the two-photon absorption material according to any one of <1> to <15> above.

<19> A three-dimensional optical recording medium including:
the two-photon absorption material according to any one of <1> to <15> above as at least part of a recording layer where optical recording is performed,
wherein the three-dimensional optical recording medium is formed on a flat surface, and recording and reproducing can be performed horizontally and perpendicularly to the flat surface.

<20> An optical molding apparatus which performs optical molding by irradiating a photocurable resin with light, wherein the two-photon absorption material according to any one of <1> to <15> above is contained as at least part of the photocurable resin.

<21> A light restricting apparatus employing a device which restricts an intensity of light transmitted, wherein the two-photon absorption material according to any one of <1> to <15> above is contained as at least part of the device.

<22> A light restricting apparatus employing a device which restricts a light path, wherein the two-photon absorption material according to any one of <1> to <15> above is contained as at least part of the device.

<23> A two-photon excitation fluorescence detection apparatus, wherein the two-photon absorption material according to any one of <1> to <15> above is selectively carried on an analyte contained in a sample, and the analyte is detected by detecting the two-photon absorption material.

The present invention can provide a two-photon absorption compound which highly efficiently exhibits transition caused by photon absorption. This two-photon absorption compound can be practically applied to production of various materials using a small-scale, inexpensive laser (e.g., three-dimensional memory materials, light restricting materials, photo-curable resins for optical molding (curable materials), materials for photo-chemotherapy, and fluorescent dyes for two-photon fluorescence microscopy). Also, the present invention can provide an industrially advantageous two-photon absorption material.

BRIEF DESCRIPTION OF THE DRAWINGS

FIG. 1A shows a three-dimensional optical recording medium employing, as an optical recording material, a two-photon absorption material of the present invention.

DETAILED DESCRIPTION OF THE INVENTION

Figure 1B:
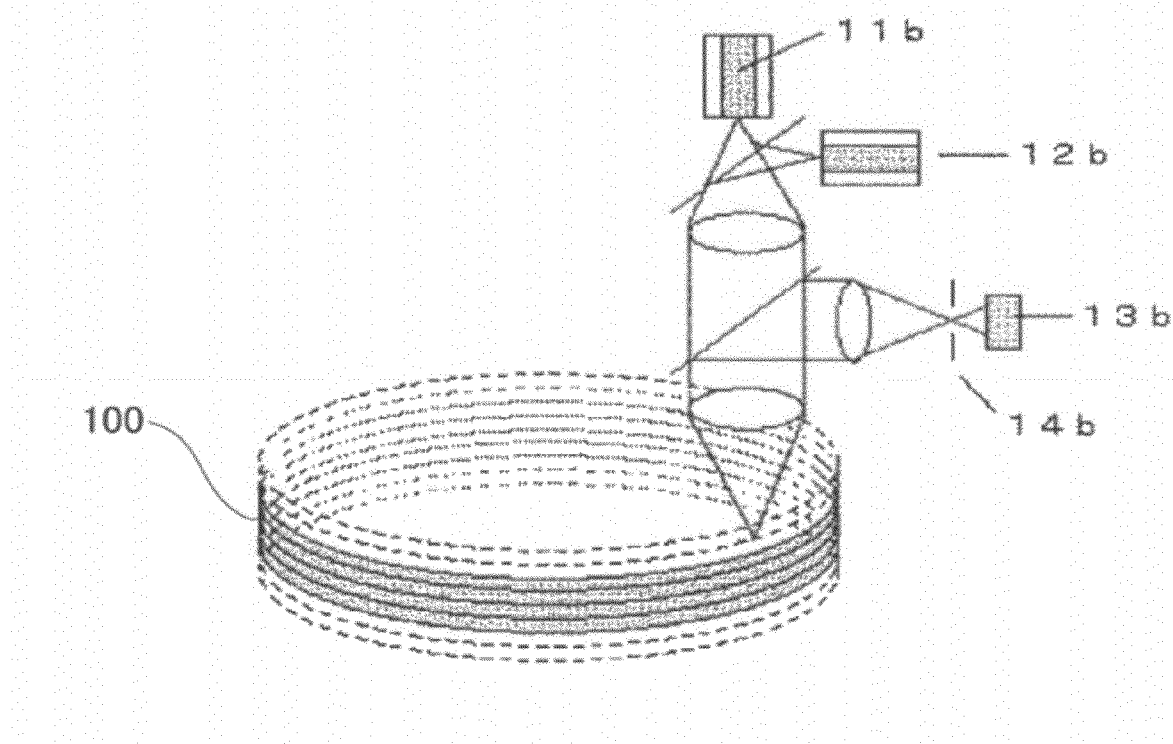
FIG. 1B exemplarily shows a recording apparatus employing the optical recording medium shown in FIG. 1A.

A two-photon absorption material of the present invention can be excited with light having a wavelength falling within a non-resonant region. The actual excited state thereof is at an energy level twice as much as that of photons used for the excitation.

Two-photon absorption is a type of three-dimensional non-linear optical effects. This is a phenomenon in which one molecule absorbs two photons simultaneously to transit from the ground state to the excited state. The two-photon absorption has been known for a long period of time. In recent years, studies on materials having two-photon absorptivity have been advanced, since Jean-Luc Bredas et al. unraveled the relationship between the molecular structure and the mechanism in 1998 (Science, 281, 1653 (1998)).

However, the efficiency of transition caused by this simultaneous two-photon absorption is much less than that of transition caused by one-photon absorption, and the two-photon absorption requires photons having an extremely large power density. Accordingly, two-photon absorption is hardly observed with a generally used laser light intensity. When an ultrashort (femtosecond) pulse laser is used (e.g., a mode locking laser, whose peak light intensity (light intensity at the maximum luminous wavelength) is high), it is confirmed that two-photon absorption is observed.

The efficiency of transition caused by two-photon absorption is proportional to the square of the intensity of an optical field applied (square-law characteristics of two-photon absorption). Accordingly, when a laser beam is applied, two-photon absorption occurs only at a position where the electric field intensity is high; i.e., the center of a laser spot, and two-photon absorption does not occur at all at a position where the electric field intensity is low; i.e., the peripheral portion. In a three-dimensional space, two-photon absorption occurs only at an area where the electric field intensity is high; i.e., a focal point of the laser beam condensed by a lens. Meanwhile, two-photon absorption does not occur at all at an area where the electric field intensity is low; i.e., an area other than the focal point. Compared with one-photon linear absorption in which excitation occurs at all the positions proportionally to the intensity of the optical field applied, for two-photon absorption, excitation occurs only at a pinpoint region in the space by virtue of the square-law characteristics. Thus, spatial resolution is remarkably improved.

By utilizing the above characteristics, three-dimensional memory has been studied which records bit data by changing spectrum, refractive index, or polarized light at predetermined positions of recording media. As described above, two-photon absorption occurs proportionally to the square of the light intensity. Thus, the memory utilizing two-photon absorption realizes ultra resolution recording since its spot size is smaller than that in the memory utilizing one-photon absorption. In addition, attempts have been made to applications of two-photon absorption, having high spatial resolution by virtue of its square-law characteristics, to light restricting materials, photocurable resins for optical molding (photocurable materials), fluorescent dyes for two-photon fluorescence microscopy, etc.

To induce two-photon absorption in a compound, it is possible to employ a short pulse laser of the near infrared region whose wavelengths are longer than those within a wavelength region in which the compound has a linear absorption band and no absorption. Since near infrared light of a transparent region, in which the compound does not have a linear absorption band, is employed, excited light can reach, for example, the inside of a sample, without being absorbed or scattered. Besides, a pinpoint region in the sample can be excited at high spatial resolution by virtue of the square characteristics of two-photon absorption. Thus, two-photon absorption and two-photon luminescence are expected to be applied to two-photon contrast imaging of a biological tissue and photo-chemotherapy such as two-photon photodynamic therapy (PDT). Moreover, when two-photon absorption or two-photon luminescence is employed, photons having higher energy than that of incident photons can be taken out. Thus, studies on up-conversion lasing have been reported in terms of wavelength-conversion devices.

Various inorganic materials have been found out as a two-photon absorption material. However, in the case of the inorganic materials, it is difficult to perform so-called molecular design for providing the materials with desired two-photon absorption characteristics and other optimum characteristics required for device manufacturing. In contrast, in the case of organic compounds, molecular design can be performed to impart desired two-photon absorptivity thereto and to control other properties thereof. Thus, the organic compounds attract large attention since they could be a promising, practical two-photon absorption material.

Dye compounds (e.g., rhodamine and coumalin), dithienothiophene derivatives, oligophenylenevinylene derivatives, and other compounds are known as conventional organic two-photon absorption materials. However, any of these compounds are small in a two-photon absorption cross-sectional area, which indicates two-photon absorptivity per molecule. When a femtosecond pulse laser is used, most of the compounds exhibit a two-photon absorption cross-sectional area smaller than 200 GM (1 GM=$1\times10^{-50}$ cm$^4$·s·molecule$^{-1}$·photon$^{-1}$). Thus, industrial applications of these compounds have not yet been made.

<Application of Two-Photon Absorption Material to Three-Dimensional Multilayered Optical Memory>

In recent years, networks (e.g., the Internet) and high-vision TVs become popular rapidly. Moreover, high-definition television (HDTV) broadcast is starting soon. Thus, demand for mass-storage recording media has been increasing, in order to record image information of 50 GB or higher (preferably 100 GB or higher) inexpensively and simply in consumer use. Furthermore, optical recording media have been demanded for business applications (e.g., computer and broadcast backups) in order to inexpensively record mass information of about 1 TB or more at high speed. Meanwhile, the capacity of conventional two-dimensional optical recording media (e.g., CDs and DVDs) is about 25 GB on physical principles, even if a recording/reproducing wavelength is shortened. This capacity is not enough considering use thereof in future.

Under such circumstances, three-dimensional optical recording media have been prominently expected as ultimately high-density, high-capacity recording media. In the three-dimensional optical recording media, information can be recorded in the form of several tens or several hundreds of superposed layers in a three-dimensional (thickness) direction to achieve ultra high-density, ultra high-capacity recording which is several ten or several hundred times higher than conventional two-dimensional recording media. In three-dimensional optical recording media, information needs to be written with access to a predetermined area in a three-dimensional (thickness) direction. To achieve this, a two-photon absorption material or holography (interference) may be used. In three-dimensional optical recording media using a two-photon absorption material, so-called bit recording, which can record information several ten or several hundred times as much as conventional recording, can be attained based on the aforementioned physical principles, thereby achieving higher recording density. Thus, three-dimensional optical recording media are ultimately high-density, high-capacity optical recording media.

As described above, regarding three-dimensional optical recording media using a two-photon absorption material, there have been proposed a method of reading information through fluorescence by using a fluorescent compound during recording/reproducing (JP-A Nos. 2001-524245 and 2000-512061); a method of reading information through absorption or fluorescence by using a photochromic compound (JP-A Nos. 2001-522119 and 2001-508221); and other methods. However, any of these literatures do not specifically but abstractly describe two-photon absorption compounds such as two-photon absorption compounds with extremely small two-photon absorption efficiency. Moreover, the photochromic compounds described in these patent literatures are reversible materials and thus, there are problems in nondestructive readout, long-term archivability of recorded information, an S/N ratio concerning reproduction, and the like. Thus, the photochromic compounds are not suitably used for optical recording media in practical use. In terms of, among others, nondestructive readout and long-term archivability of recorded information, irreversible materials are preferably used since reproduction can be performed based on change in reflectivity (indices of refraction and absorptivity) or luminescence intensity. However, none of them specifically discloses two-photon absorption materials having such properties.

Also, JP-A Nos. 06-28672 and 06-118306 disclose three-dimensional recording apparatuses, reproducing apparatuses therefor, readout methods therefor, and the like, but do not describe methods using a two-photon absorption, three-dimensional optical recording material.

As described above, the reaction of interest is caused by using excitation energy obtained through non-resonant two-photon absorption. As a result, if luminescence/reflection intensity can be modulated in a non-rewritable mode when a laser focal portion (recording portion) and a laser non-focal portion (non-recording portion) are irradiated with light, it is possible to cause modulation of luminescence/reflection intensity with extremely high spatial resolution at a predetermined area in a three-dimensional space. This can be applied to three-dimensional optical recording media considered as ultimately high-density recording media. Moreover, nondestructive readout can be performed. Furthermore, the material used is an irreversible material and thus, excellent long-term archivability of recorded information can be expected to be attained.

But, two-photon absorption compounds available at the present time have low two-photon absorptivity. Thus, it is necessary to use an extremely high-power laser as a light source, and it takes a long period of time for information recording. In particular, in use thereof in three-dimensional optical recording media, in order to achieve a high transfer rate, it is necessary to design a two-photon absorption, three-dimensional optical recording material which attains recording with high sensitivity based on the differences in optical characteristics (e.g., luminescence and reflection) through two-photon absorption. To achieve this, a material containing a two-photon absorption compound and a recording component is effective, wherein the two-photon absorption compound can be at an excited state by absorbing two photons with high efficiency, and the recording component can efficiently form the differences (e.g., luminescence and reflection) of optical characteristics of the two-photon absorption optical recording material by a predetermined method based on the excited state of the two-photon absorption compound. But, such a material has been hardly disclosed, and demand has arisen for the material and the method for designing it.

A two-photon absorption optical recording material of the present invention can be directly applied to a base with, for example, a spin coater, a roll coater or a bar coater; or can be cast as a film and then laminated on a base by a commonly-used method.

Herein, the "base" refers to any natural or synthetic support, which suitably has a form of a soft or rigid film, a sheet, or a board.

Preferably, the base may be made of, for example, polyethylene terephthalate, resin-undercoated polyethylene terephthalate, polyethylene terephthalate subjected to flame or electrostatic discharge, cellulose acetate, polycarbonate, polymethyl methacrylate, polyester, polyvinyl alcohol or glass. Moreover, a guide groove for tracking and address information may be given to the base in advance.

The solvent used may be removed through evaporation during drying of the product under heating or reduced pressure.

Moreover, a protective layer (an intermediate layer) may be formed on a photosensitive film, which is made of two-photon absorption optical recording material, to prevent oxygen permeation and crosstalk between layers. The protective layer (intermediate layer) is made of polyolefin (e.g., polypropylene or polyethylene), polyvinyl chloride, polyvinylidene chloride, polyvinyl alcohol, or polyethylene terephthalate. Alternatively, the protective layer may be a plastic film or board made of cellophane, which is laminated by an extruder on or electrostatically closely attached to the photosensitive film. Alternatively, a solution of the above-listed polymer may be applied on the photosensitive film, or a glass plate may be attached thereto. Moreover, an adhesive or a liquid substance may be applied between a protective layer and a photosensitive film and/or between a base and a photosensitive film, to thereby enhance airtightness. Furthermore, a protective layer (intermediate layer) disposed between photosensitive films may be provided with a guide groove for tracking and address information in advance.

When light is focused on a predetermined layer of the above three-dimensional multilayered optical recording medium for recording/reproducing, a three-dimensional recording medium of the present invention functions. Even if a protective layer (intermediate layer) is not provided between the layers, it is possible to perform three-dimensional recording in a depth direction by utilizing characteristics of two-photon absorption materials.

FIG. 1A shows an exemplary three-dimensional optical recording medium employing, as an optical recording material, a two-photon absorption material of the present invention. FIG. 1B shows an exemplary recording apparatus employing the optical recording medium. Notably, an optical medium of the present invention is not limited to the embodiment shown in FIG. 1A, and may have any other structures so long as three-dimensional recording (recording in plane and thickness directions) can be attained.

FIG. 1A shows a three-dimensional optical recording media 100 in which recording layers 13a made of a two-photon absorption material of the present invention and intermediate layers 14a (protective layers) are alternately laminated on a flat support (base: 11a) so that the number of layers is 50. Preferably, each recording layer has a thickness of 0.01 μm to 0.5 μm, and each intermediate layer has a thickness of 0.1 μm to 5 μm. With this structure, there can be produced an optical recording medium having the same size as commonly used CDs and DVDs and having large capacity of telabyte grade.

Three-dimensional information recording is performed by focusing light 15a, which is emitted form a light source 11b, on a desired position of each recording layer 13a. The light source may be a single beam light source such as a light source emitting ultrashort pulse light of femtosecond order or a commonly-used LD. Recording can be performed in both bit unit and a depth-direction unit. Also, parallel recording utilizing a surface illuminant is preferably performed from the viewpoint of realizing a higher transfer rate.

Moreover, in a recording medium 100 having no intermediate layers (shown in FIG. 1A); i.e., a bulk recording layer, similar to hologram recording, page data is collectively recorded to realize a high transfer rate.

The support 11a or 12a is a natural or synthetic support, which suitably has a form of a soft or rigid film, a sheet, or a board.

The recording layer 13a can be formed by directly applying, onto a base, a two-photon absorption material of the present invention using, for example, a spin coater, a roll coater or a bar coater. Here, the recording layer may be made of only a two-photon absorption material of the present invention; or may further contain, for example, an organic material, a polymer and a photosensitized material in a mixed or dispersed state.

After film formation through coating with a solvent, the solvent may be removed through evaporation during drying of the product under heating or reduced pressure.

The intermediate layer 14a is formed for the purposes of, among others, preventing oxygen permeation and crosstalk between layers. The intermediate layer is made of, for example, polyolefin (e.g., polypropylene or polyethylene), polyvinyl chloride, polyvinylidene chloride, polyvinyl alcohol, or polyethylene terephthalate. Alternatively, the intermediate layer may be a plastic film or board made of cellophane, which is laminated by an extruder on or electrostatically closely attached to the recording layer (photosensitive film). Alternatively, a solution of the above polymer may be applied on the recording layer, or a glass plate may be attached thereto. Moreover, an adhesive or a liquid substance may be applied between a protective layer and a photosensitive film and/or between a base and a photosensitive film, to thereby enhance airtightness. Furthermore, a protective layer (intermediate layer) disposed between photosensitive films may be provided with a guide groove for tracking and address information in advance.

Information reproducing is performed by irradiating recorded and non-recorded areas with a laser beam having a lower intensity than the beam used for recording, and then detecting the differences in luminescence/reflection intensities between the areas by a detector 13b. Reproducing light may be light with a different wavelength from the beam used for data recording, or light having the same wavelength and lower power. Similar to recording, reproducing can be performed in both bit unit and a depth-direction unit. Also, parallel recording utilizing, for example, a surface illuminant or two-dimensional detector is preferably performed from the viewpoint of realizing a higher transfer rate.

Notably, the shape of an optical recording medium of the present invention may be card, plate, tape or drum (not shown).

<Application to Two-Photon Absorption Material and Optical Molding Apparatus Employing Optical Molding Material>

Photocurable resins used for two-photon optical molding change from a liquid into a solid as a result of two-photon polymerization caused by light irradiation. The resins mainly contain a resin component formed of an oligomer and a reactive diluent; a photopolymerization initiator; and, if necessary, further contain a photosensitized material. The oligomer is a polymer having a polymerization degree of about 2 to about 20 and having many reactive groups at its ends. The reactive diluent is used for controlling the obtained resins in viscosity, hardness, etc. Upon application of light, the polymerization initiator or photosensitized material absorbs two photons. Thereafter, the polymerization initiator directly forms reactive species, or the photosensitized material forms reactive species by the action of the polymerization initiator. The thus-formed reactive species react with the reactive groups of the oligomer and the reactive diluent to initiate polymerization. After initiation of polymerization, a polymerization chain reaction occurs between these compounds to form three-dimensional cross linkage. In this manner, the resins immediately change into a solid resin having a three-dimensional network structure.

The photocurable resins are used for photocurable inks, photo adhesives, lamination-type 3D optical molding, etc., and have been improved so as to have various characteristics. In particular, in lamination-type 3D optical molding, it is important that they have good reactivity, small volume shrinkage upon curing, and excellent mechanical characteristics after curing.

The two-photon absorption material of the present invention can be used as a two-photon absorption polymerization initiator or two-photon absorption photosensitized material which meets the above-described requirements. Since the two-photon absorption material of the present invention has higher two-photon absorption sensitivity than that of conventional two-photon absorption materials, high-speed optical molding can be attained. Also, by virtue of two-photon absorption, fine, three-dimensional optical molding is realized.

In the present invention, the two-photon absorption material of the present invention serving as a photosensitized material is dispersed in, for example, a UV-curable resin to form a photosensitive solid; and the thus-formed photosensitive solid is irradiated with light at its desired points to cause curing reaction only at a portion in the vicinity of the focal point of the irradiated light, whereby an ultrafine three-dimensional optically molded product can be obtained.

Figure 2:
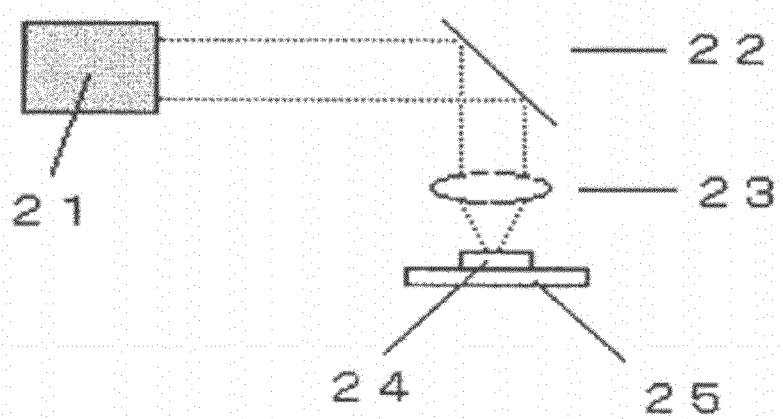
FIG. 2 exemplarily shows an optical molding apparatus which performs optical molding using a two-photon absorption material of the present invention.

FIG. 2 shows an exemplary optical molding apparatus of the present invention used in optical molding using a two-photon absorption material.

In FIG. 2, when a pulse laser beam emitted from a light source 21 is focused, via a movable mirror 22 and through a collective lens 23, on the two-photon absorption material 24 of the present invention, only a region in the vicinity of the collecting point has high photon density. At this time, the total number of photons, which pass through each cross-sectional surface of the beam, is constant; therefore, the summation of the light intensity at each cross-sectional surface is also constant when a beam is scanned two-dimensionally in a focal plane. However, since the occurrence of two-photon absorption is proportional to a square of the light intensity, a region with a high occurrence of two-photon absorption is formed only near the focusing point with a high light intensity. The position of the collecting point can be changed, as desired, in photocurable resin by controlling a movable mirror 22 and/or a movable stage 25 (a galvanometer mirror and a Z stage) and thus, the resin can be locally cured at its any points on the order of nanometers to readily form a desired three-dimensionally processed product.

Figure 3:
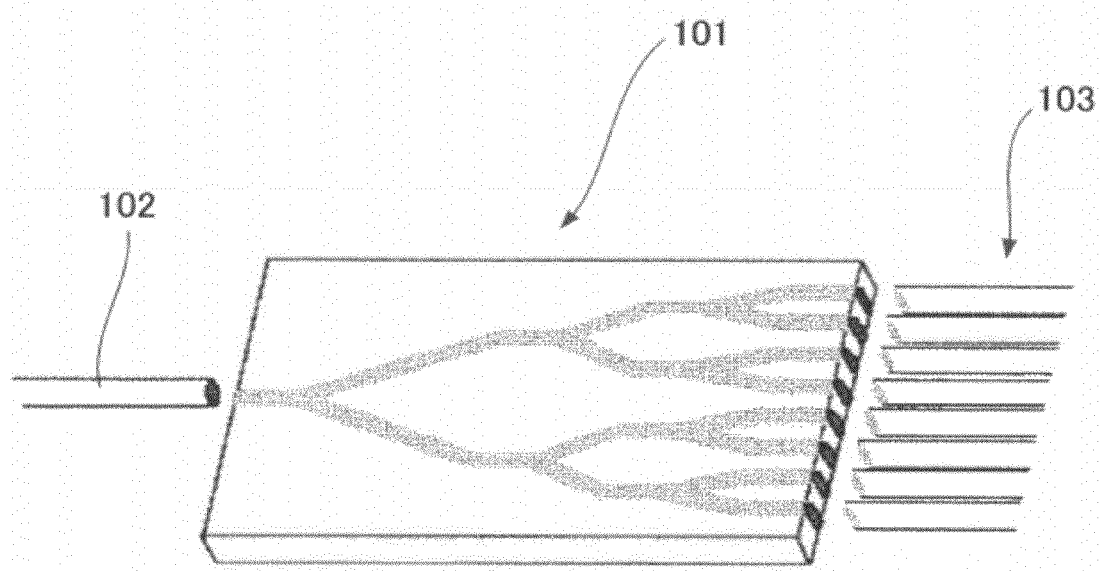
FIG. 3 shows an optical waveguide as one example of an optically molded product produced with an optical molding apparatus.

Also, as an example of the thus-formed optically molded product, an optical waveguide 101 shown in FIG. 3 is taken. In FIG. 3, reference numerals 102 and 103 denote an optical fiber and an optical fiber array, respectively.

In recent years, there has been a demand for recording media with excellent archivability. Also, in order to realize ubiquitous networks, development of optical fiber communication systems has been required to attain high-speed, large-volume information transmission. As one of such systems, so-called wavelength division multiplexing (WDM) is known, which is a large-volume information transmission technique utilizing incoherence of lights with different wavelengths. This WDM essentially requires a device which separates/unites an optical signal with a specific wavelength and thus, uses an optical waveguide as the device. The optical waveguide is provided therein with, for example, a specific refractive index distribution, and can guide an optical signal based on the distribution just like the case where electrons flow through an electrical circuit. The optical waveguide having such a structure that utilizes change in refractive index depending on a light wavelength can be produced by optically molding a thin film containing the two-photon absorption material of the present invention or a solid obtained through dispersing the material in, for example, a photocurable resin with an optical molding apparatus shown in FIG. 2.

JP-A No. 2005-134873 is one of patent literatures which are useful for understanding optical molding in the present invention. From this literature, a pulse laser beam is applied through no mask to a surface of a photosensitive polymer film for interference exposure. The laser beam is composed of light (wavelength) which enables the photosensitive polymer film to exhibit its photosensitivity, and is selected in consideration of the type of a photosensitive polymer used, or the photosensitive group or moiety of the polymer.

Meanwhile, examples of patent literatures regarding an optical waveguide include JP-A Nos. 08-320422, 2004-277416, 11-167036 and 2005-257741. JP-A No. 08-320422 discloses an optical waveguide formed by irradiating a light refractive index material with light.

Optical molding using the two-photon absorption material of the present invention has the following advantageous features over conventional optical molding:

(1) Resolution Exceeding Diffraction Limit

By virtue of nonlinearity of two-photon absorption against light intensity, a photocurable resin is cured only at a focal point of light irradiated and thus, resolution exceeding the diffraction limit of the light is realized.

(2) Ultra High-Speed Optical Molding

Optical molding using the two-photon absorption material of the present invention exhibits higher two-photon absorption sensitivity than conventional optical molding, which can increase scanning speed of a beam used.

(3) Three-Dimensional Processability

Photocurable resins are transparent to the near-infrared light which induces two-photon absorption. Thus, internal curing can be achieved even when a focused beam is focused deeply into the resin. The problem associated with existing SiH—when a beam is focused deeply, difficulty is encountered in internal curing due to the decreased light intensity of the collecting point caused as a result of light absorption—can be solved with certainty according to the present invention.

(4) High Yield

There are problems in that an optically molded product is broken or deformed by the action of viscosity or surface tension of the resin in existing methods. However, such problems can be solved since optical molding is performed inside the resin according to the present invention.

(5) Mass Production

It is possible to manufacture a large number of parts or movable bodies continuously in a short period of time by utilizing ultra high-speed optical molding.

<Application of Two-Photon Absorption Material to Light Restricting Device>

In optical communication and optical information processing, optical controls (e.g., modulation and switching) are required to transfer signals of, for example, information with the aid of light. This type of optical control conventionally employs an electrical-optical control method using an electric signal. However, the electrical-optical control method is limited in terms of bands, due to CR time constant of an electrical circuit, and of a processing speed (>10 ps), due to a response speed of a device itself and to a difference in speed between electric signals and optical signals. Thus, an optical-optical control technology, which controls an optical signal by an optical signal, is very important to make full use of advantages of light such as its broad band and high-speed performance. Optical devices fabricated by processing the two-photon absorption material of the present invention in order to meet the requirements can be applied to, for example, high-speed optical switches in optical communication, optical switching, optical computers, optical interconnection, etc. by utilizing optical changes in, for example, transmittance, refractive index, and an absorption coefficient caused by light irradiation to modulate light intensity and frequency without an electronic circuit technology.

The light restricting device in the present invention utilizing optical characteristics changes caused by two-photon absorption exhibits a much higher response speed (<1 ps) than commonly-used light restricting devices which are formed from a semiconductive material or based on one-photon excitation. Also, by virtue of its high sensitivity, there can be provided light restricting devices which exhibit excellent signal characteristics and a high S/N ratio.

<Optical Switch Utilizing One-Photon Absorption/Supersaturation Absorption and its Problems>

For reference, optical switches utilizing one-photon absorption/supersaturation absorption are described as follows. They are based on, for example, spectral hole burning (SHB), excitation/absorption, intersubband transition (ISBT) and quantum confined stark effect (QCSE). However, they pose problems in that, for example, ultra high-speed response is difficult to attain, intricate device manufacturing (composition and structure) is required, an employable wavelength region is narrow in many cases (i.e., selectivity in wavelengths is poor), and dependency on polarization is large.

<Advantage of Optical Switch Utilizing Two-Photon Absorption>

In contrast, optical switches utilizing two-photon absorption can employ nonlineality thereof. As a result, they are advantageous in that ultra high-speed response can be attained in principle, device manufacturing (composition and structure) is readily performed, an employable wavelength region is broad (i.e., high selectivity in wavelengths), and dependency on polarization is not observed.

<Application of Change in Absorption Characteristics>

Figure 4:
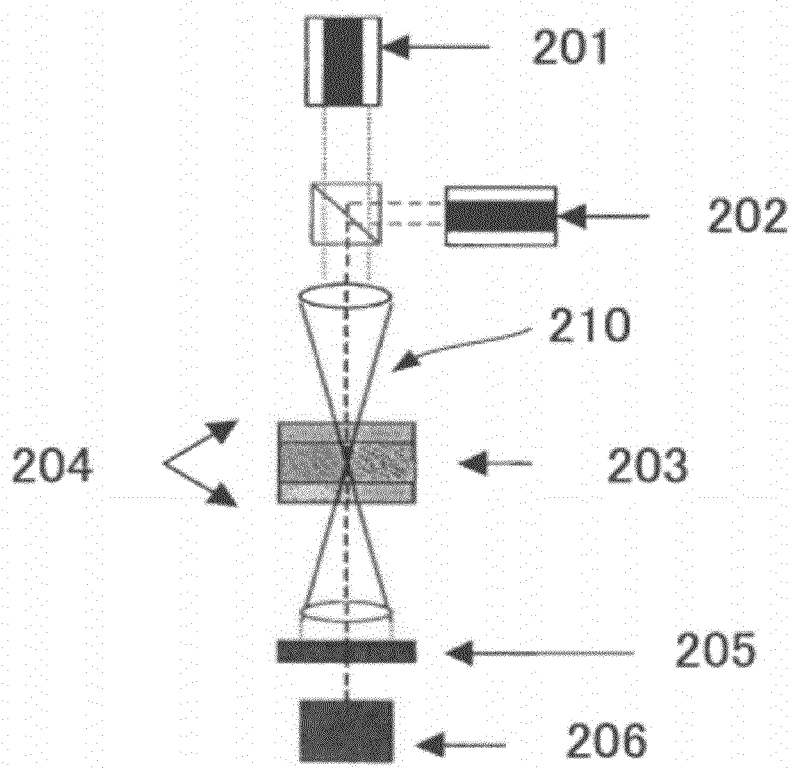
FIG. 4 shows an exemplary optical controlling device in which a two-photon absorption material of the present invention is two-photon excited using a control light having a wavelength capable of causing two-photon excitation, to thereby optically switch a signal light having a wavelength capable of causing one-photon excitation.

FIG. 4 shows an exemplary optical controlling device in which the two-photon absorption material of the present invention is two-photon excited using a control light having a wavelength capable of causing two-photon excitation, to thereby optically switch a signal light having a wavelength capable of causing one-photon excitation. The optical device shown in FIG. 4 is a device having two protective layers and a two-photon absorption material disposed therebetween, which is not construed as limiting the present invention thereto.

Laser beams emitted as a control light 201 and a signal light 202 are focused by a focusing apparatus. Only when the control light 201 has a very high intensity, the control light is absorbed by an optical device 203, which changes transmittance with respect to light having a wavelength capable of causing one-photon excitation. Using change in transmittance depending on nonlineality of two-photon absorption, it is possible that the signal light is optically switched depending on the intensity of the control light. In FIG. 4, reference numerals 204, 205 and 206 denote protective films, a color filter and a detector, respectively.

Figure 5A:
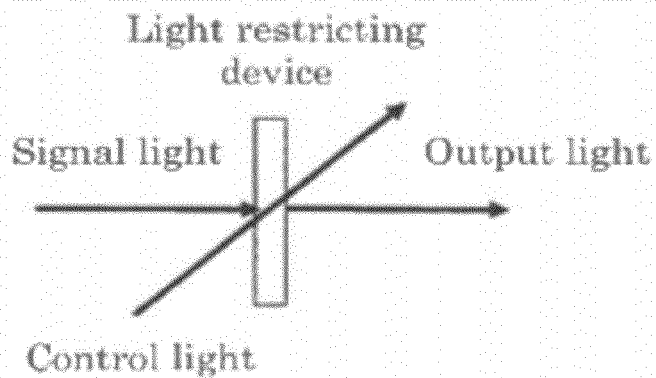
FIG. 5A exemplarily illustrates operation of an optical controlling device in which all-optical switching is performed by two-photon exciting a two-photon absorption material of the present invention using a signal light with a wavelength (λ1) capable of causing two-photon excitation and a control light with a wavelength (λ2) capable of causing two-photon excitation.
Figure 5B:
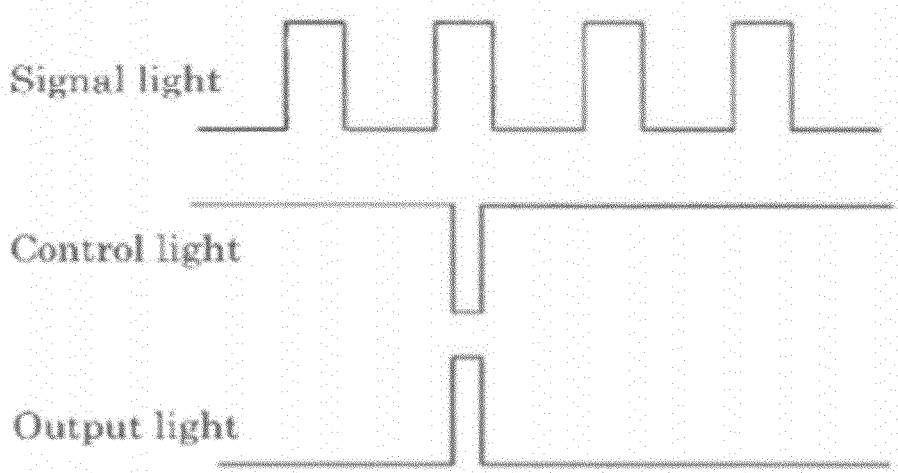
FIG. 5B exemplarily illustrates operation of an optical controlling device in which all-optical switching is performed by two-photon exciting a two-photon absorption material of the present invention using a signal light with a wavelength (λ1) capable of causing two-photon excitation and a control light with a wavelength (λ2) capable of causing two-photon excitation.

FIGS. 5A and 5B each exemplarily illustrate operation of an optical controlling device in which all-optical switching is performed by two-photon exciting the two-photon absorption material of the present invention using a signal light with a wavelength ($\lambda 1$) capable of causing two-photon excitation and a control light with a wavelength ($\lambda 2$) capable of causing two-photon excitation.

Laser beams serving as the control and signal lights are focused by a focusing apparatus on a light restricting device having, as a main component, an element made of the two-photon absorption material. When the control light is off, the signal light is output as is; whereas the control light is on, the control light and the signal light are two-photon absorbed, resulting in that the signal light is not output. In this manner, optical switching of a signal light can be performed depending on on/off of a control light.

<Applications of Change in Refractive Index>

Figure 6A:
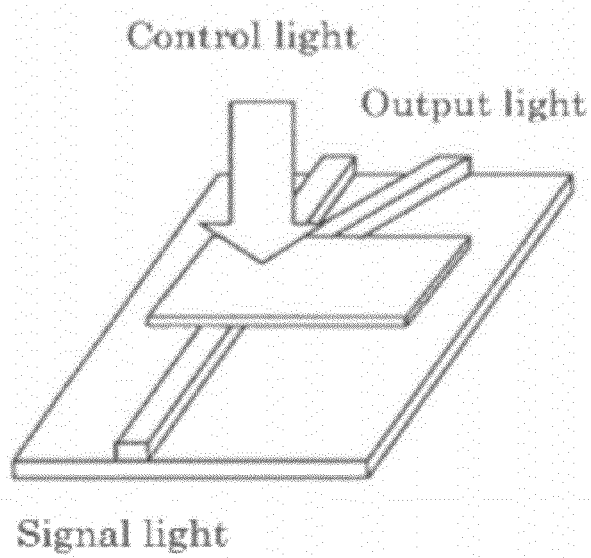
FIG. 6A illustrates an exemplary optical controlling device in which light paths for light output are optically switched by two-photon exciting a two-photon absorption material of the present invention with a control light having a wavelength capable of causing two-photon absorption.
Figure 6B:
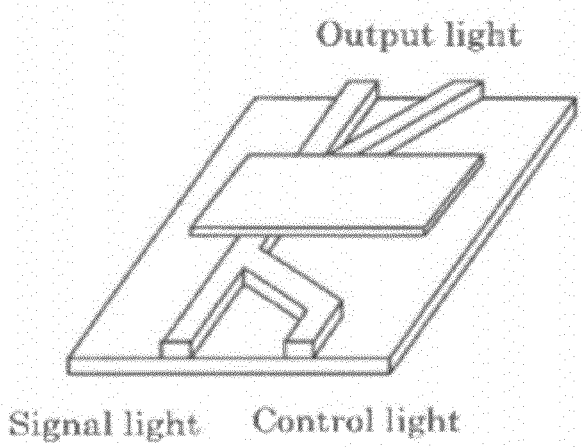
FIG. 6B illustrates an exemplary optical controlling device in which light paths for light output are optically switched by two-photon exciting a two-photon absorption material of the present invention with a control light having a wavelength capable of causing two-photon absorption.

FIGS. 6A and 6B each illustrate an exemplary optical controlling device in which light paths for light output are optically switched by two-photon exciting the two-photon absorption material of the present invention with a control light having a wavelength capable of causing two-photon absorption.

Laser beams emitted as a control light and a signal light are focused by a focusing apparatus on a branching point of an optical waveguide made mainly of the two-photon absorption material. Only when the control light has a very high intensity, the control light is absorbed in the branching point, causing change in refractive index at the point. As a result of two-photon absorption, by adjusting refractive indices at the branching point and optical waveguides for signal and output lights, the light path for the output light can be switched. In this manner, optical switching for an optical waveguide can be performed by utilizing change in refractive index depending on nonlineality of two-photon absorption.

JP-A No. 08-320422 is one of patent literatures which are useful for understanding a light restricting device in the present invention. From this literature, a material whose refractive index changes through light irradiation is irradiated with light having a wavelength capable of changing its refractive index for focusing, to thereby produce an optical waveguide having a refractive index distribution. In the present invention, the two-photon absorption material having high two-photon absorptivity, a thin film formed therefrom, or a solid obtained through dispersing the material in, for example, a photocurable resin is used as an optical device. And, light with a wavelength of $\lambda 1$ is applied to the device for excitation, and then light with a wavelength of $\lambda 2$ is applied to the thus-excited device for further excitation, whereby an optical waveguide utilizing a refractive index distribution depending on a light wavelength can be designed. Also, many two-photon absorption materials emit a fluorescent light. Thus, a fluorescent substance is disposed on one output end or in the vicinity thereof in an optical device, and then an excitation light ($\lambda 1$) is caused to emit from the other output end, whereby a refractive index distribution can be formed using the excitation light and the fluorescent light ($\lambda 2$). In this case, the fluorescent light is generally lower in intensity than the excitation light and thus, sensitivity is preferably higher to a wavelength of the fluorescent light. Examples of the fluorescent substance include dispersions prepared by dispersing fluorescent dyes in a photocurable substance, various resins, etc.

<Application of Two-Photon Absorption Material to Two-Photon Excited Fluorescence Detection Method and Apparatus>

Figure 7:
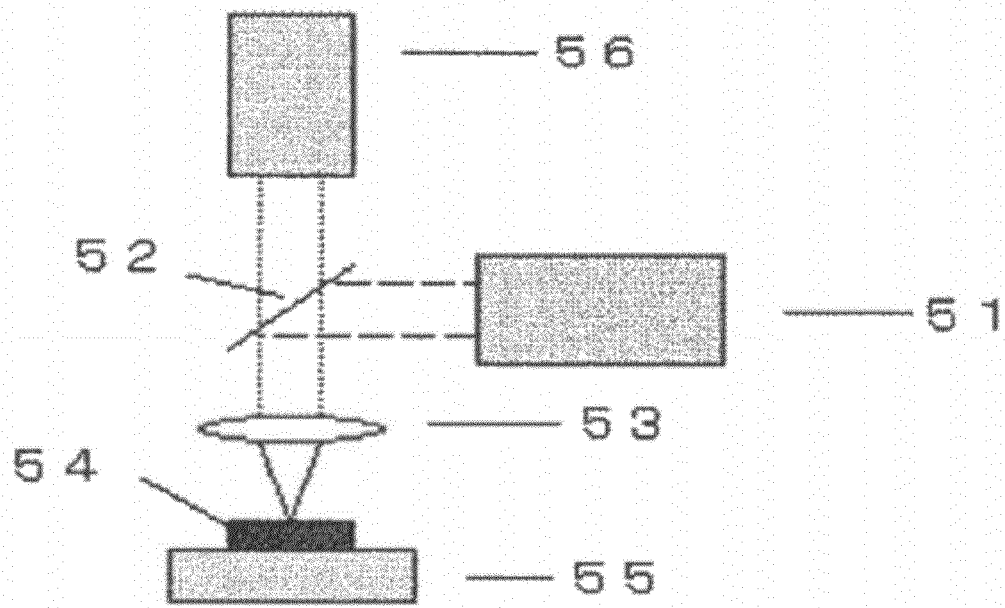
FIG. 7 exemplarily shows a two-photon excitation fluorescence microscope.

The two-photon excited fluorescence detection method is a detection method in which a near-infrared pulse laser beam is focused for scanning on a sample containing an analyte labeled with a two-photon fluorescent material, and then fluorescent light emitted from the analyte through two-photon excitation to obtain a three-dimensional image thereof. FIG. 7 shows a two-photon excitation fluorescence microscope as one example of such optical devices.

In the apparatus shown in FIG. 7, a near-infrared subpicosecond monochromatic coherent pulse laser beam emitted from a light source 51 is focused via a dichroic mirror 52 using a focusing apparatus 53 in a sample 54 containing an analyte labeled with a two-photon absorption material of the present invention, causing the analyte to emit two-photon fluorescent light. The laser beam is focused on some points of the sample, and the fluorescent intensity of each point is detected with an optical detector 56. The thus-obtained fluorescent intensity and position-related information of the point are plotted against each other on a computer, to thereby form a three-dimensional fluorescent image. In this case, the microscope is provided with a scanning mechanism in which a laser beam is focused on a desired point. In order to achieve this, for example, a sample may be moved on a stage 55 or a movable mirror (e.g., a galvanometer mirror) may be used for scanning of laser beam.

The two-photon excitation fluorescence microscope having the above-described configuration can provide a high-resolution image in an optical axis direction. Also, using a confocal pinhole plate, further increased resolution can be attained in both in-plane and optical axis directions.

Such a two-photon fluorescent material can be used for staining an analyte, or dispersed in an analyte in use. It can be used not only for industrial applications but also for three-dimensional microimaging of, for example, living cells. In addition, when mixed with a biocompatible polymer, it can be used as a photosensitive material in photodynamic therapy (PDT).

JP-A No. 09-230246 is one of patent literatures which are useful for understanding a two-photon excitation fluorescence microscope in the present invention. For example, a scanning fluorescent microscope has a laser beam irradiation optical system which emits a collimated light enlarged to a desired size, and a base on which surface a plurality of light-focusing elements are formed. Each light-focusing element is arranged so that the position where light is focused is identical to the position where an image is formed in an objective lens system. Further, a beam splitter that transmits a long-wavelength light and reflects short-wavelength light is disposed between the base and the objective lens system. In such a microscope, a fluorescent light is emitted from the surface of a sample as a result of multi-photon absorption.

With this configuration, high resolution can be attained in an optical axis direction by utilizing nonlinearity of multi-photon absorption. In addition, using a confocal pinhole plate, further increased resolution can be attained in both in-plane and optical axis directions. Similar to the above-described case, such a two-photon optical device may be an optical device which is made of the two-photon absorption material of the present invention having high two-photon absorptivity, a thin film formed therefrom, or a solid obtained through dispersing the material in, for example, a photocurable resin.

The two-photon absorption material of the present invention can be applied to an apparatus in which a two-photon excitation fluorescent light is detected (e.g., a two-photon excitation laser scanning microscope). This two-photon absorption material has a larger two-photon absorption cross-sectional area than conventional two-photon excitation fluorescent materials. Thus, even when used at low concentration, it exhibits high two-photon absorption (light emitting) characteristics. The present invention can provide a high sensitive two-photon absorption material. Thus, it is not necessary to irradiate the material with light having high intensity, avoiding degradation or breakage of an analyte. In addition, it is possible to reduce adverse effects against characteristics of other components in the analyte. Similarly, when it is applied in biological subjects, the intensity of light irradiated can be decreased to reduce damage thereto.

<Photodynamic Therapy>

Photodynamic therapy (PDT) is a therapeutic method which has already been clinically applied to the treatment of some early-stage malignant tumors in human medicine.

Specifically, a photosensitive compound (two-photon absorption material) is made to be taken in tumor cells and/or endothelial cells of neovascular vessels in tumor tissues, and then an affected area (i.e., these cells) is irradiated with a laser beam to generate active oxygen. Presumably, tumor cells/tissues are given damage by the action of active oxygen, leading to disappearance of tumor.

PDT employs photodynamic reaction. It uses a low-toxic photosensitive compound and a laser beam having low intensity and thus, advantageously gives less damage to biological subjects.

Also, when the photosensitive compound used is a two-photon absorption material and the light used has such a long wavelength that can transmit biological subjects, damage to biological subjects is further reduced.

In this therapeutic method, first, diagnostic imaging (e.g., CT) of tumor is performed to confirm the position and size thereof. Based on the obtained CT image, an optical fiber is placed so as to irradiate the entire tumor with a laser beam, followed by irradiation of a laser beam.

In surgical therapy, tumor is extirpated through operation after opening a body and thus, functions or forms of the body may be deteriorated. In contrast, PDT can advantageously save normal tissues to the greatest extent possible.

The two-photon absorption material of the present invention can be applied to various devices as a bulk or a thin film formed exclusively of the material, or a mixture of the material and various resins.

For example, in optical discs, the thin film is in contact with a base. Examples of the material for the base include polyethylene terephthalates, polycarbonates, polymethyl methacrylates, polyesters, polyvinyl alcohols and glass. Meanwhile, when additional layers are provided on the base, the thin film is in contact with an intermediate layer (partition layer). The intermediate layer is plastic films made, for example, of polyolefin (e.g., polypropylene and polyethylene), polyvinyl chloride, vinylidene chloride, polyvinyl alcohol, polyethylene terephthalate, cellophane, or various photocurable resin.

Also, when applied to various optical devices and optical molding devices, the two-photon absorption material is in use mixed with various resins or photocurable resins.

Thus, in use, the two-photon absorption material of the present invention is required to be mixed with various resins or glass; or a layer made of the two-photon absorption material is required to be in contact with various resins or glass.

In other words, the two-photon absorption material of the present invention is in contact with various resins or glass at the micro or macro level.

Next will be roughly described general production methods for porphyrin derivatives of the present invention, and characteristic structures of the porphyrin derivatives of the present invention.

One of the general production methods is the below-described Lindsey method found by Lindsey et al. Specifically, pyrrole is reacted with aromatic aldehyde at $10^{-2}$ M in methylene chloride in the presence of a catalytic amount of $BF_3$ ($10^{-3}$ M) or trifluoroacetic acid ($10^{-2}$ M) to form a tetramer, followed by oxidation with p-chloranil. With this method, commonly-used porphyrins can be synthesized at relatively high yield.

In general, porphyrins produced from pyrrole and aldehyde virtually have a four axisymmetric structure, and are disadvantageous in that they do not exhibit high two-photon absorption in terms of low polarity thereof.

In view of this, a substituted or unsubstituted dipyrrolomethane is synthesized, and the thus-obtained dipyrrolomethane, serving as a starting material, is reacted with aldehyde in accordance with the Lindsey method, whereby low-symmetry porphyrins can be produced.

In particular, when meso(trifluoromethyl)dipyrrolomethane described in J. Org. Chem. 1996, 61, pp. 7,534 to 7,544 is synthesized and then used to produce low-symmetry porphyrins, the obtained porphyrins exhibit increased polarity, increased two-photon absorptivity targeted by the present invention, and increased solubility to a solvent by virtue of fluorine atoms. Also, even when dipyrrolomethane having no substituent at a meso position is used as a starting material, non-symmetry porphyrins can be produced. The non-symmetry porphyrins have no substituents at two meso positions, and the meso positions can be halogenated and then substituted by specific substituents.

Regarding this halogenation, reference may be made to, for example, J. Org. Chem. 1993, 58, pp. 5,983 to 5,993 and J. Chem. Soc., Chem. Commun., 1995, 5, pp. 527 and 528.

In the present invention, in terms of polarity, an electron-donating substituent (i.e., a substituent having high electron donating property) is introduced into 1 to 3 meso positions to achieve excellent two-photon absorptivity. Among others, a triphenylamine group has high electron donating property and is a bulky substituent. Thus, porphyrins containing, as a substituent, such a triphenylamine group can be dissolved in various organic solvent by virtue of a triphenylamine group, and this substituent is particularly useful for film formation. When Zn is used as a central metal in the porphyrins, the formed porphyrins exhibit sharp absorption and improve in two-photon absorptivity. Thus, the optimum central metal is Zn. In addition, inclusion of Zn in a porphyrin ring can be performed at higher yield as compared with the case where the other metals are used and thus, Zn is the most suitable metal for industrial applications.

Two-Photon Absorption Material According to First Embodiment

A two-photon absorption material of the present invention is a compound represented by the following General Formula (I).

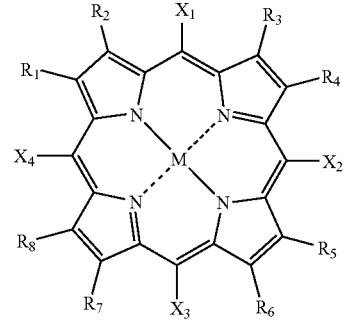

General Formula (I)

where $R_1$ to $R_8$ each represent a hydrogen atom, a halogen atom, a carboxyl group, a carboxylic acid ester group, a substituted or unsubstituted aryl group, or a substituted or unsubstituted alkyl group; one to three of $X_1$ to $X_4$ each represent a substituted or unsubstituted amino group, a substituted or unsubstituted aminophenyl group, a substituted or unsubstituted dialkylaminophenyl group, a substituted or unsubstituted N,N-diphenyl-aminophenyl group, a substituted or unsubstituted indolyl group, or a substituted or unsubstituted azulenyl group, and the other represents or the others each represent a hydrogen atom, a halogen atom, a carboxyl group, a carboxylic acid ester group, a substituted or unsubstituted aryl group, a substituted or unsubstituted pyridinyl group, a substituted or unsubstituted alkyl group or a perhalogenoalkyl group; and M represents two hydrogen atoms or a divalent, trivalent or tetravalent metal atom which may have an oxygen atom or a halogen atom.

In General Formula (I), preferably, one to three of $X_1$ to $X_4$ each represent a substituted or unsubstituted amino group, a substituted or unsubstituted aminophenyl group, a substituted or unsubstituted dialkylaminophenyl group, a substituted or unsubstituted N,N-diphenyl-aminophenyl group, a substituted or unsubstituted indolyl group, or a substituted or unsubstituted azulenyl group, and the other is or the others each are a trifluoromethyl group.

In General Formula (I), preferably, one to three of $X_1$ to $X_4$ each are a substituted or unsubstituted N,N-diphenyl-aminophenyl group.

Examples of the alkyl group represented by each of $X_1$ to $X_4$ and $R_1$ to $R_8$ in General Formula (I) include linear or branched alkyl groups and substituted alkyl groups. Examples of the substituted alkyl groups include hydroxy-substituted alkyl groups such as 2-hydroxyethyl, 3-hydroxypropyl, 4-hydroxybutyl and 2-hydroxypropyl; carboxy-substituted alkyl groups such as carboxymethyl, 2-carboxyethyl and 3-carboxypropyl; cyano-substituted alkyl groups such as 2-cyanoethyl and cyanomethyl; amino-substituted alkyl groups such as 2-aminoethyl; halogen-substituted alkyl groups such as 2-chloroethyl, 3-chloropropyl, 2-chloropropyl and 2,2,2-trifluoroethyl; phenyl-substituted alkyl groups such as benzyl, p-chlorobenzyl and 2-phenylethyl; alkoxy-substituted alkyl groups such as 2-methoxyethyl, 2-ethoxyethyl, 2-(n)propoxyethyl, 2-(iso)propoxyethyl, 2-(n)butoxyethyl, 2-(iso)butoxyethyl, 2-(2-ethylhexyloxy)ethyl, 3-methoxypropyl, 4-methoxybutyl and 2-methoxypropyl; alkoxyalkoxy-substituted alkyl groups such as 2-(2-methoxyethoxy)ethyl, 2-(2-ethoxyethoxy)ethyl, 2-(2-(n)propoxyethoxy)ethyl, 2-(2-(iso)propoxyethoxy)ethyl, 2-(2-(n)butoxyethoxy)ethyl, 2-(2-(iso)butoxyethoxy)ethyl and 2-{2-(2-ethylhexyloxy)ethoxy}ethyl; substituted alkyl groups such as allyloxyethyl, 2-phenoxyethyl and 2-benzyloxyethyl; acyloxy-substituted alkyl groups such as 2-acetyloxyethyl, 2-propionyloxyethyl, 2-(n)butylyloxyethyl, 2-(iso)butylyloxyethyl and 2-trifluoroacetyloxyethyl; substituted or unsubstituted alkoxycarbonyl-substituted alkyl groups such as methoxycarbonylmethyl, ethoxycarbonylmethyl, (n) propoxycarbonylmethyl, (iso)propoxycarbonylmethyl, (n) butoxycarbonylmethyl, (iso)butoxycarbonylmethyl, 2-ethylhexyloxycarbonylmethyl, benzyloxycarbonylmethyl, furfuryloxycarbonylmethyl, tetrahydrofurfuryloxycarbonylmethyl, 2-methoxycarbonylethyl, 2-ethoxycarbonylethyl, 2-(n)propoxycarbonylethyl, 2-(iso)propoxycarbonylethyl, 2-(n)butoxycarbonylethyl, 2-(iso)butoxycarbonylethyl, 2-(2-ethylhexyloxycarbonyl)ethyl, 2-benzyloxycarbonylethyl and 2-furfuryloxycarbonylethyl; substituted or unsubstituted alkoxycarbonyloxy-substituted alkyl groups such as 2-methoxycarbonyloxyethyl, 2-ethoxycarbonyloxyethyl, 2-(n)propoxycarbonyloxyethyl, 2-(iso)propoxycarbonyloxyethyl, 2-(n)butoxycarbonyloxyethyl, 2-(iso)butoxycarbonyloxyethyl, 2-(2-ethylhexyloxycarbonyloxy)ethyl, 2-benzyloxycarbonyloxyethyl and 2-furfuryloxycarbonyloxyethyl; and hetro ring-substituted alkyl groups such as furfuryl and tetrahydrofurfuryl.

Also, examples of cycloalkyl groups include cyclopentyl and cyclohexyl.

Specific examples of the alkyl group include primary alkyl groups such as methyl, ethyl, n-propyl, n-butyl, isobutyl, n-pentyl, neopentyl, isoamyl, 2-methylbutyl, n-hexyl, 2-methylpentyl, 3-methylpentyl, 4-methylpentyl, 2-ethylbutyl, n-heptyl, 2-methylhexyl, 3-methylhexyl, 4-methylhexyl, 5-methylhexyl, 2-ethylpentyl, 3-ethylpentyl, n-octyl, 2-methylheptyl, 3-methylheptyl, 4-methylheptyl, 5-methylheptyl, 2-ethylhexyl, 3-ethylhexyl, n-nonyl, n-decyl and n-dodecyl; secondary alkyl groups such as isopropyl, sec-butyl, 1-ethylpropyl, 1-methylbutyl, 1,2-dimethylpropyl, 1-methylheptyl, 1-ethylbutyl, 1,3-dimethylbutyl, 1,2-dimethylbutyl, 1-ethyl-2-methylpropyl, 1-methylhexyl, 1-ethylheptyl, 1-propylbutyl, 1-isopropyl-2-methylpropyl, 1-ethyl-2-methylbutyl, 1-propyl-2-methylpropyl, 1-methylheptyl, 1-ethylhexyl, 1-propylpentyl, 1-isopropylpentyl, 1-isopropyl-2-methylbutyl, 1-isopropyl-3-methylbutyl, 1-methyloctyl, 1-ethylheptyl, 1-propylhexyl and 1-isobutyl-3-methylbutyl; tertiary alkyl groups such as tert-butyl, tert-hexyl, tert-amyl and tert-octyl; and cycloalkyl groups such as cyclohexyl, 4-methylcyclohexyl, 4-ethylcyclohexyl, 4-tert-butylcyclohexyl, 4-(2-ethylhexyl)cyclohexyl, bornyl, isobornyl and adamantine. Note that these alkyl groups may have a substituent such as a halogen atom.

In the present invention, specific examples of the aryl group represented by each of $X_1$ to $X_4$ and $R_1$ to $R_8$ in General Formulas include phenyl, methylphenyl, dimethylphenyl, trimethylphenyl, ethylphenyl, tert-butylphenyl, di(tert-butyl)phenyl, butylphenyl, methoxyphenyl, dimethoxyphenyl, trimethoxyphenyl and butoxyphenyl. Note that these aryl groups may have a substituent such as a halogen atom.

In General Formula (I), M represents two hydrogen atoms or a divalent, trivalent or tetravalent metal atom which may have an oxygen atom or a halogen atom. Examples of the metal atom represented by M include metals belonging to Groups Ib, IIa, IIb, IIIa, IVa, IVb, Vb, VIb, VIb and VIII, oxides of the metals, halides of the metals, hydroxides of the metals, and the metals having a substituent(s).

Specific examples of the metals include Cu, Zn, Mg, Al, Ge, Ti, Sn, Pb, Cr, Mo, Mn, Fe, Co, Ni, In, Pt and Pd. Specific examples of the oxides include TiO and VO. Specific examples of the halides include AlCl, $GeCl_2$, $SiCl_2$, FeCl, $SnCl_2$ and InCl. Specific examples of the hydroxides include $Al(OH)_3$, $Si(OH)_2$, $Ge(OH)_2$ and $Sn(OH)_2$.

In the metals having a substituent(s), the metal is, for example, Al, Ti, Si, Ge or Sn; and the substituent is, for example, an aryloxyl group, an alkoxyl group, a trialkylsiloxyl group, a triarysiloxyl group, a trialkoxysiloxyl group, a triaryloxysiloxyl group, a trityloxyl group or an acyloxyl group.

Exemplary porphyrin derivatives represented by General Formula (I) are given below.
No. 1
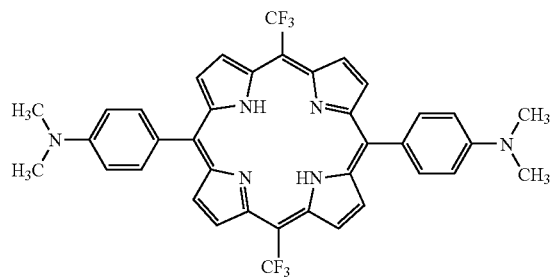
No. 2
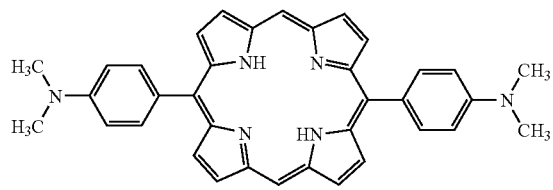
No. 3
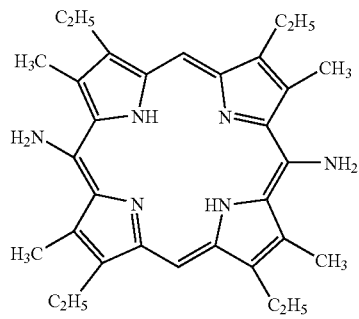
No. 4
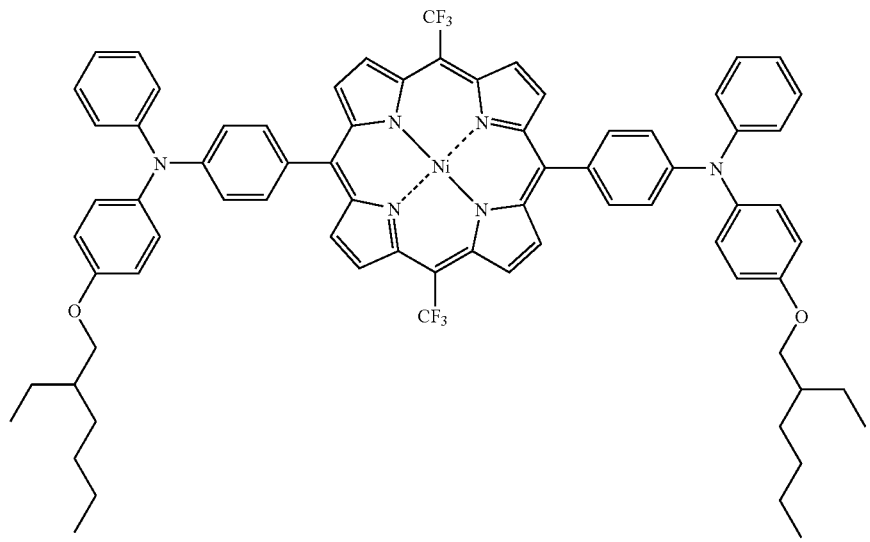

-continued
No. 5
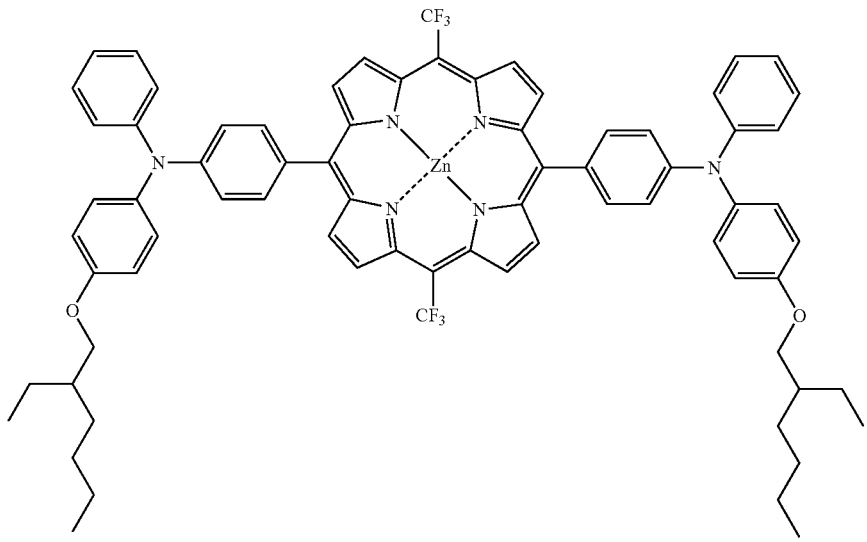
No. 6
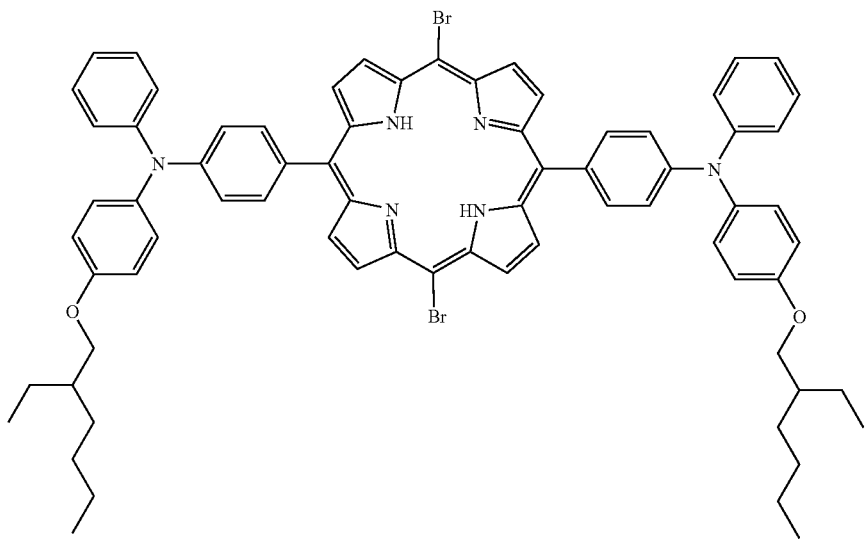
No. 7
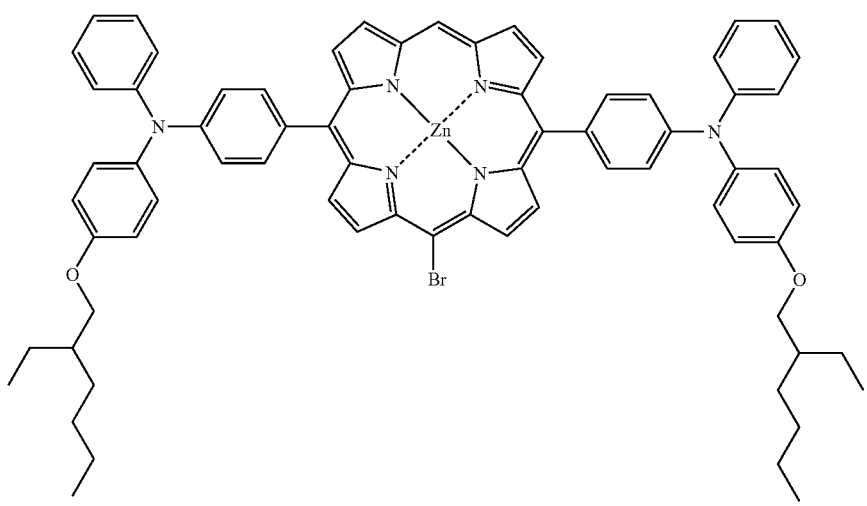

-continued
No. 8
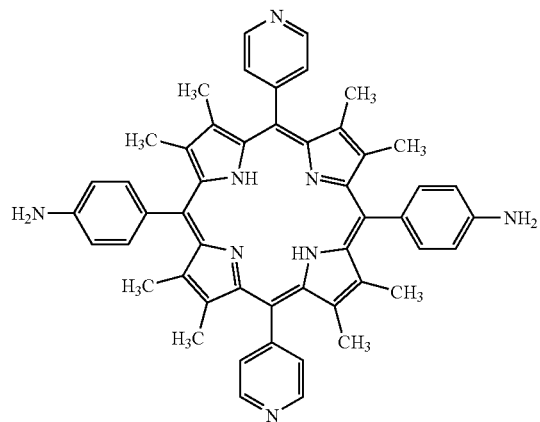
No. 9
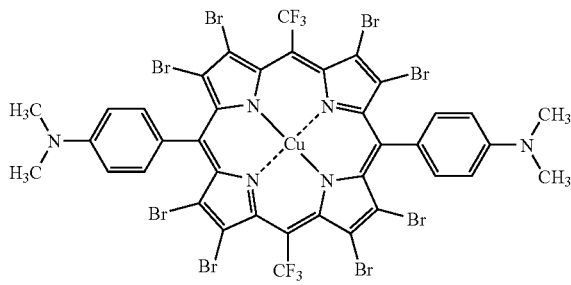
No. 10
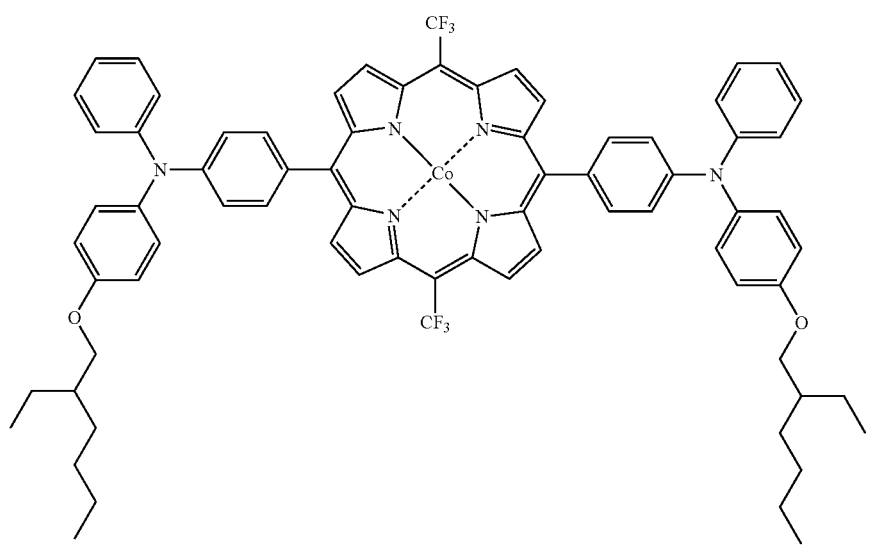
No. 11
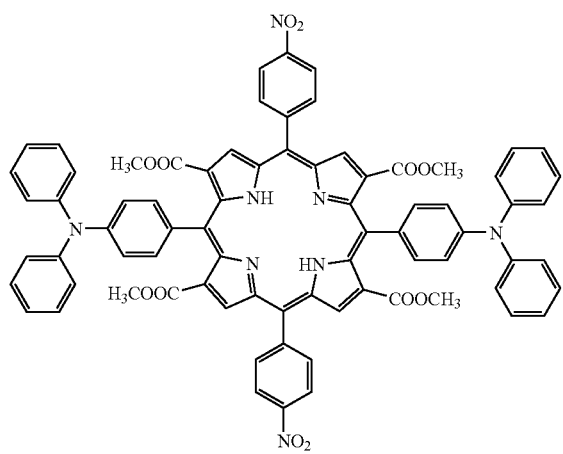
No. 12
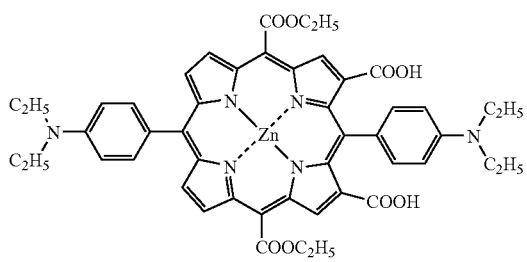

No. 13
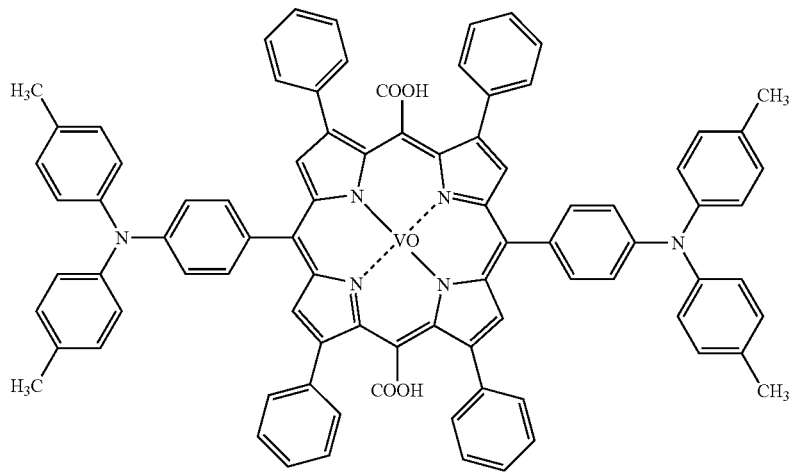
No. 14
No. 15
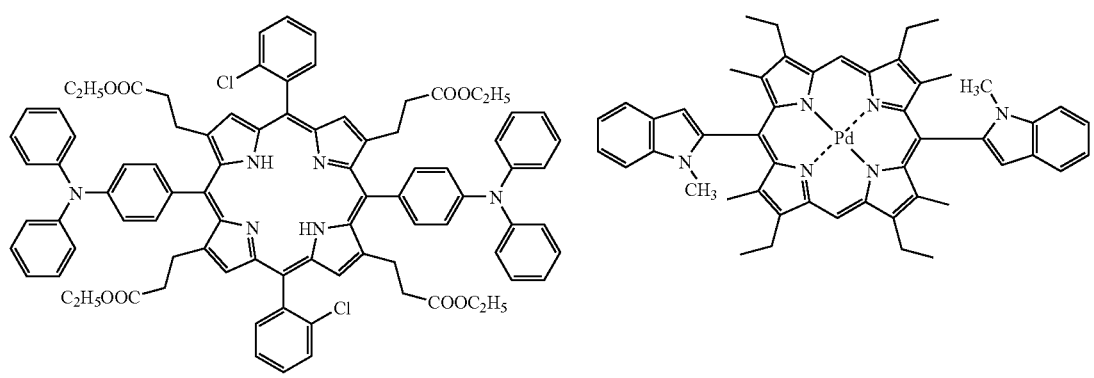
No. 16
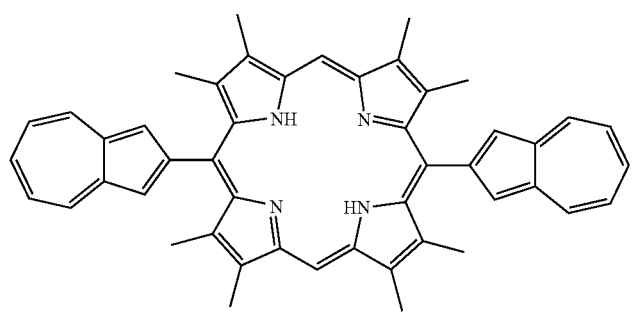

-continued
No. 17
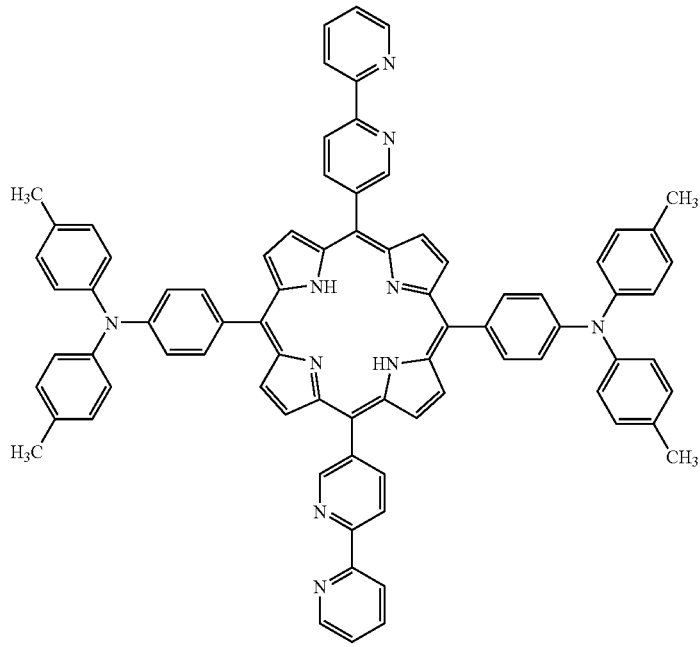
No. 18
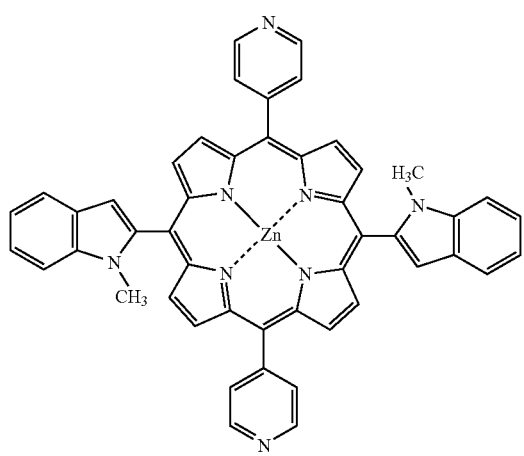
No. 19
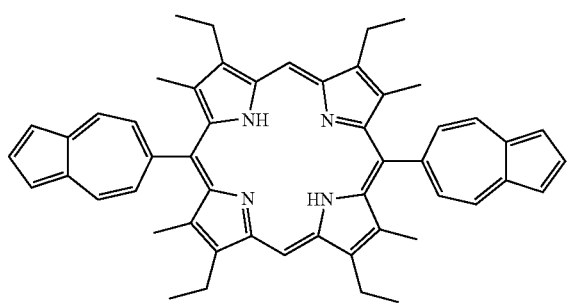
No. 20
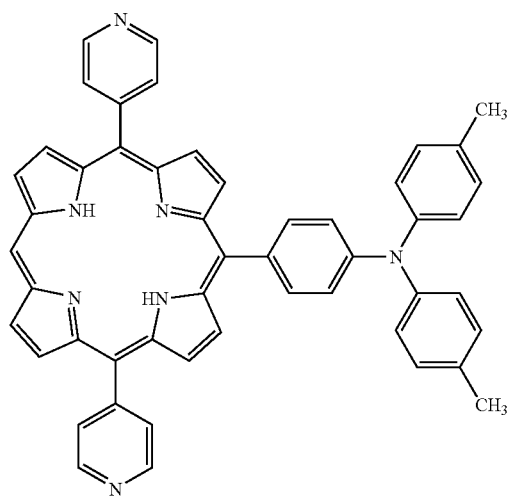
No. 21
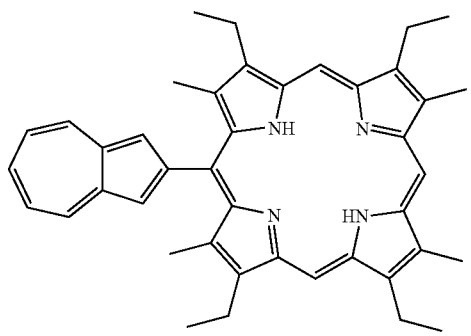

-continued
No. 22
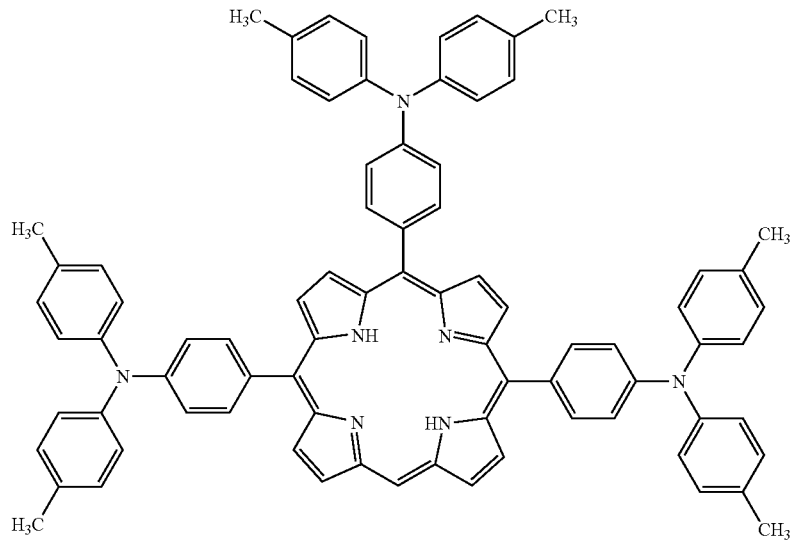
No. 23
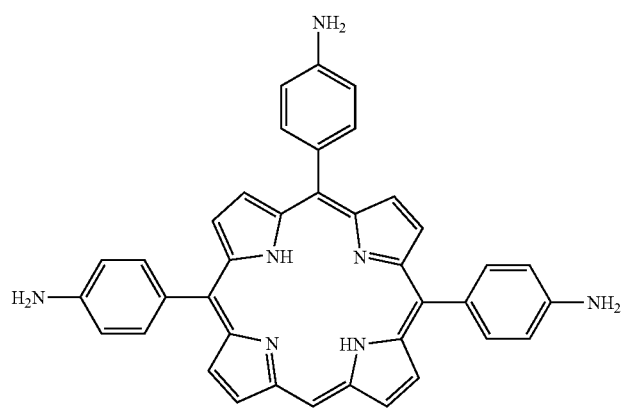
No. 24
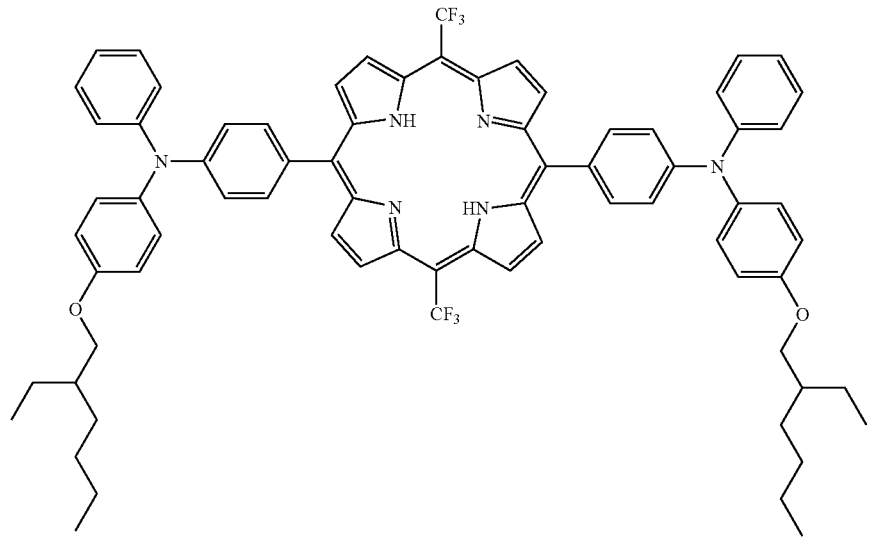

No. 25
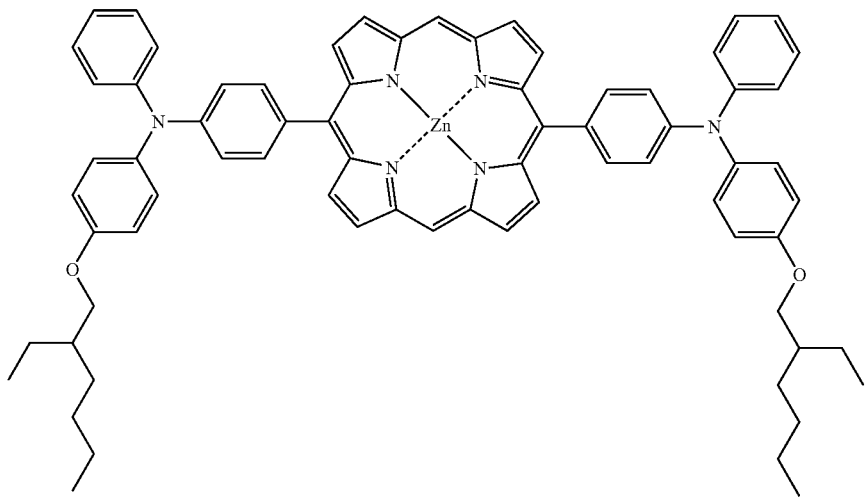
No. 26
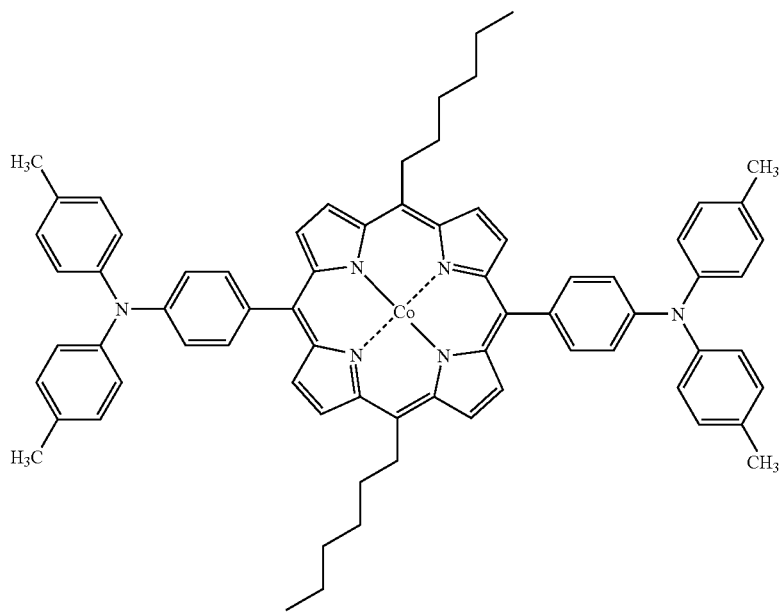
No. 27
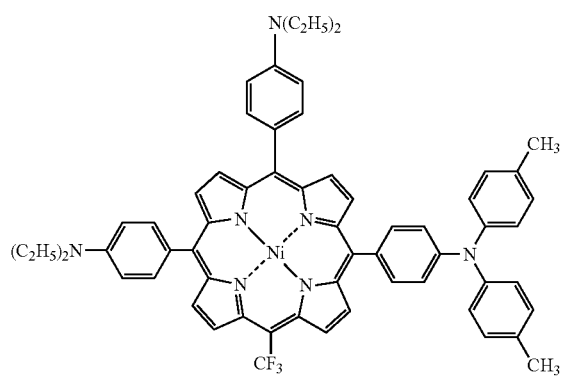

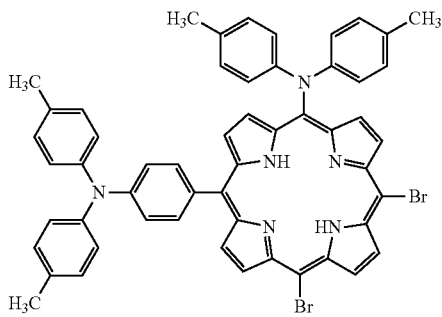

No. 28

Two-Photon Absorption Material According to Second Embodiment

A two-photon absorption material according to a second embodiment is represented by General Formula (I) in which at least one of $X_1$ and $X_3$ is a phenyl group having, as a substitutent, an alkyl group, an alkoxy group, a trifluoromethyl group, a nitro group, a cyano group or a carboxylic acid ester group, or a substituted or unsubstituted pyridinyl group, with the proviso that when only one of $X_1$ and $X_3$ is the phenyl group or the pyridinyl group, the other is a hydrogen atom or a halogen atom; and at least one of $X_2$ and $X_4$ is a substituent represented by (a) or (b) given below, with the proviso that when only one of $X_2$ and $X_4$ is the substitutent, the other is preferably a hydrogen atom or a halogen atom.

Specifically, the two-photon absorption material according to a second embodiment is two-photon absorption materials represented by the following General Formula (I)':

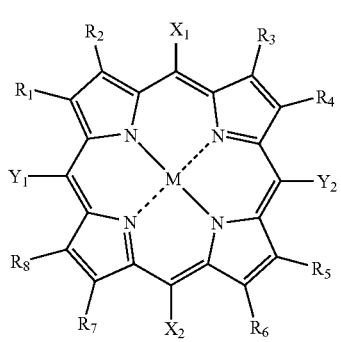

General Formula (I)' where $R_1$ to $R_8$ each represent a hydrogen atom, a halogen atom, a carboxyl group, a carboxylic acid ester group, a substituted or unsubstituted aryl group or a substituted or unsubstituted alkyl group; at least one of $X_1$ and $X_2$ is a phenyl group having, as a substituent, an alkyl group, an alkoxy group, a trifluoromethyl group, a nitro group, a cyano group or a carboxylic acid ester group, or a substituted or unsubstituted pyridinyl group, with the proviso that when only one of $X_1$ and $X_2$ is the phenyl group or the pyridinyl group, the other is a hydrogen atom or a halogen atom; at least one of $Y_1$ and $Y_2$ is a substituent represented by (a) or (b) given below, with the proviso that when only one of $Y_1$ and $Y_2$ is the substituent, the other is a hydrogen atom or a halogen atom; and M represents two hydrogen atoms or a divalent, trivalent or tetravalent metal atom which may have an oxygen atom or a halogen atom,

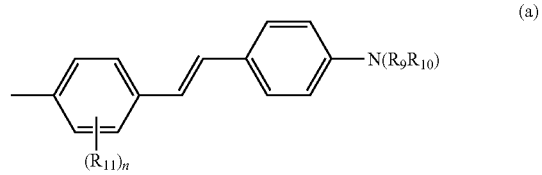

(a)

where $R_{11}$ represents an alkyl group or an alkoxy group, $R_9$ and $R_{10}$ each represent a hydrogen atom, an alkyl group or a substituted or unsubstituted phenyl group, and n is an integer of 1 or 2,

(b)

where $R_{12}$ and $R_{13}$ each represent a hydrogen atom, an alkyl group or a substituted or unsubstituted phenyl group.

Another two-photon absorption material according to a second embodiment is represented by the following General Formula (II):

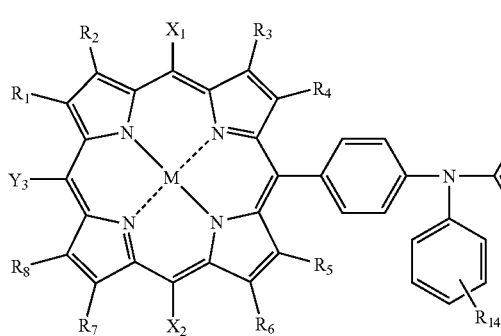
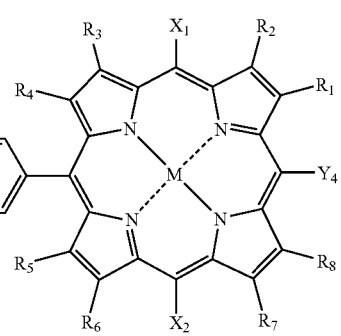

General Formula (II)

where $R_1$ to $R_8$ each represent a hydrogen atom, a halogen atom, a carboxyl group, a carboxylic acid ester group, a substituted or unsubstituted aryl group or a substituted or unsubstituted alkyl group; $R_{14}$ represents an alkyl group, an alkoxy group or a hydrogen atom; at least one of $X_1$ and $X_2$ is a phenyl group having, as a substituent, an alkyl group, an alkoxy group, a trifluoromethyl group, a nitro group, a cyano group or a carboxylic acid ester group, or a substituted or unsubstituted pyridinyl group, with the proviso that when only one of $X_1$ and $X_2$ is the phenyl group or the pyridinyl group, the other is a hydrogen atom or a halogen atom; $Y_3$ and $Y_4$ each represent a substituent represented by (a) or (b) given above, a hydrogen atom or a halogen atom; and M represents two hydrogen atoms or a divalent, trivalent or tetravalent metal atom which may have an oxygen atom or a halogen atom.

Two-photon absorption materials represented by the following General Formula (III):

where $R_1$ to $R_8$ each represent a hydrogen atom, a halogen atom, a carboxyl group, a carboxylic acid ester group, a substituted or unsubstituted aryl group or a substituted or unsubstituted alkyl group; $R_{15}$ represents an alkyl group or a hydrogen atom; at least one of $X_1$ and $X_2$ is a phenyl group having, as a substituent, an alkyl group, an alkoxy group, a trifluoromethyl group, a nitro group, a cyano group or a carboxylic acid ester group, or a substituted or unsubstituted pyridinyl group, with the proviso that when only one of $X_1$ and $X_2$ is the phenyl group or the pyridinyl group, the other is a hydrogen atom or a halogen atom; $Y_5$ and $Y_6$ each represent a substituent represented by (a) or (b) given above, a hydrogen atom or a halogen atom; and M represents two hydrogen atoms or a divalent, trivalent or tetravalent metal atom which may have an oxygen atom or a halogen atom.

Next will be given porphyrin derivatives represented by General Formulas (I)', (II) and (III).

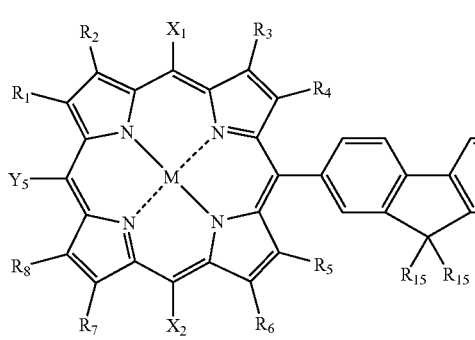
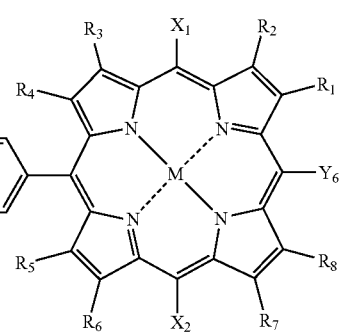

General Formula (III)

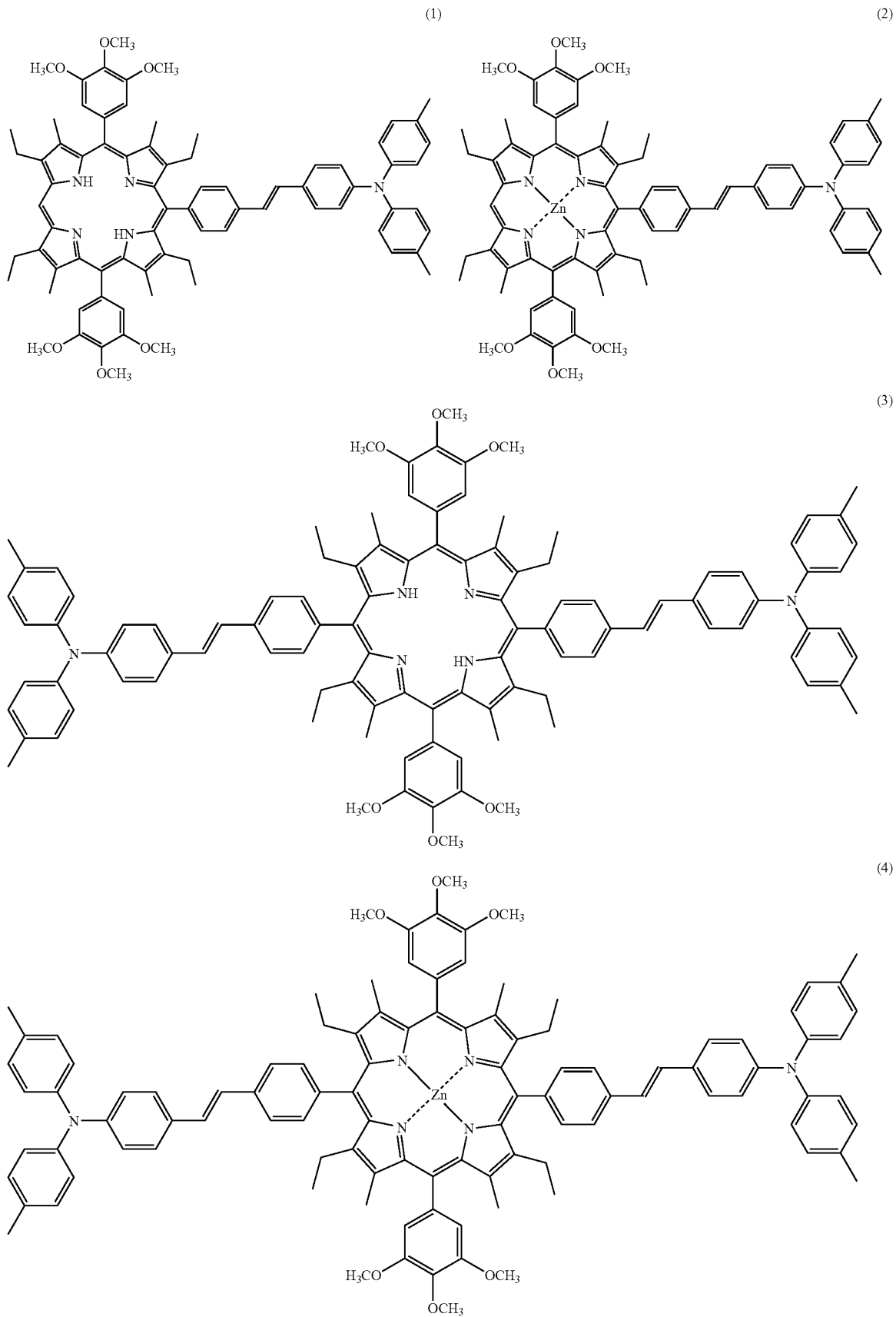

-continued
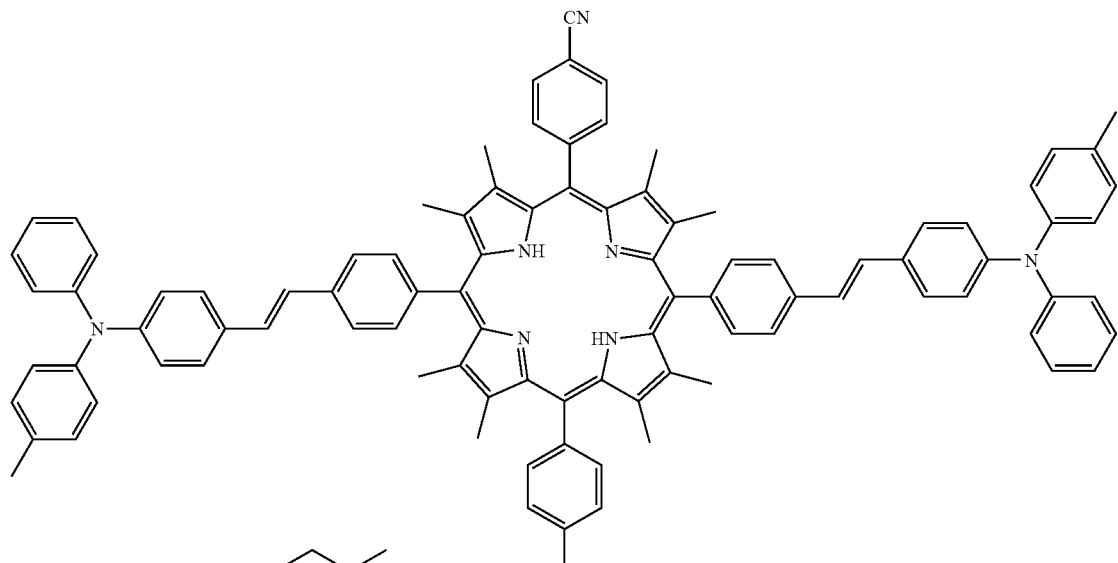
(5)
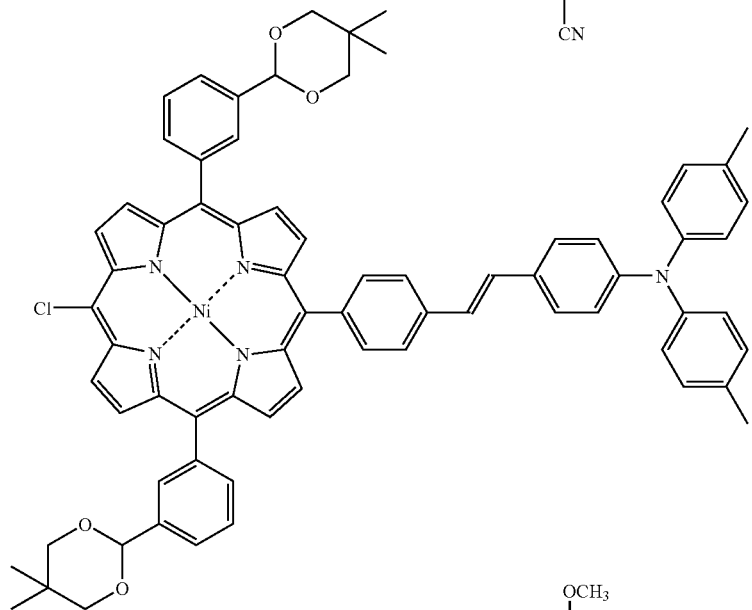
(6)
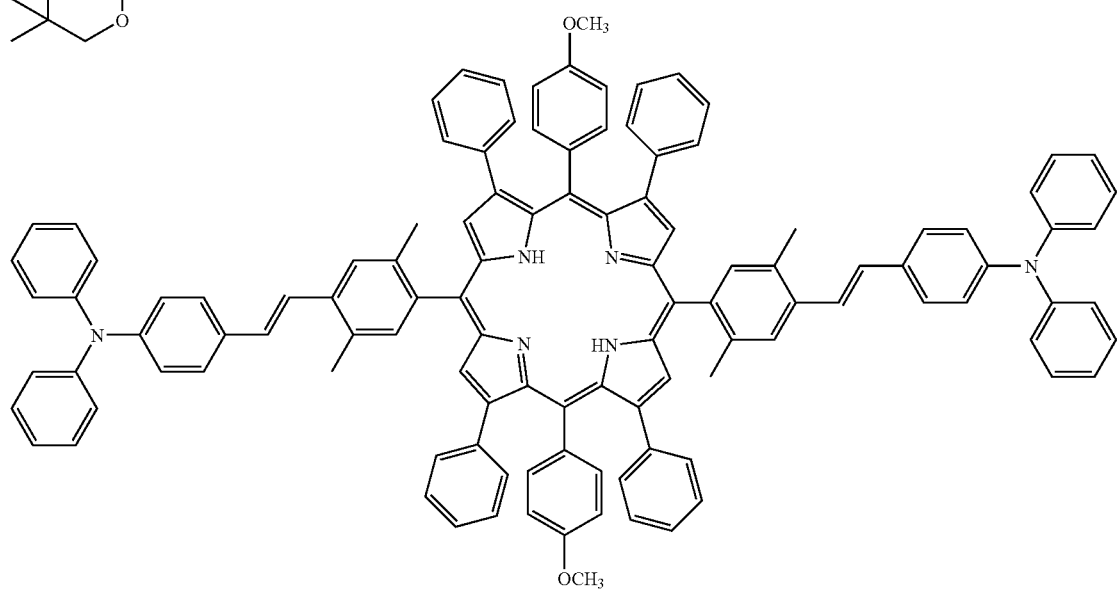
(7)

-continued
(8)
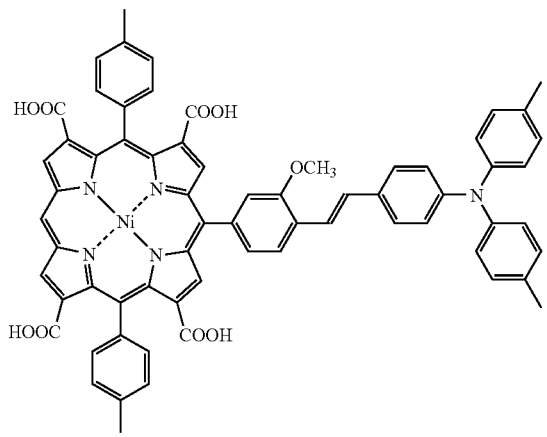
(9)
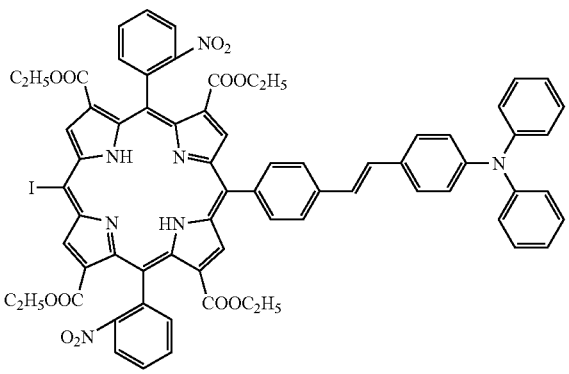
(10)
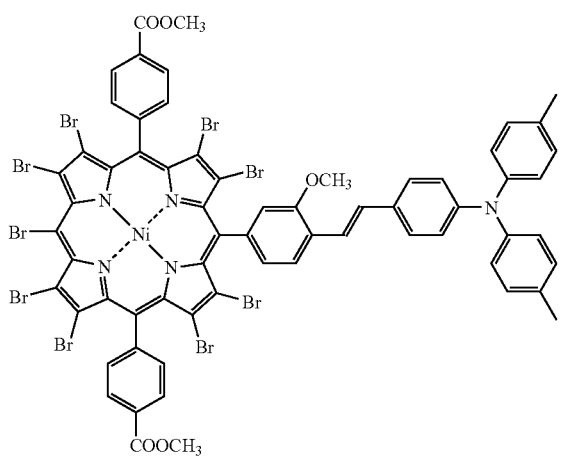
(11)
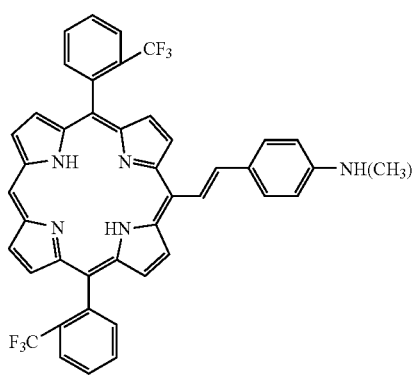
(12)
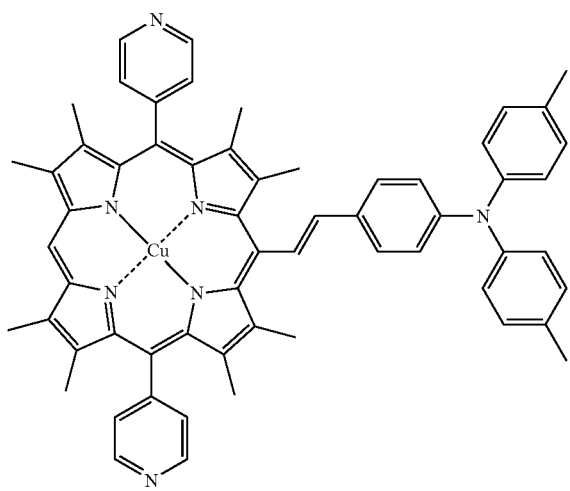

-continued
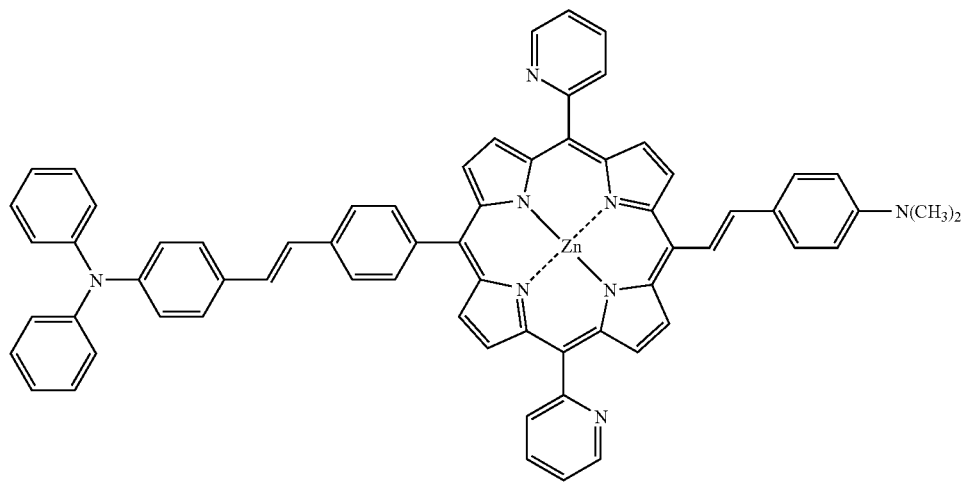
(13)
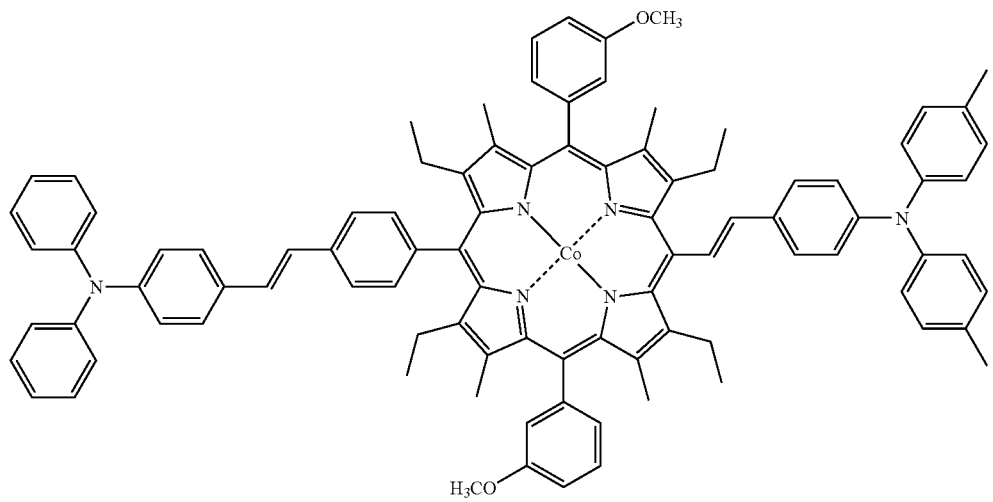
(14)
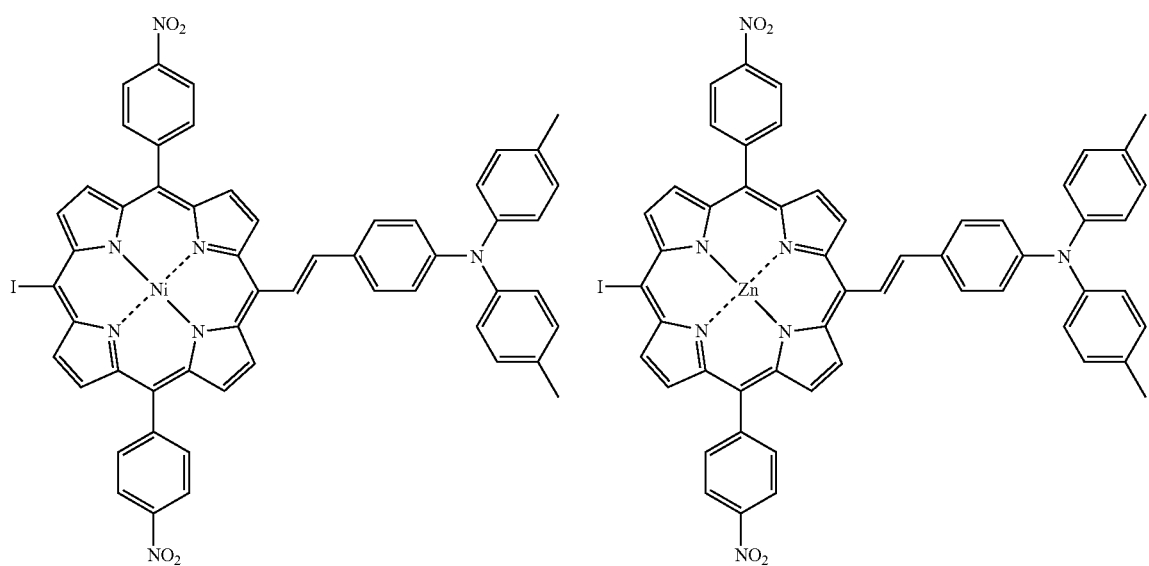
(15)  (16)

(17)
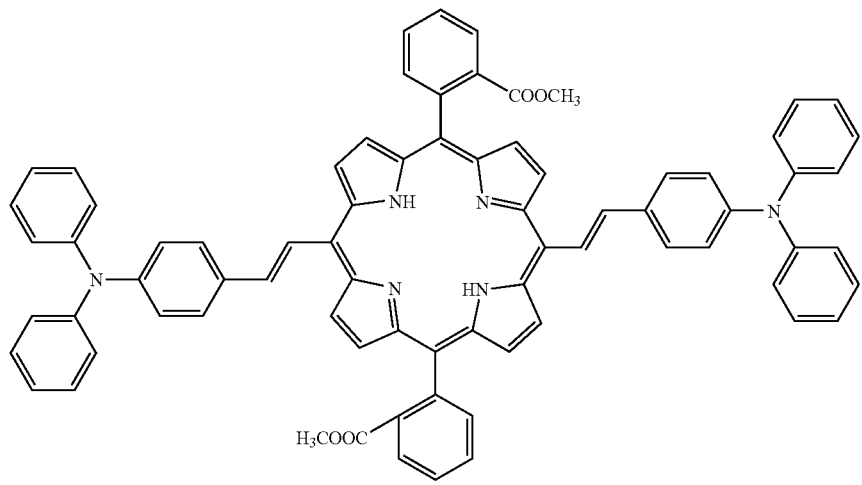
(18)
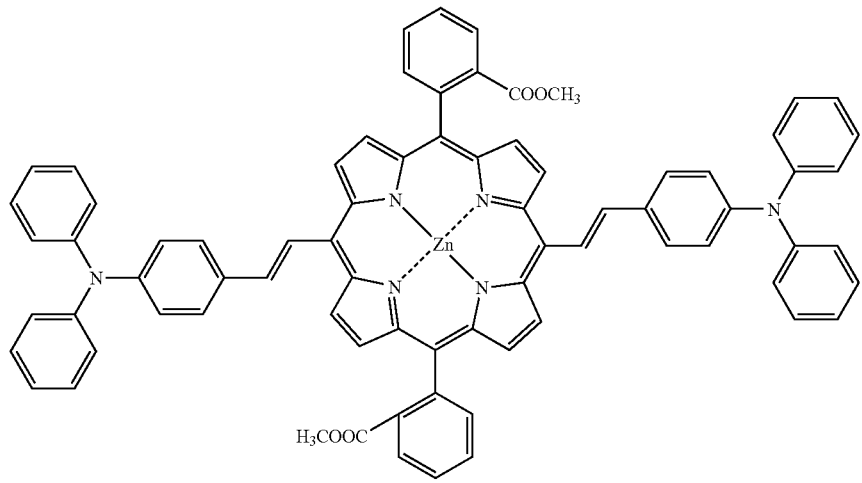
(19)
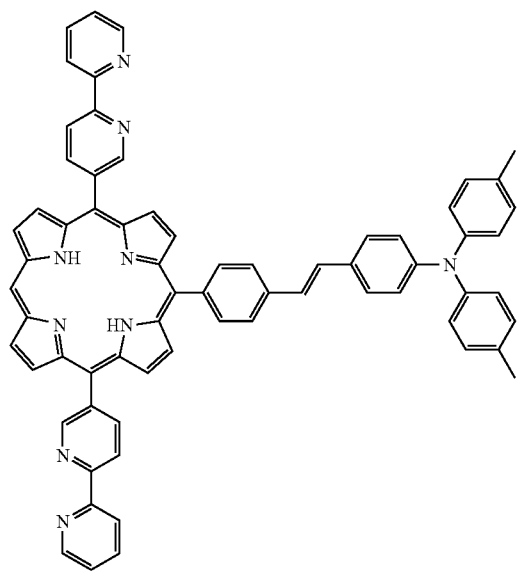
(20)
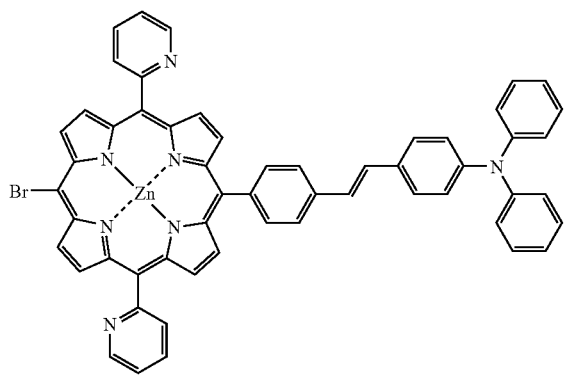

(21)
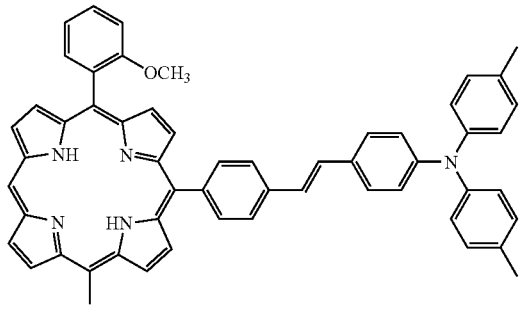
(22)
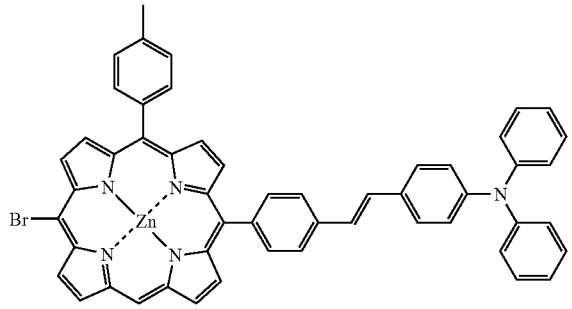
(23)
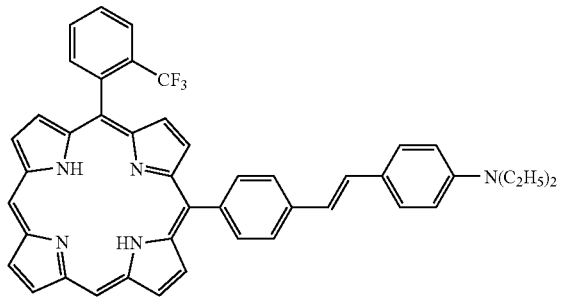
(24)
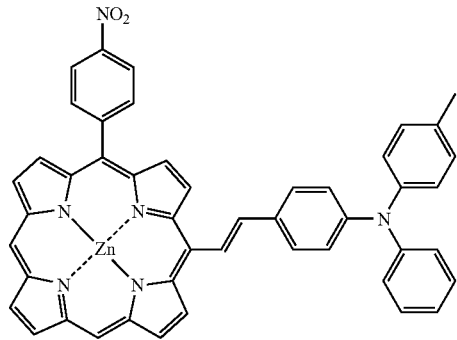
(25)
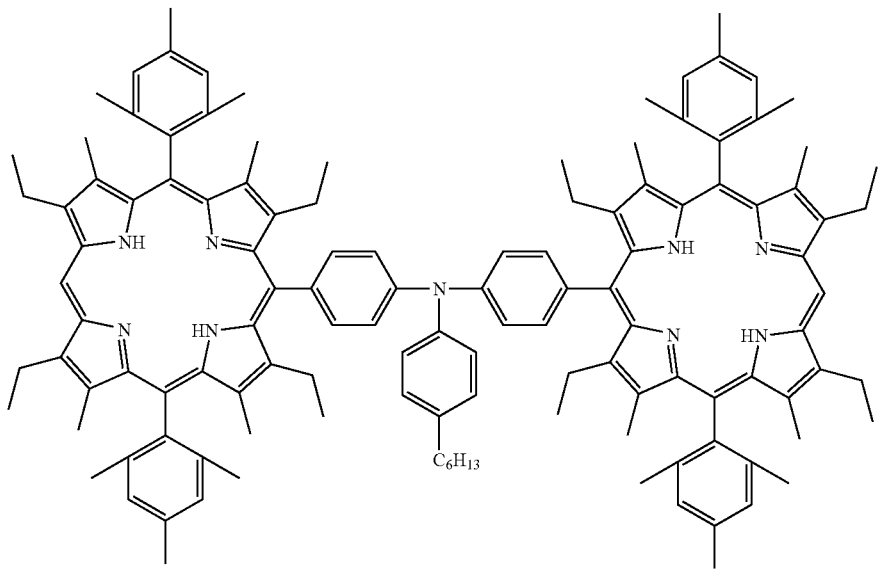

-continued
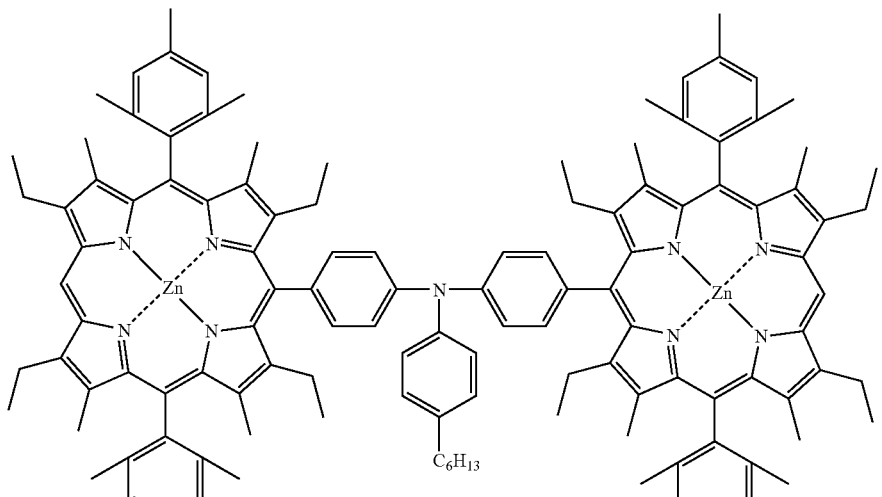
(26)
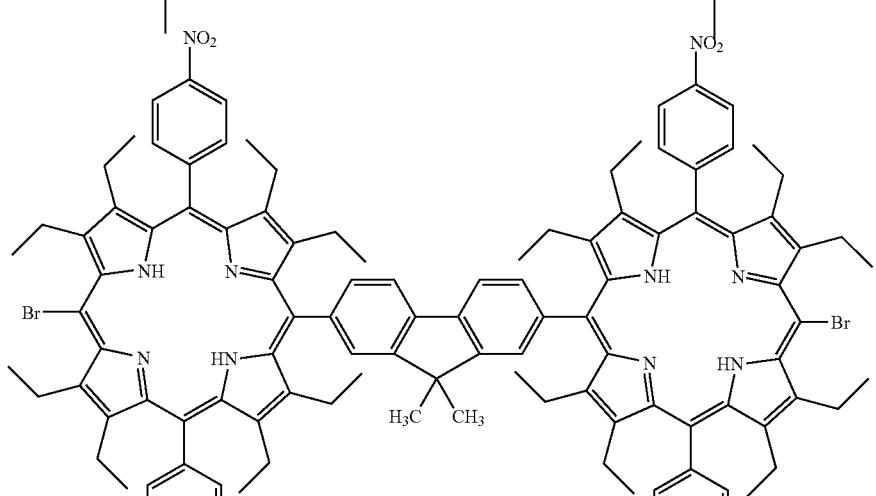
(27)
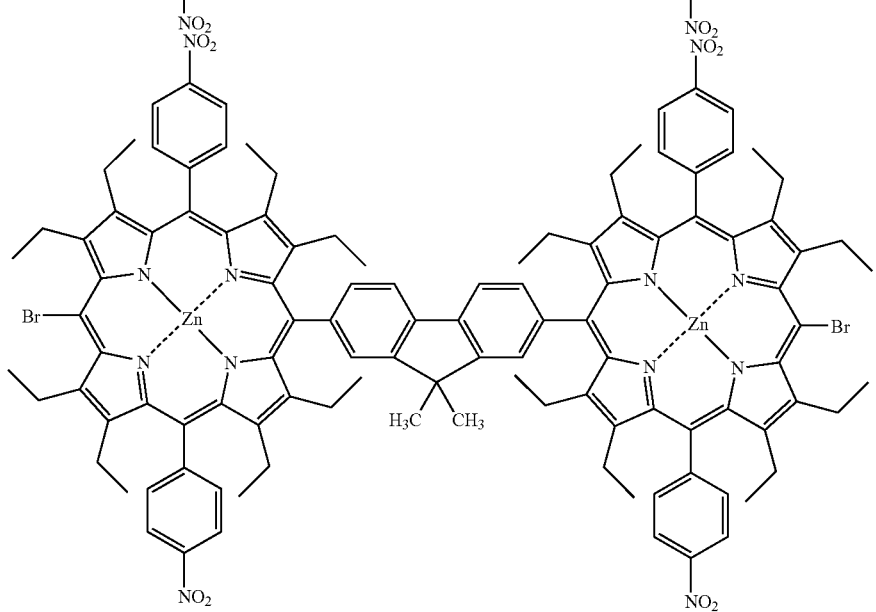
(28)

-continued
(29)
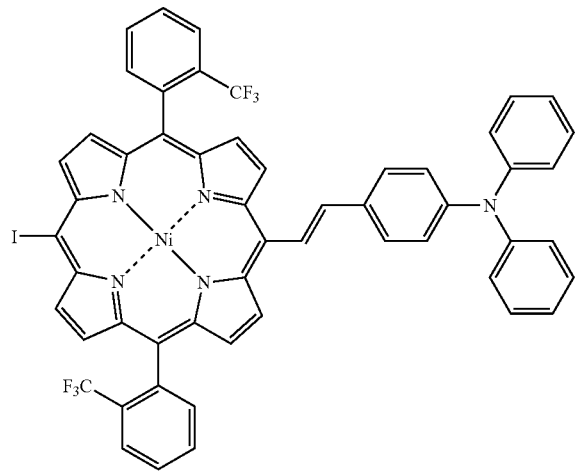
(30)
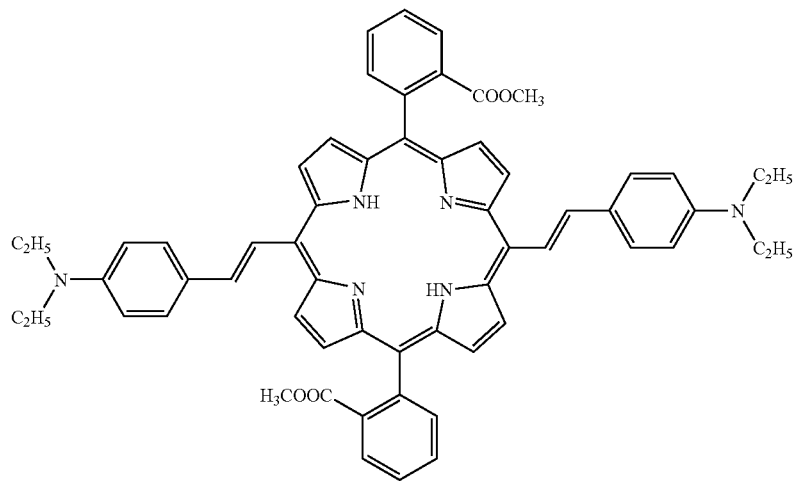
(31)
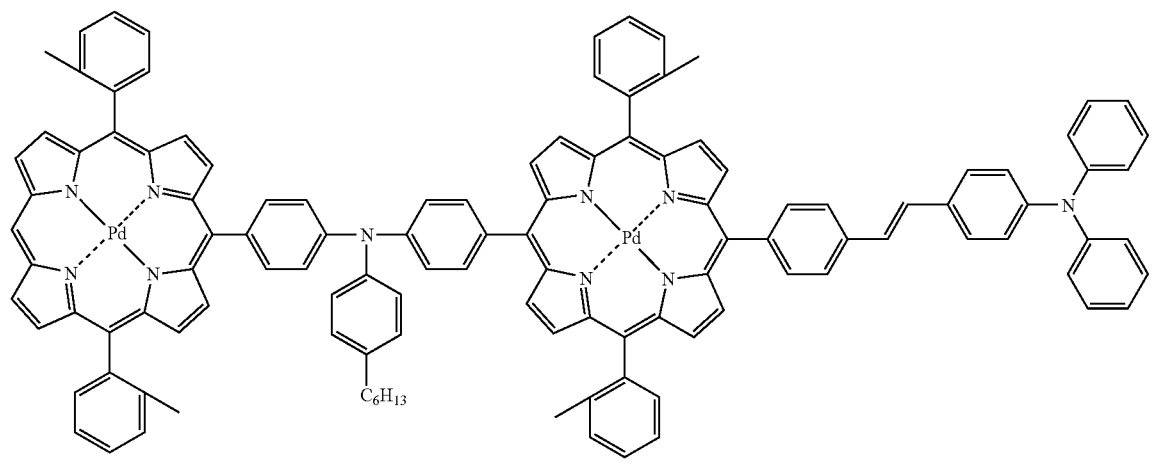

-continued
(32)
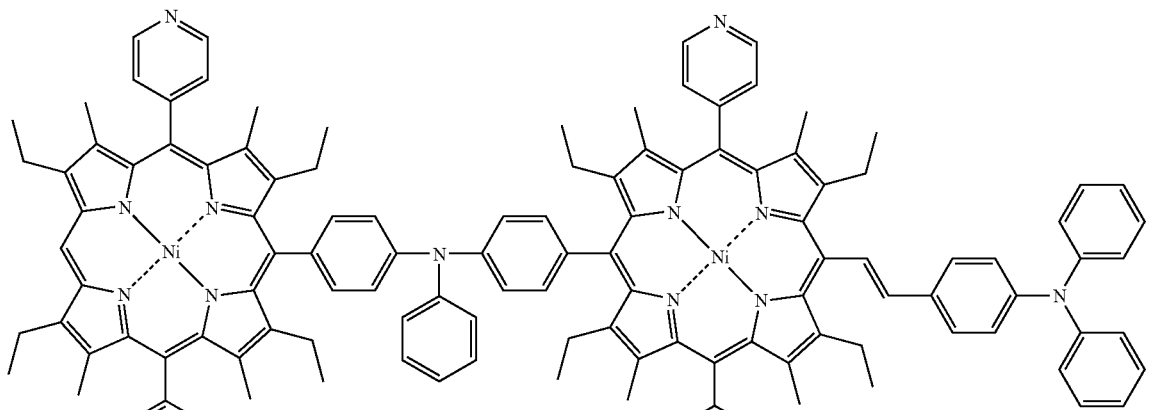
(33)
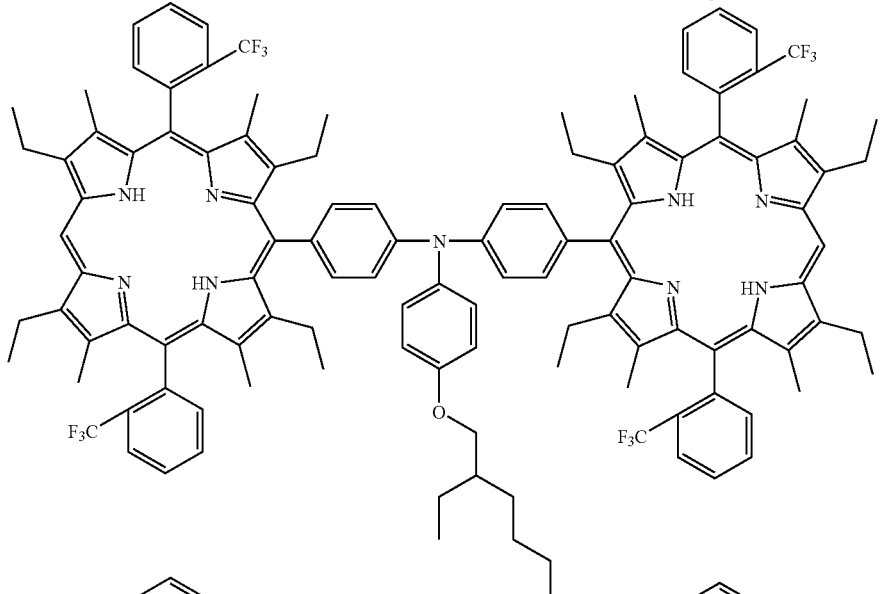
(34)
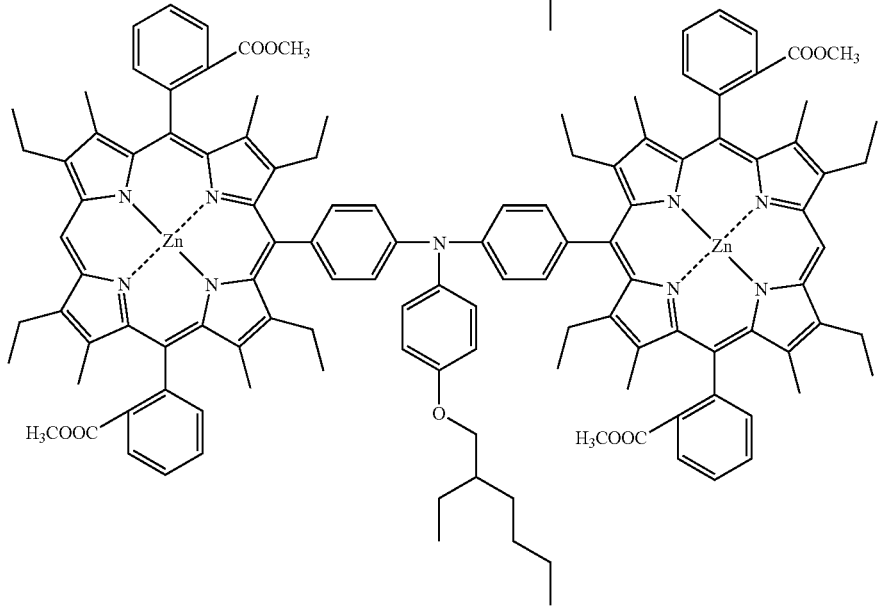

(35)
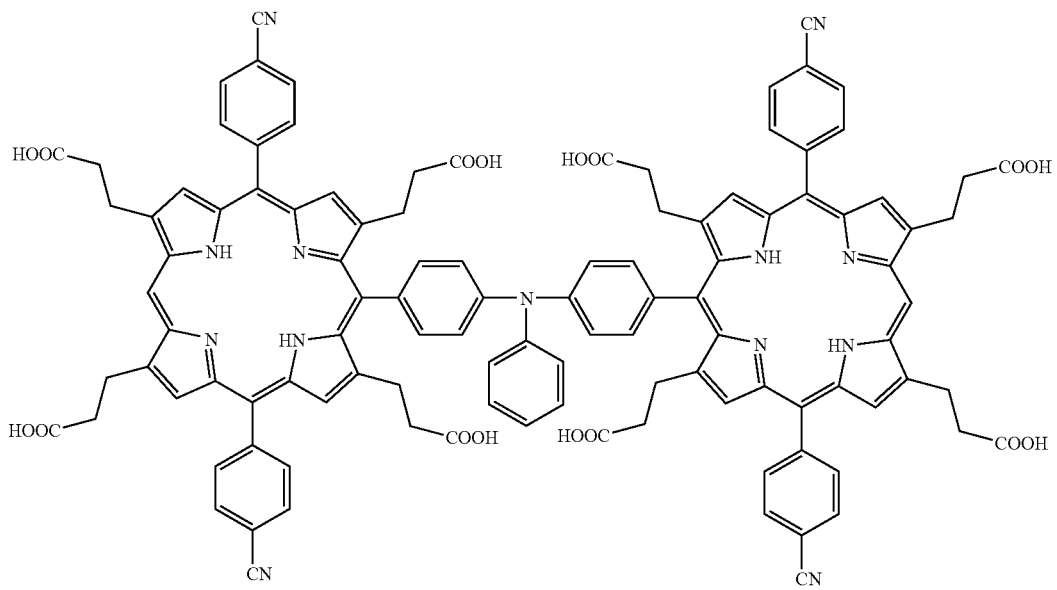
(36)
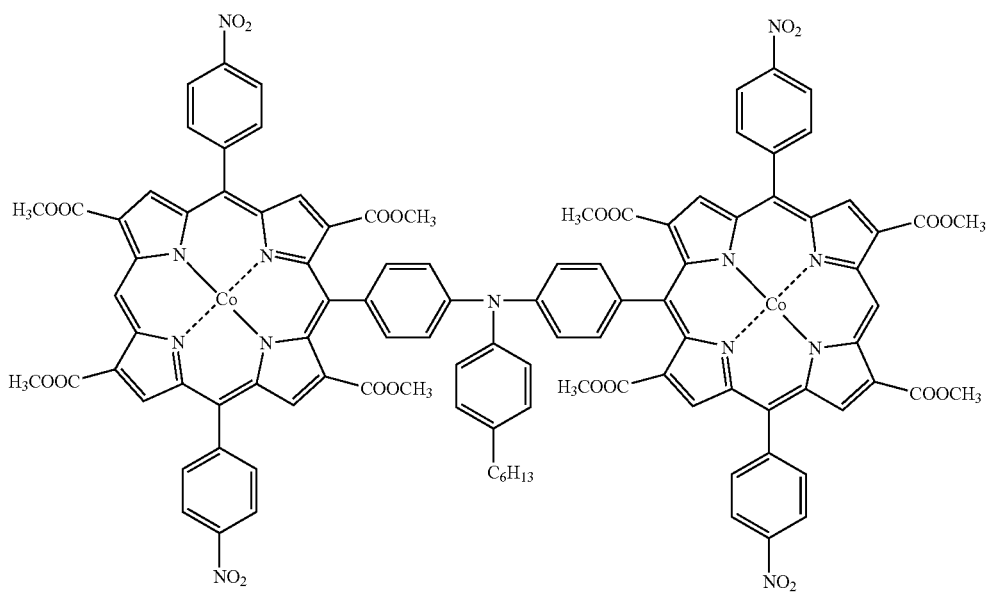
(37)
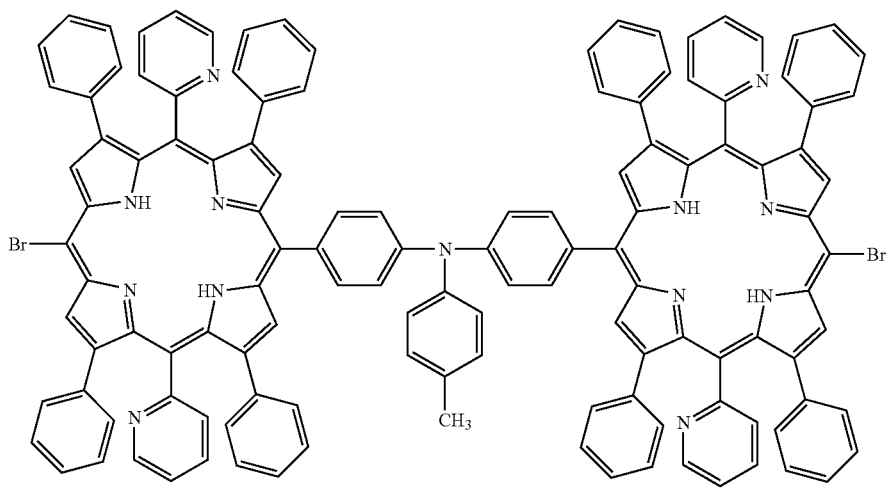

(38)
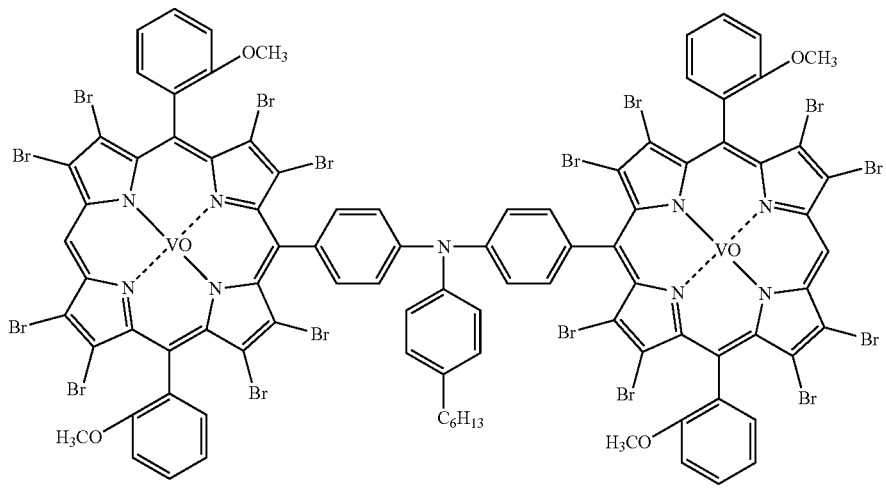
(39)
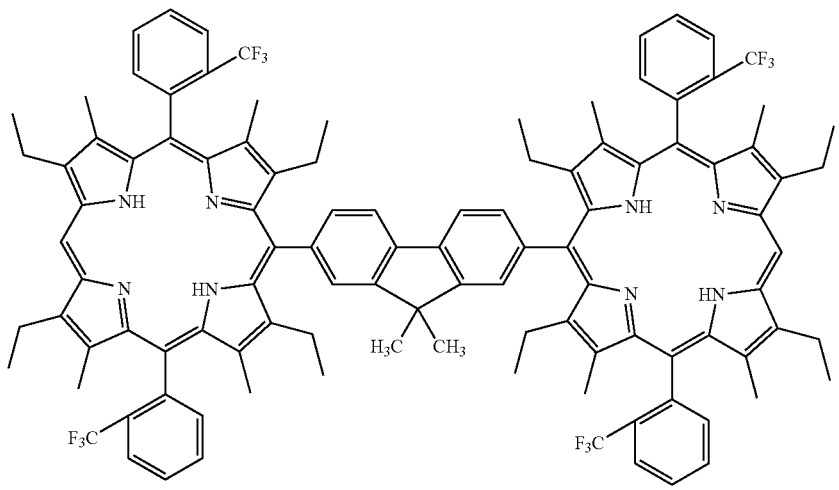
(40)
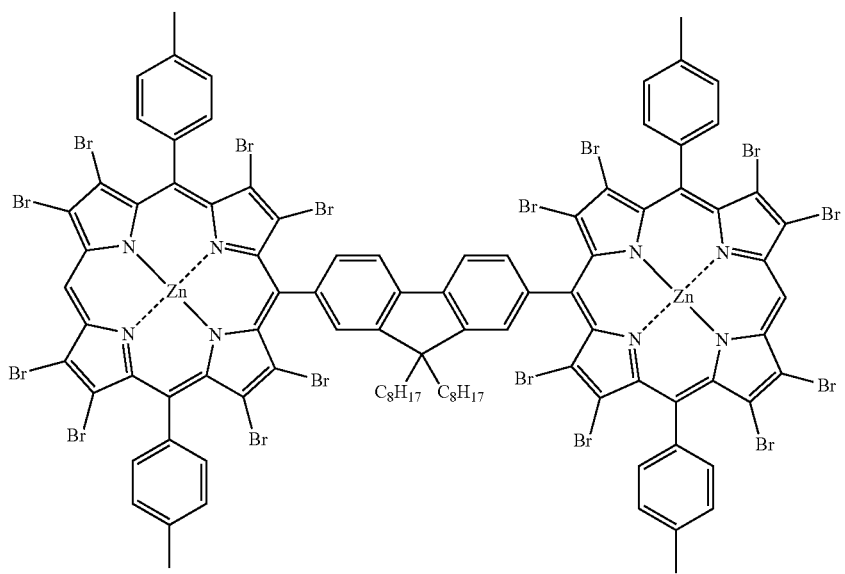

-continued
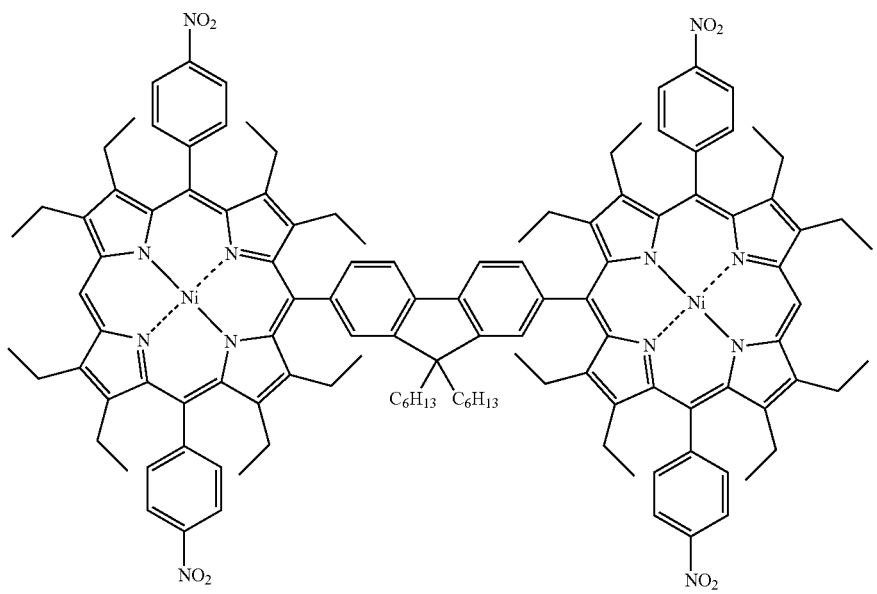
(41)
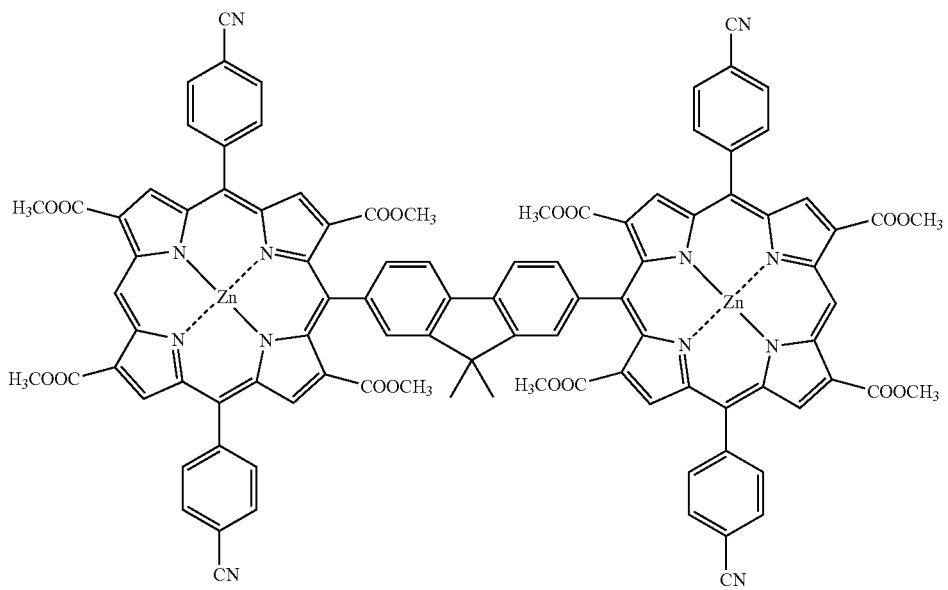
(42)
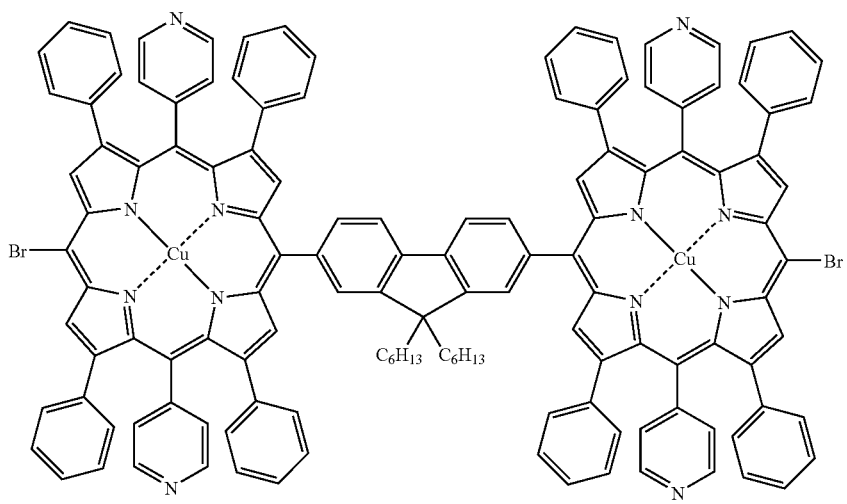
(43)

-continued
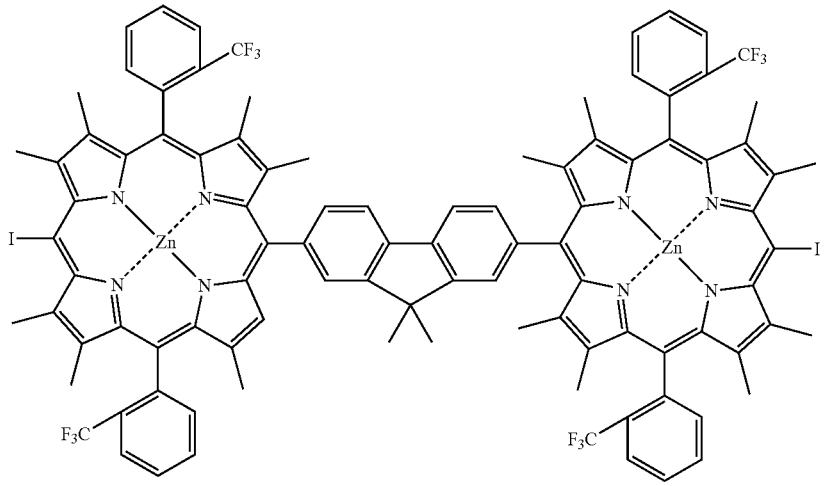
(44)
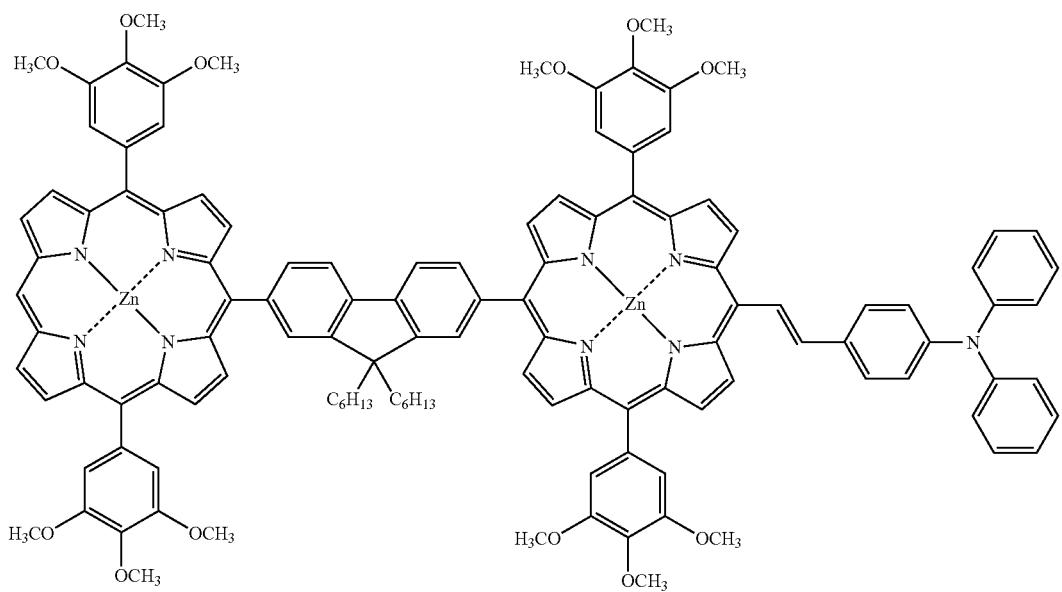
(45)
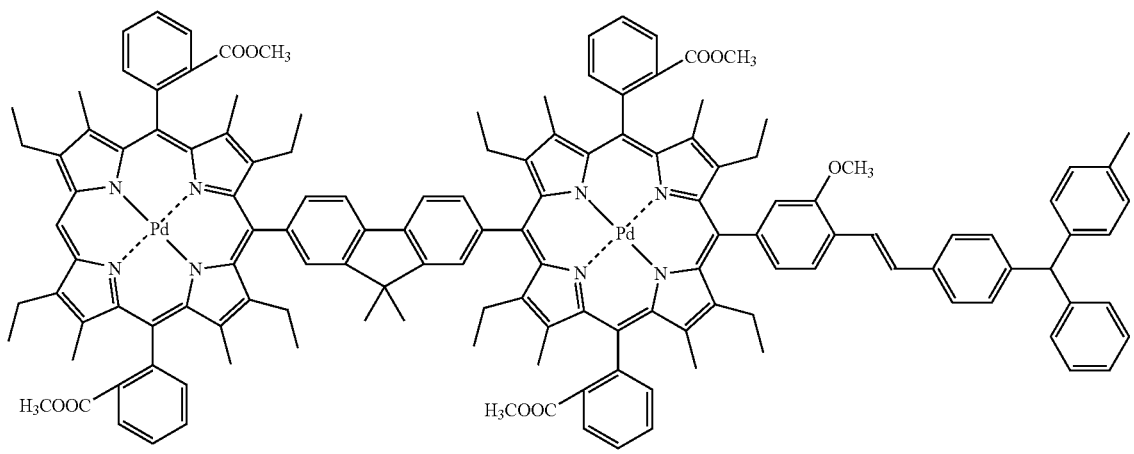
(46)

(47)
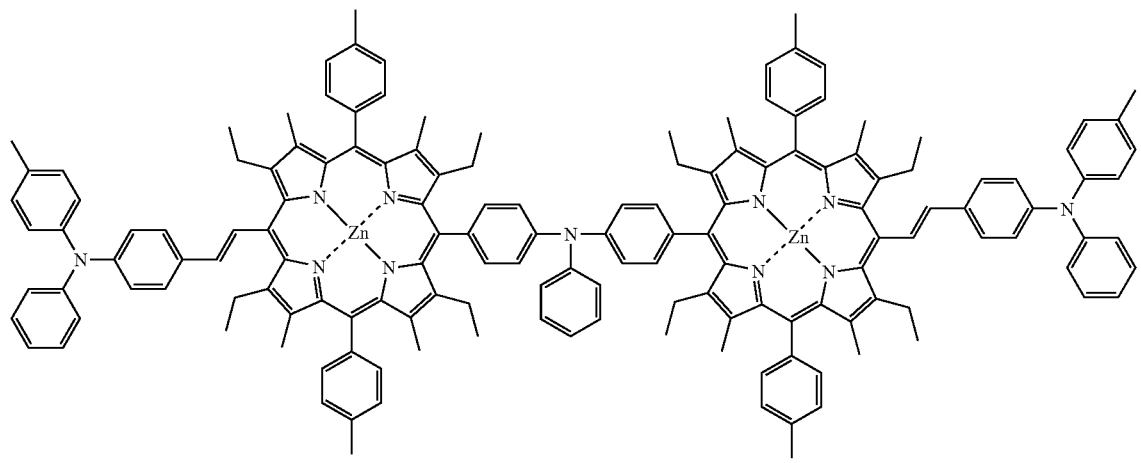
(48)
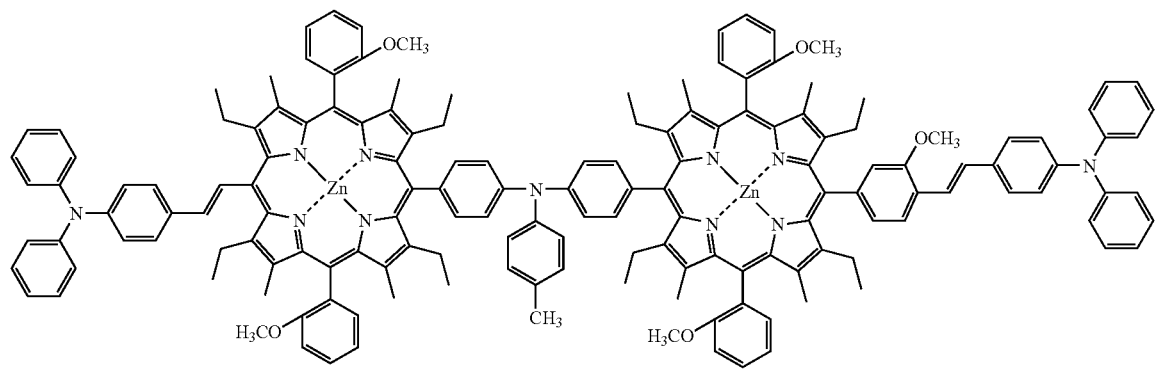
(49)
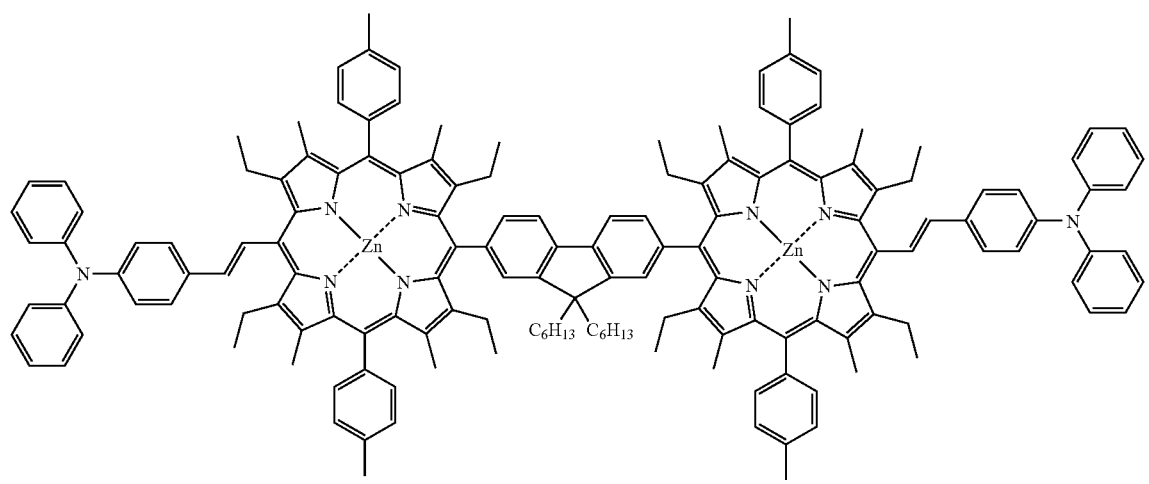

(50)
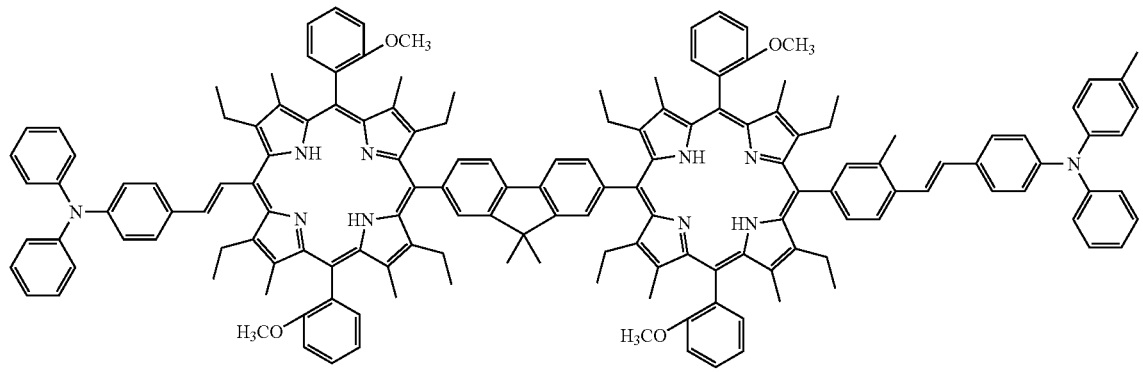
(51)
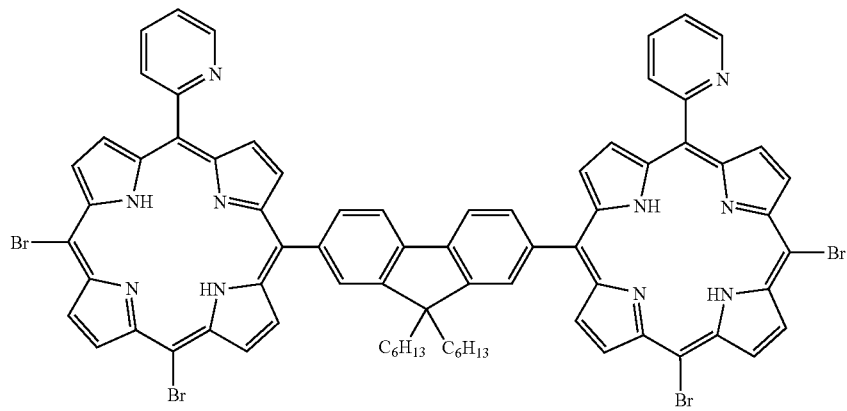
(52)
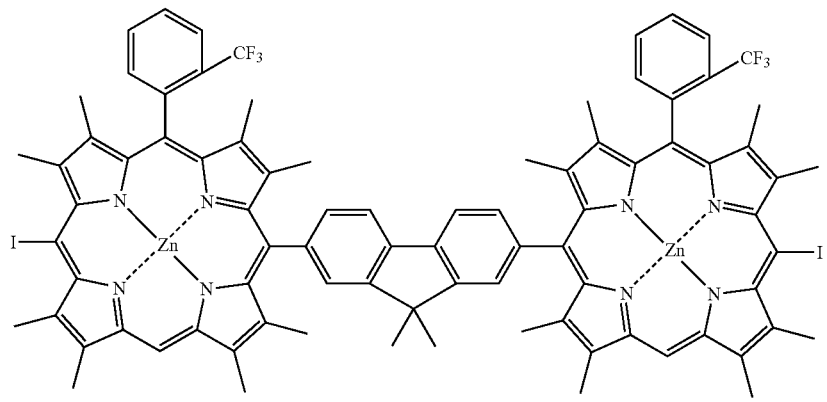
(53)
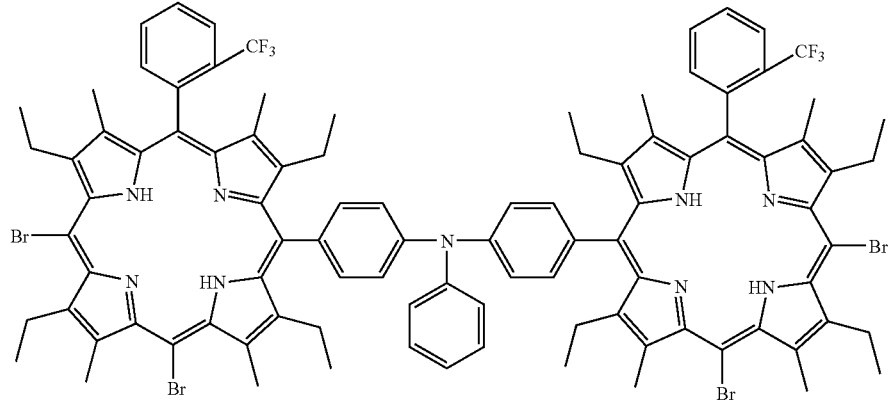

-continued
(54)
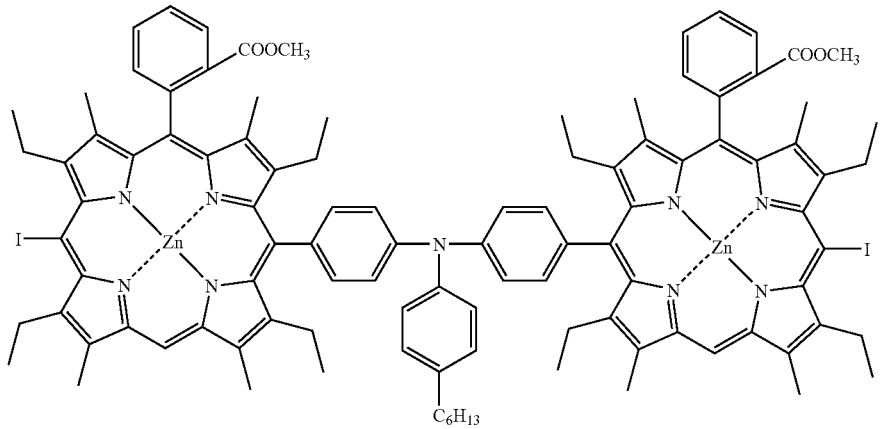
(55)
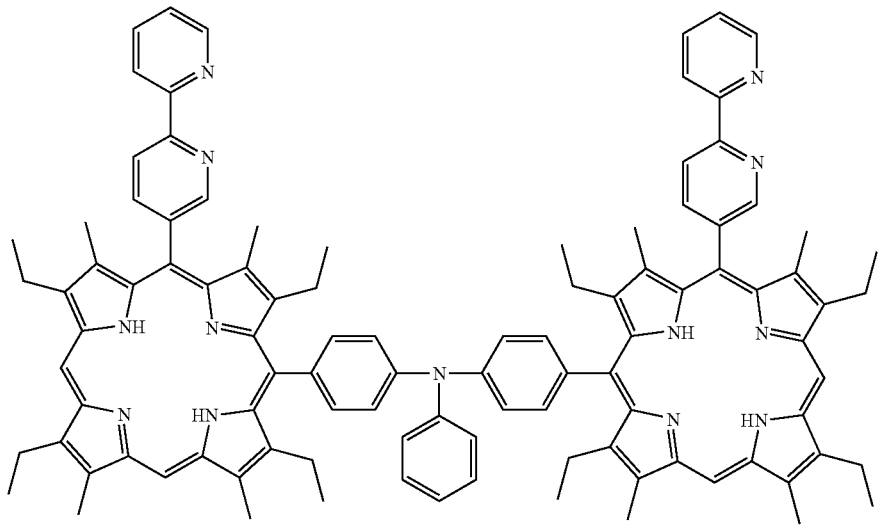
(56)
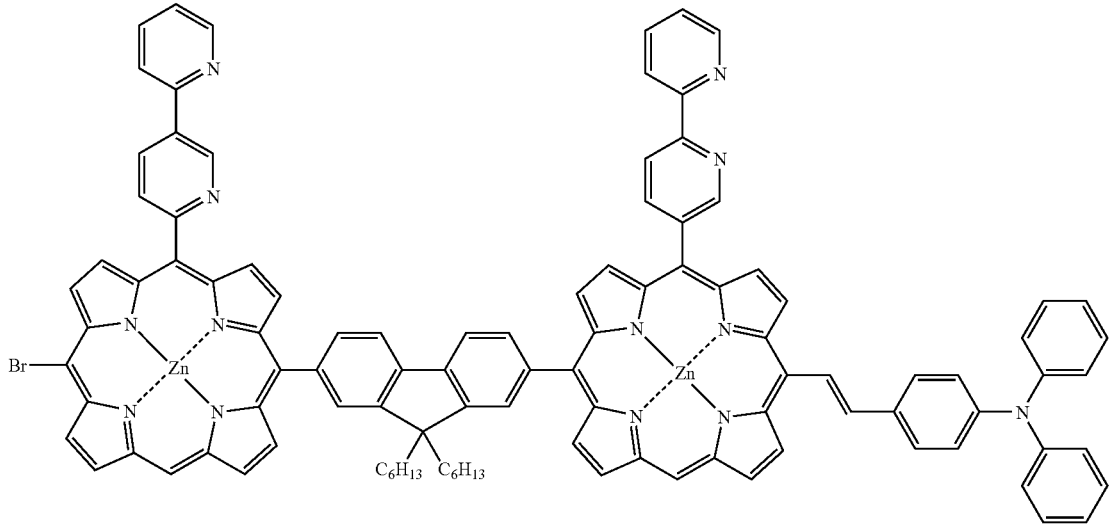

-continued
(57)
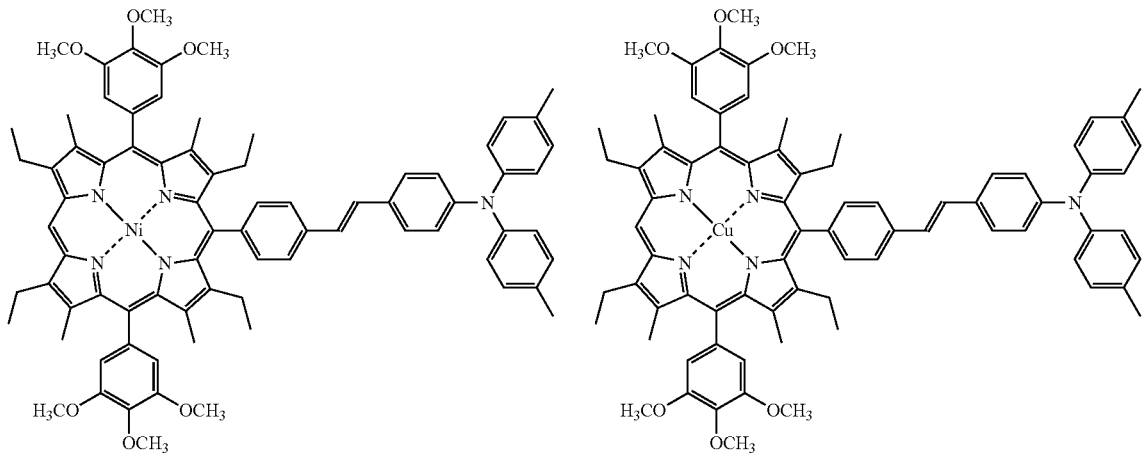
(58)
(59)
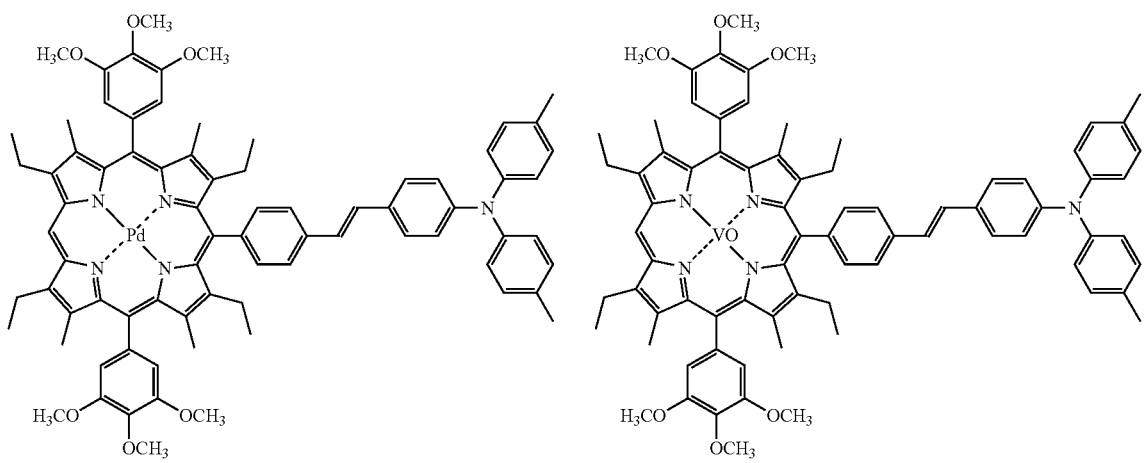
(60)
(61)
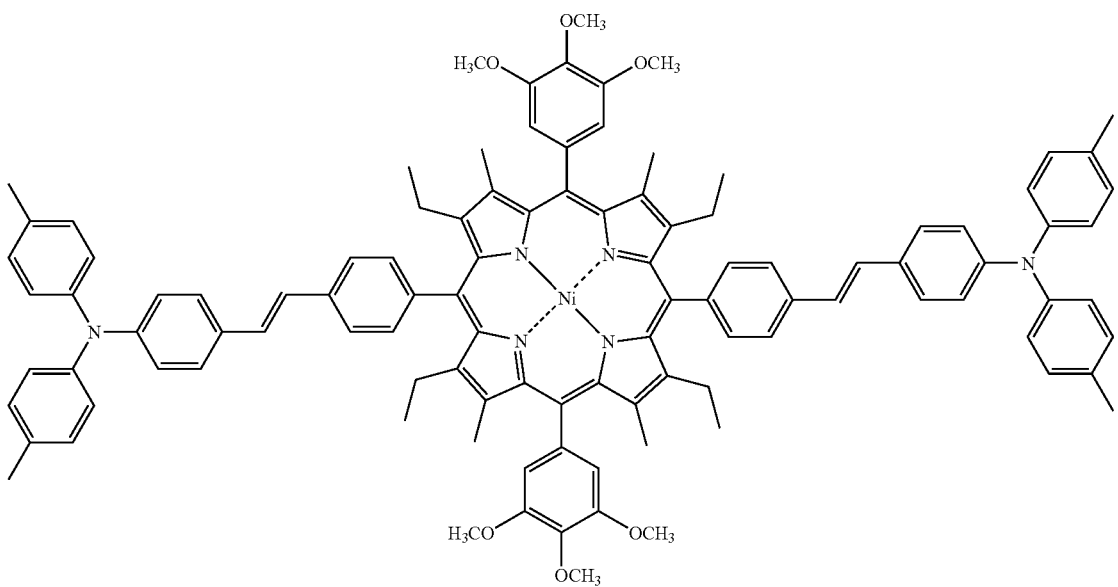

(62)
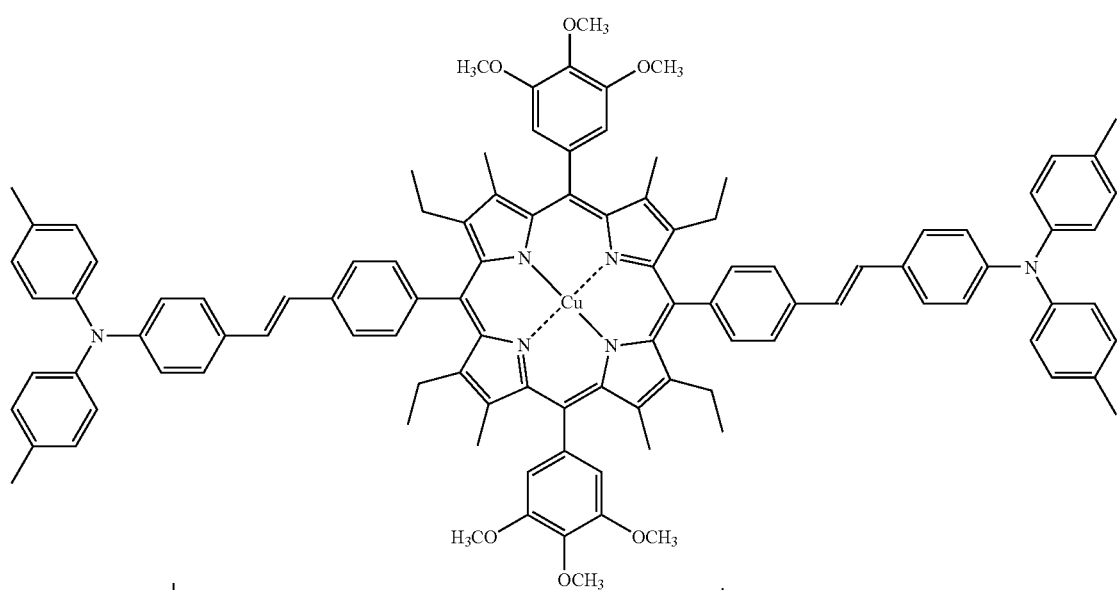
(63)
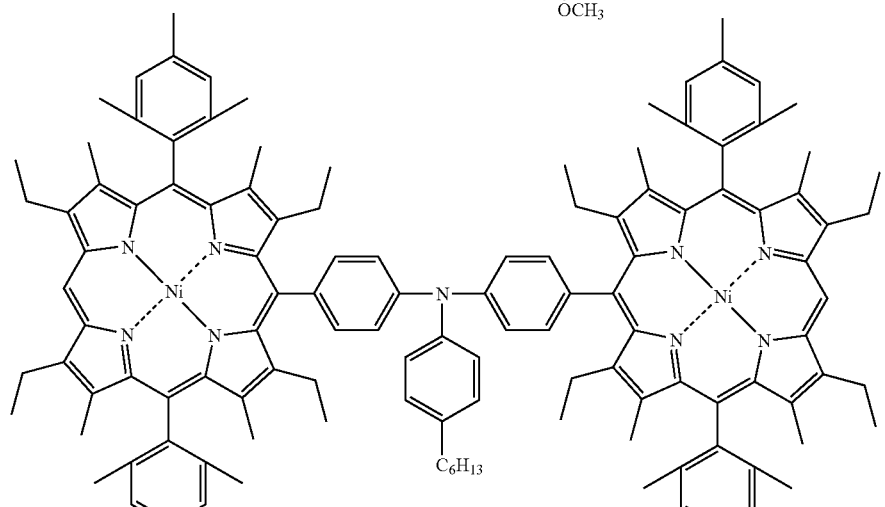
(64)
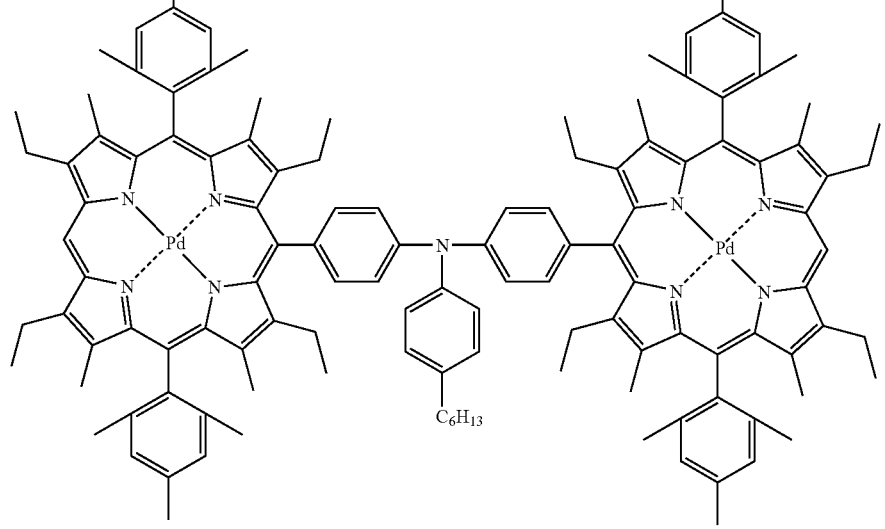

-continued
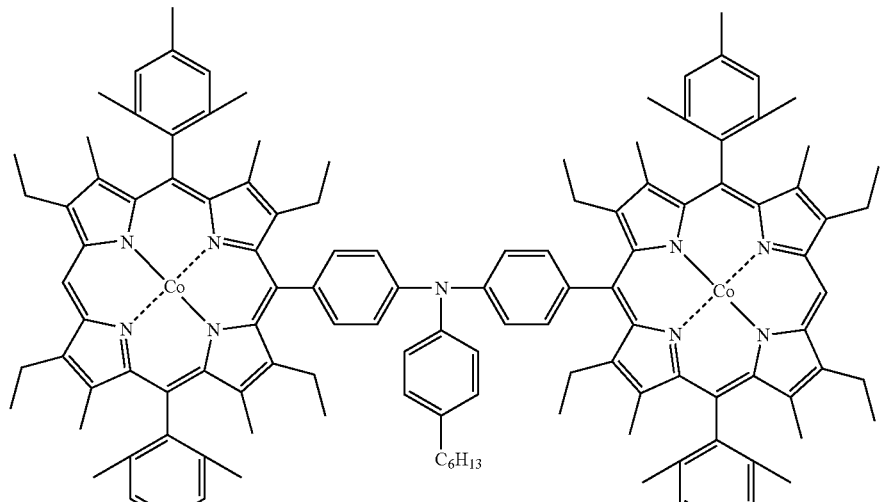
(65)
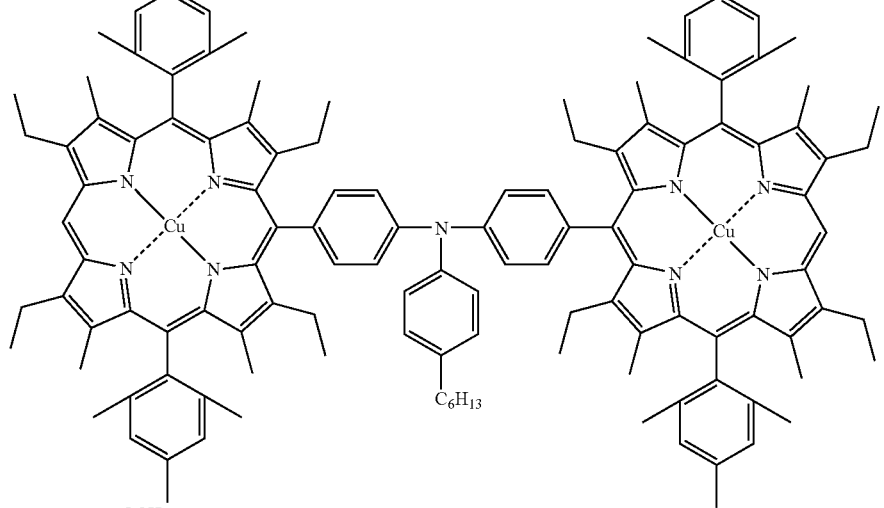
(66)
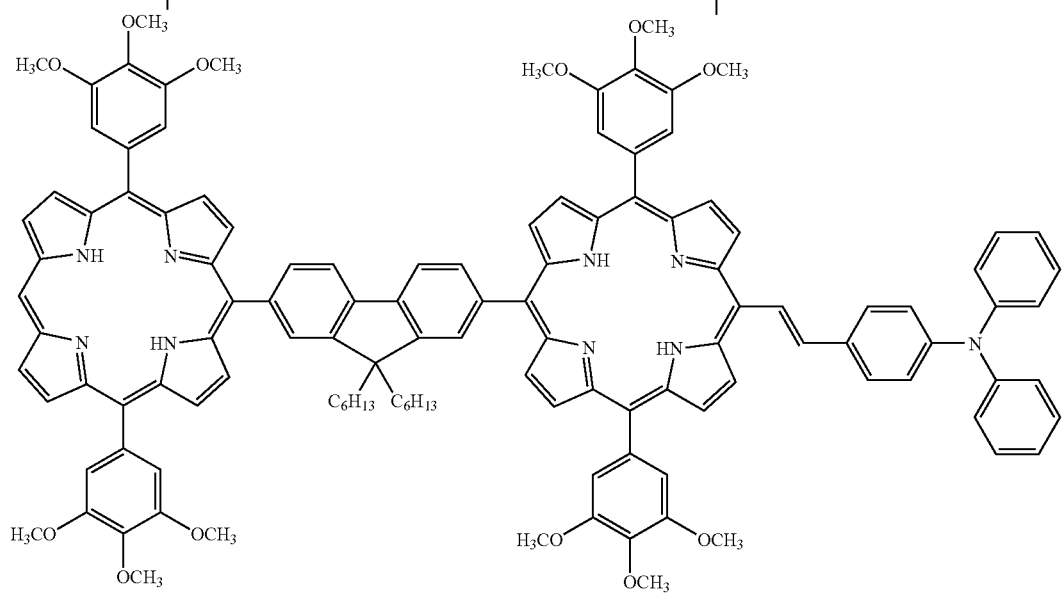
(67)

-continued
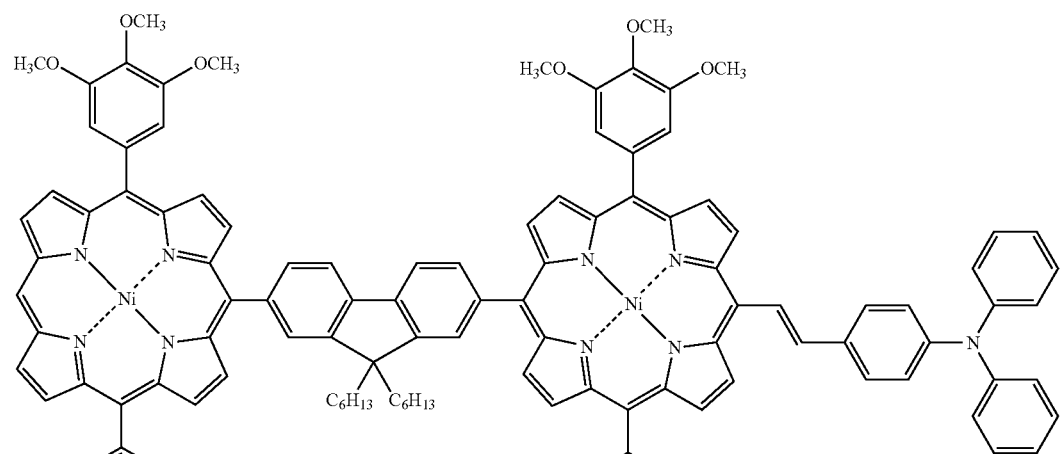
(68)
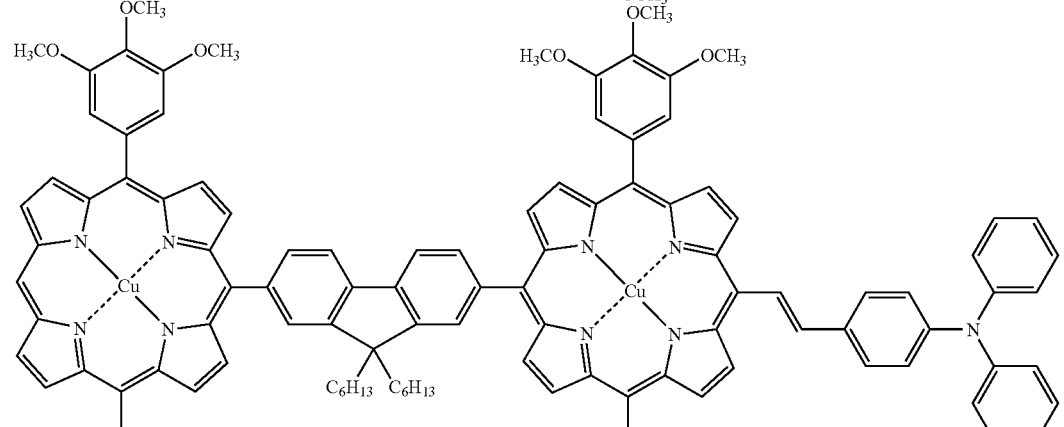
(69)
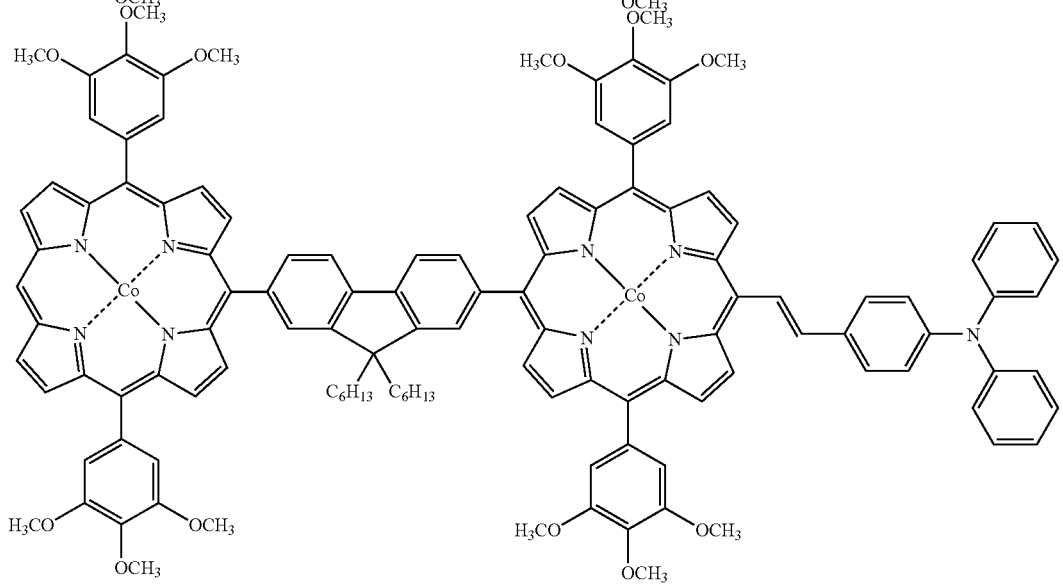
(70)

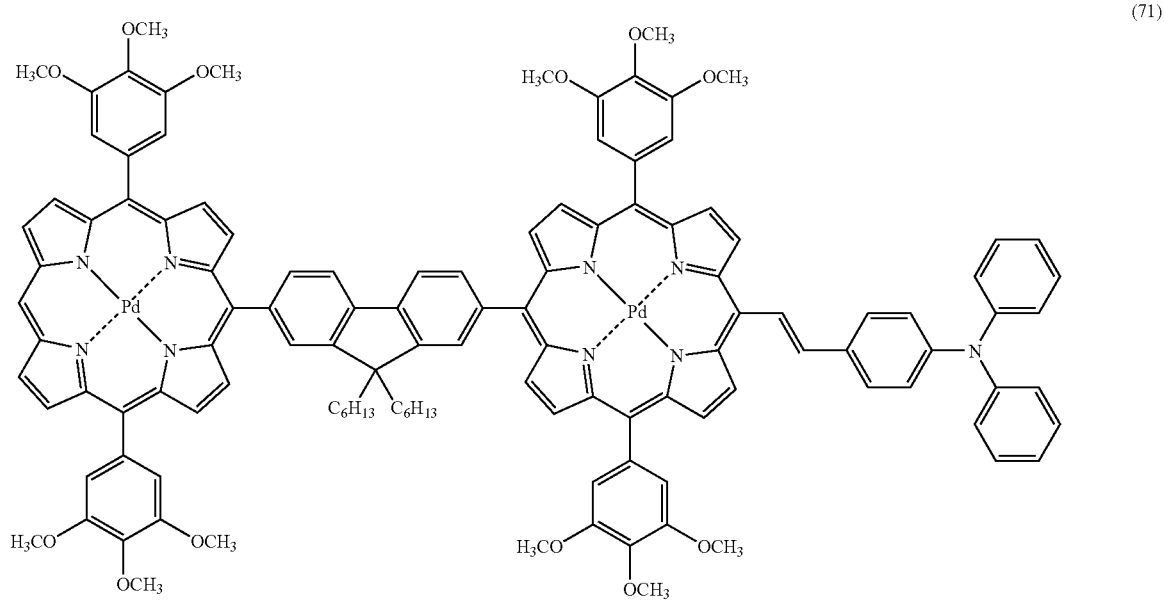
(71)
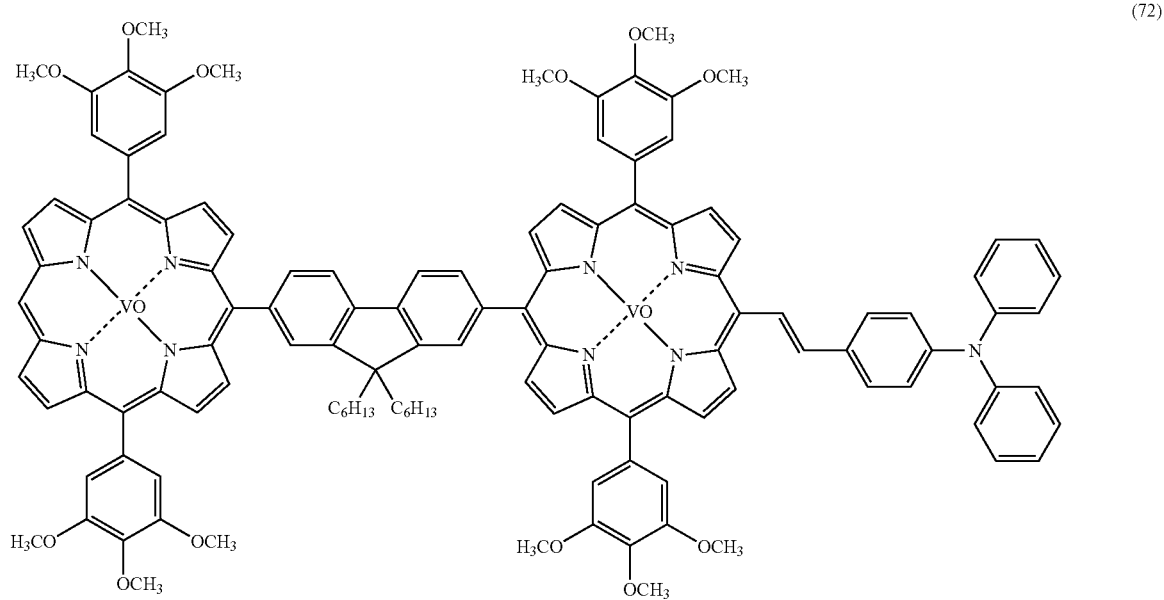
(72)

Two-Photon Absorption Material According to Third Embodiment

A two-photon absorption material according to a third embodiment of the present invention is represented by the following General Formula (A):

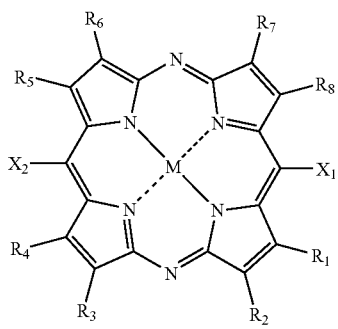

(A)

where $R_1$ to $R_8$ each represent a hydrogen atom, a halogen atom, a nitro group, a cyano group, a hydroxyl group, a carboxyl group, a substituted or unsubstituted alkyl group, a substituted or unsubstituted alkoxy group, a substituted or unsubstituted aryl group, a substituted or unsubstituted amino group, or a substituted or unsubstituted acyl group; $X_1$ and $X_2$ each represent a hydrogen atom, a halogen atom, a nitro group, a cyano group, a hydroxyl group, a carboxyl group, a substituted or unsubstituted alkyl group, a substituted or unsubstituted alkoxy, group, a substituted or unsubstituted aryl group, a substituted or unsubstituted amino group, a substituted or unsubstituted acyl group, or a group having a substituted or unsubstituted triphenylamine structure which group may be bonded via a linking group to a diazaporphyrin skeleton; at least one of $X_1$ and $X_2$ represents the group having a substituted or unsubstituted triphenylamine structure which group may be bonded via a linking group to a diazaporphyrin skeleton; and M represents two hydrogen atoms, a divalent, trivalent or tetravalent metal atom which may have an oxygen atom or a halogen atom, or a metal atom which may have at least one selected from groups $(OR_9)$a, $(OSiR_{10}R_{11}R_{12})$b, $(OPOR_{13}R_{14})$c and $(OCOR_{15})$d (in the groups, $R_9$ to $R_{15}$ each represent a hydrogen atom or a substituted or unsubstituted aliphatic group or aromatic hydrocarbon group, and each of a, b, c and d is an integer of 0 to 2).

Next will be described diazaporphyrin derivatives used in the present invention.

Similar to porphyrins, the diazaporphyrin derivatives are macrocyclic conjugated compounds.

In general, porphyrins are compounds formed from four pyrrole rings which are bonded to one another via each carbon atom at meso positions. In the diazaporphyrin derivatives of the present invention, nitrogen atoms are located instead of two carbon atoms facing each other among four meso-position carbon atoms which bond four pyrrole rings to one another in porphyrins and also, at least one of the other two meso-position carbon atoms has, as a substituent, a specific electron donating group.

The diazaporphyrins can be synthesized by a method previously reported. Specifically, the other two meso-position carbon atoms (unsubstituted carbon atoms) are halogenated and then substituted by specific substituents, whereby the compounds of the present invention can be produced.

J. Org. Chem. (1993, 58, pp. 5,983 to 5,993), J. Chem. Soc. Chem. Commun. (1995, 5, pp. 527 to 528) and other literatures describe the halogenation. From these literatures, it is known that the number of halogen atoms to be bonded can be controlled.

When Zn is used as a central metal in the diazaporphyrins, the formed diazaporphyrins exhibit sharp absorption and improve in two-photon absorptivity. Thus, the optimum central metal is Zn. In addition, inclusion of Zn in a porphyrin ring can be performed at higher yield as compared with the case where the other metals are used and thus, Zn is the most suitable metal for industrial applications.

Next will be given synthesis schemes for diazaporphyrin derivatives represented by Compounds 1 to 4 given below.

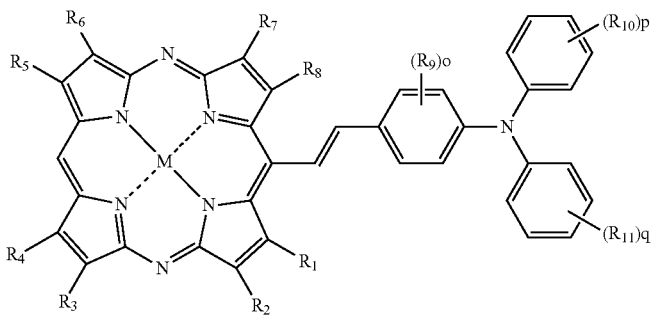

Compound 1

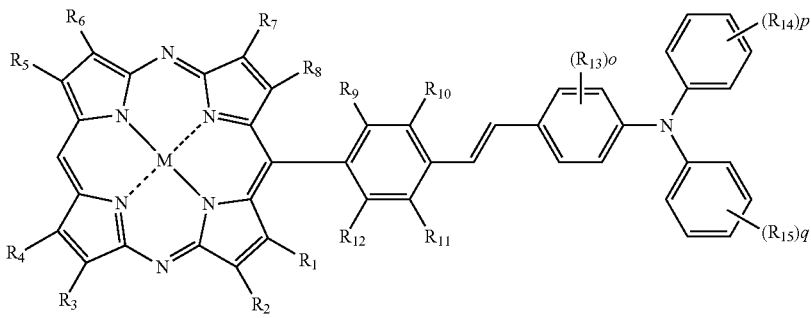

Compound 2

Compound 3
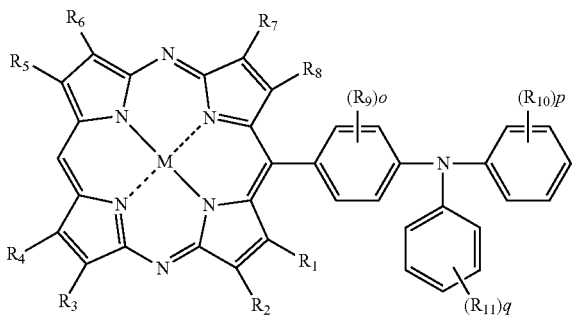
Compound 4
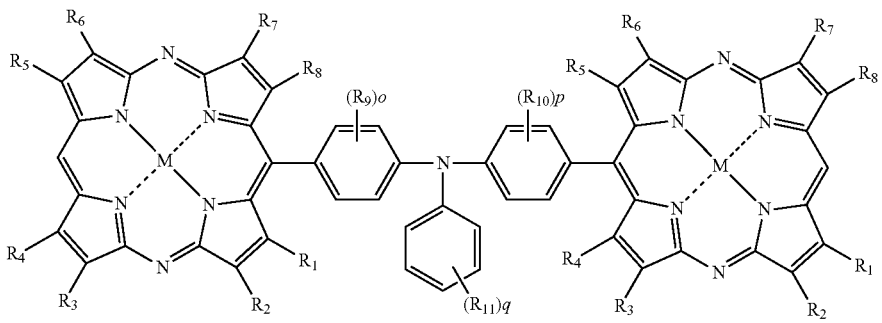
Heck Reaction:
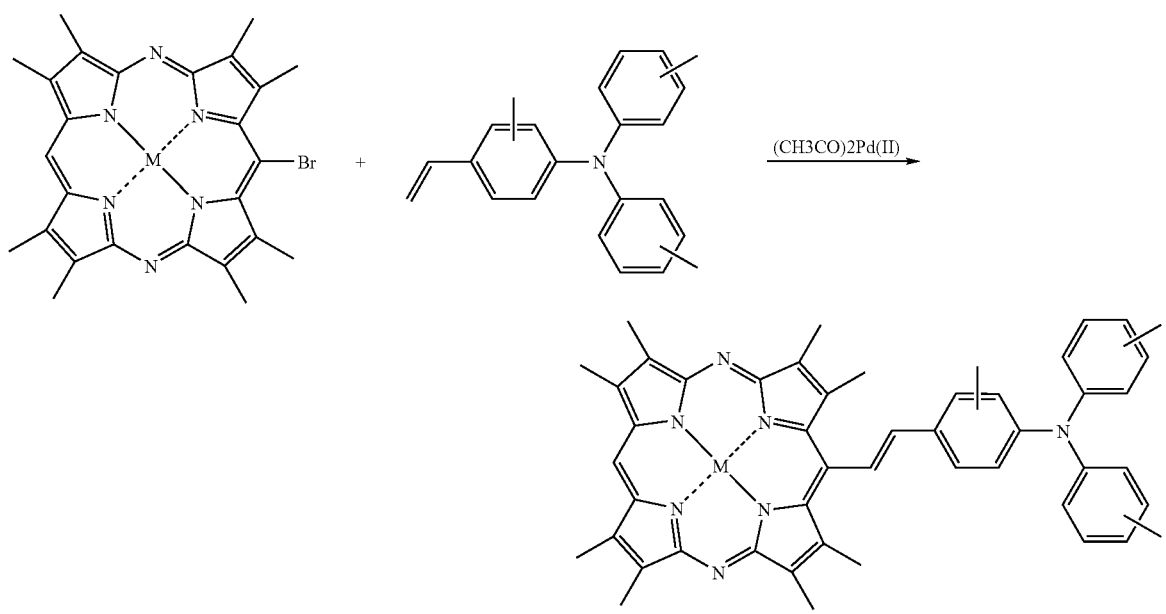
Suzuki Coupling Reaction:
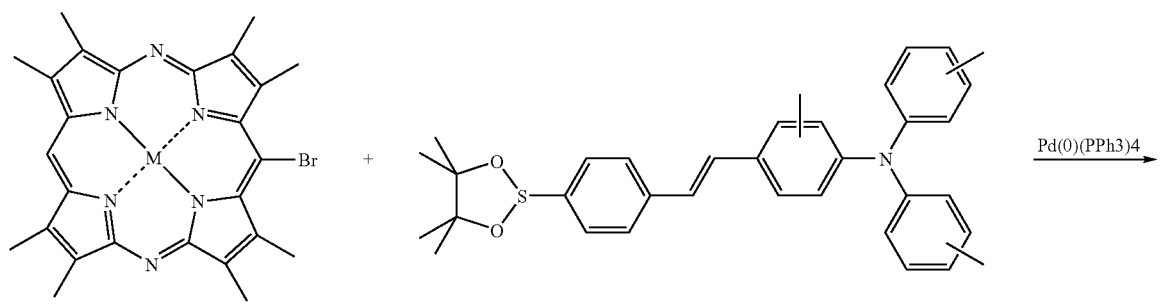

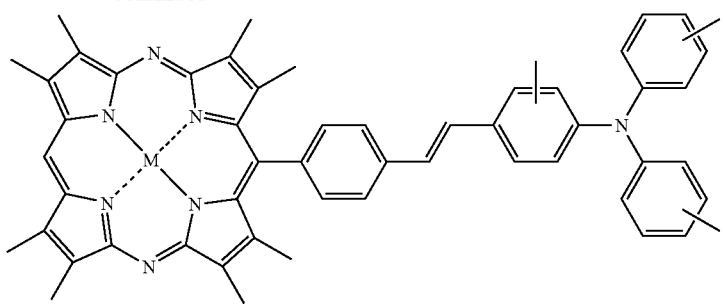
Suzuki Coupling Reaction:
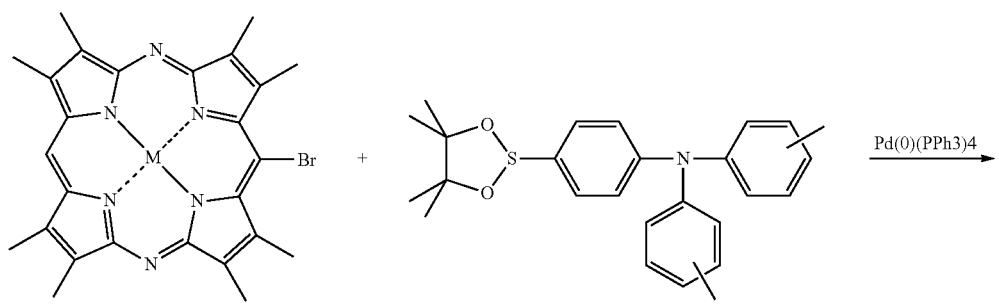
Suzuki Coupling Reaction:
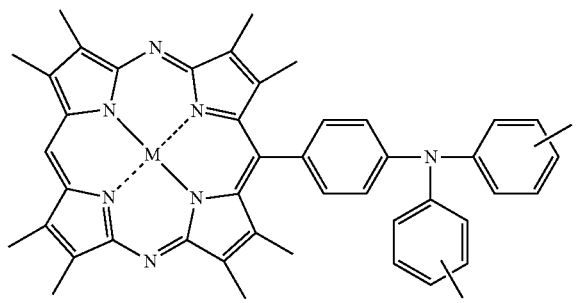
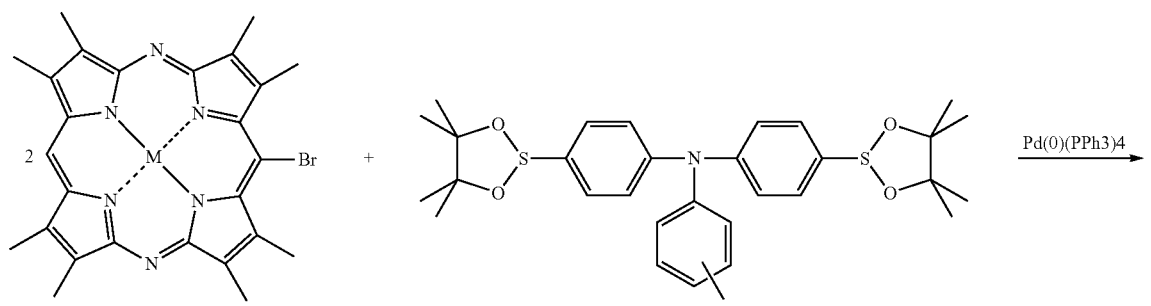
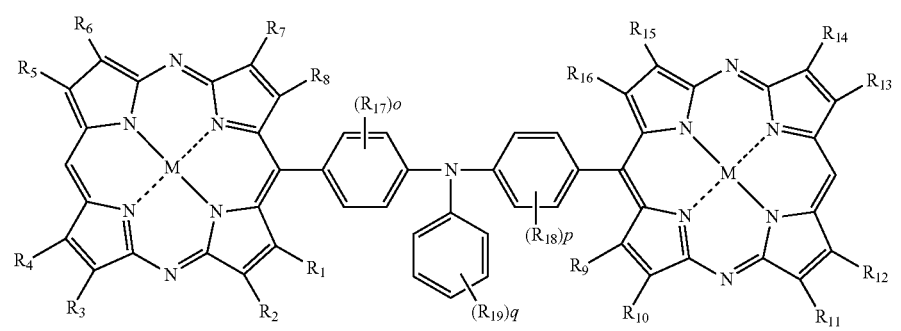

Similarly, diazaporphyrin derivatives represented by Compounds 5 to 7 can be synthesized using diazaporphyrin derivatives whose two unsubstituted meso-position carbon atoms have been brominated.

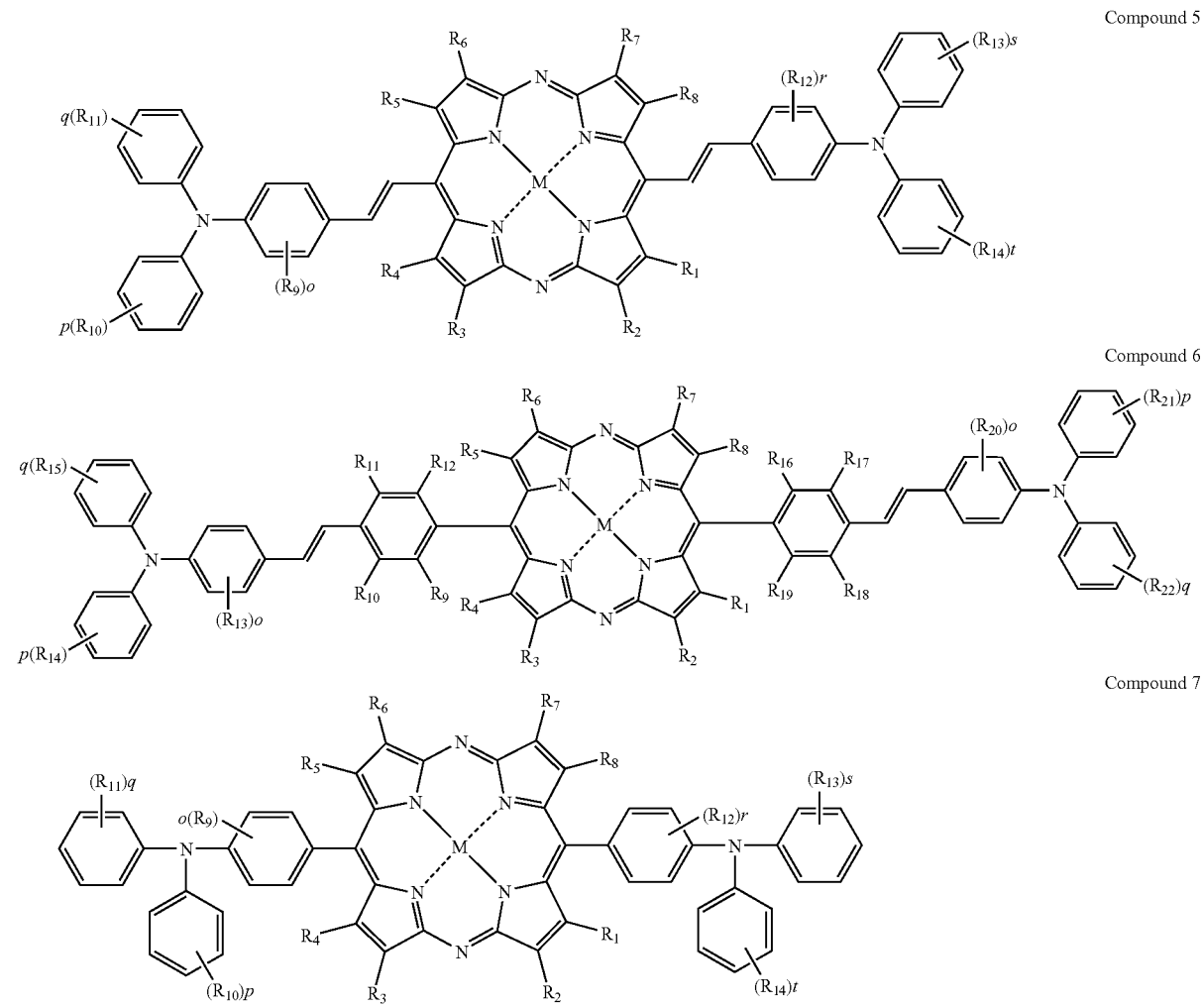

Compound 5

Compound 6

Compound 7

Examples of the unsubstituted alkyl group or the alkyl group contained in the unsubstituted alkoxy group include linear or branched alkyl groups. Examples of the substituted alkyl group or the substituted alkyl group contained in the substituted alkoxy group include hydroxy-substituted alkyl groups such as 2-hydroxyethyl, 3-hydroxypropyl, 4-hydroxybutyl and 2-hydroxypropyl; carboxy-substituted alkyl groups such as carboxymethyl, 2-carboxyethyl and 3-carboxypropyl; cyano-substituted alkyl groups such as 2-cyanoethyl and cyanomethyl; amino-substituted alkyl groups such as 2-aminoethyl; halogen-substituted alkyl groups such as 2-chloroethyl, 3-chloropropyl, 2-chloropropyl and 2,2,2-trifluoroethyl; phenyl-substituted alkyl groups such as benzyl, p-chlorobenzyl and 2-phenylethyl; alkoxy-substituted alkyl groups such as 2-methoxyethyl, 2-ethoxyethyl, 2-(n)propoxyethyl, 2-(iso)propoxyethyl, 2-(n)butoxyethyl, 2-(iso)butoxyethyl, 2-(2-ethylhexyloxy)ethyl, 3-methoxypropyl, 4-methoxybutyl and 2-methoxypropyl; alkoxyalkoxy-substituted alkyl groups such as 2-(2-methoxyethoxy)ethyl, 2-(2-ethoxyethoxy)ethyl, 2-(2-(n)propoxyethoxy)ethyl, 2-(2-(iso) propoxyethoxy)ethyl, 2-(2-(n)butoxyethoxy)ethyl, 2-(2-(iso) butoxyethoxy)ethyl and 2-{2-(2-ethylhexyloxy) ethoxy}ethyl; substituted alkyl groups such as allyloxyethyl, 2-phenoxyethyl and 2-benzyloxyethyl; acyloxy-substituted alkyl groups such as 2-acetyloxyethyl, 2-propionyloxyethyl, 2-(n)butylyloxyethyl, 2-(iso)butylyloxyethyl and 2-trifluoroacetyloxyethyl; substituted or unsubstituted alkoxycarbonyl-substituted alkyl groups such as methoxycarbonylmethyl, ethoxycarbonylmethyl, (n)propoxycarbonylmethyl, (iso) propoxycarbonylmethyl, (n)butoxycarbonylmethyl, (iso)butoxycarbonylmethyl, 2-ethylhexyloxycarbonylmethyl, benzyloxycarbonylmethyl, furfuryloxycarbonylmethyl, tetrahydrofurfuryloxycarbonylmethyl, 2-methoxycarbonylethyl, 2-ethoxycarbonylethyl, 2-(n)propoxycarbonylethyl, 2-(iso)propoxycarbonylethyl, 2-(n)butoxycarbonylethyl, 2-(iso)butoxycarbonylethyl, 2-(2-ethylhexyloxycarbonyl) ethyl, 2-benzyloxycarbonylethyl and 2-furfuryloxycarbonylethyl; substituted or unsubstituted alkoxycarbonyloxy-substituted alkyl groups such as 2-methoxycarbonyloxyethyl, 2-ethoxycarbonyloxyethyl, 2-(n)propoxycarbonyloxyethyl, 2-(iso)propoxycarbonyloxyethyl, 2-(n)butoxycarbonyloxyethyl, 2-(iso)butoxycarbonyloxyethyl, 2-(2-ethylhexyloxycarbonyloxy)ethyl, 2-benzyloxycarbonyloxyethyl and 2-furfuryloxycarbonyloxyethyl; and hetro ring-substituted alkyl groups such as furfuryl and tetrahydrofurfuryl.

Also, examples of cycloalkyl groups include cyclopentyl and cyclohexyl.

Specific examples of the alkyl group or the alkyl group contained in the alkoxy group include primary alkyl groups such as methyl, ethyl, n-propyl, n-butyl, isobutyl, n-pentyl, neopentyl, isoamyl, 2-methylbutyl, n-hexyl, 2-methylpentyl, 3-methylpentyl, 4-methylpentyl, 2-ethylbutyl, n-heptyl, 2-methylhexyl, 3-methylhexyl, 4-methylhexyl, 5-methylhexyl, 2-ethylpentyl, 3-ethylpentyl, n-octyl, 2-methylheptyl, 3-methylheptyl, 4-methylheptyl, 5-methylheptyl, 2-ethylhexyl, 3-ethylhexyl, n-nonyl, n-decyl and n-dodecyl; secondary alkyl groups such as isopropyl, sec-butyl, 1-ethylpropyl, 1-methylbutyl, 1,2-dimethylpropyl, 1-methylheptyl, 1-ethylbutyl, 1,3-dimethylbutyl, 1,2-dimethylbutyl, 1-ethyl-2-methylpropyl, 1-methylhexyl, 1-ethylheptyl, 1-propylbutyl, 1-isopropyl-2-methylpropyl, 1-ethyl-2-methylbutyl, 1-propyl-2-methylpropyl, 1-methylheptyl, 1-ethylhexyl, 1-propylpentyl, 1-isopropylpentyl, 1-isopropyl-2-methylbutyl, 1-isopropyl-3-methylbutyl, 1-methyloctyl, 1-ethylheptyl, 1-propylhexyl and 1-isobutyl-3-methylbutyl; tertiary alkyl groups such as tert-butyl, tert-hexyl, tert-amyl and tert-octyl; and cycloalkyl groups such as cyclohexyl, 4-methylcyclohexyl, 4-ethylcyclohexyl, 4-tert-butylcyclohexyl, 4-(2-ethylhexyl)cyclohexyl, bornyl, isobornyl and adamantine. Note that these alkyl groups may have a substituent such as a halogen atom.

Examples of the aryl group include phenyl, methylphenyl, dimethylphenyl, trimethylphenyl, ethylphenyl, tert-butylphenyl, di(tert-butyl)phenyl, butylphenyl, methoxyphenyl, dimethoxyphenyl, trimethoxyphenyl and butoxyphenyl. Note that these aryl groups may have a substituent such as a halogen atom.

In Compounds 1 to 7, M represents two hydrogen atoms, a divalent, trivalent or tetravalent metal atom which may have an oxygen atom or a halogen atom, or a metal atom which may have at least one selected from groups $(OR_9)a$, $(OSiR_{10}R_{11}R_{12})b$, $(OPOR_{13}R_{14})c$ or $(OCOR_{15})d$ (in the groups, $R_9$ to $R_{15}$ each represent a hydrogen atom or a substituted or unsubstituted aliphatic group or aromatic hydrocarbon group, and each of a, b, c and d is an integer of 0 to 2).

Examples of the metal atom represented by M include metals belonging to Groups Ib, IIa, IIb, IIIa, IVa, IVb, Vb, VIb, VIb and VIII, oxides of the metals, halides of the metals, hydroxides of the metals, and the metals having a substituent(s).

Specific examples of the metals include Cu, Zn, Mg, Al, Ge, Ti, Sn, Pb, Cr, Mo, Mn, Fe, Co, Ni, In, Pt and Pd. Specific examples of the oxides include TiO and VO. Specific examples of the halides include AlCl, $GeCl_2$, $SiCl_2$, FeCl, $SnCl_2$ and InCl. Specific examples of the hydroxides include $Al(OH)_3$, $Si(OH)_2$, $Ge(OH)_2$ and $Sn(OH)_2$.

In the metals having a substituent(s), the metal is, for example, Al, Ti, Si, Ge or Sn; and the substituent is, for example, an aryloxyl group, an alkoxyl group, a trialkylsiloxyl group, a triarysiloxyl group, a trialkoxysiloxyl group, a triaryloxysiloxyl group, a trityloxyl group or an acyloxyl group.

Porphyrin derivatives of the present invention can be synthesized by the method described in, for example, Angew. Chem. Int. Ed. Engl. 1993, 32, No. 11, pp. 1,600 to 1,604.

Exemplary porphyrin derivatives of the present invention are given below.

TABLE C1

Compound 1

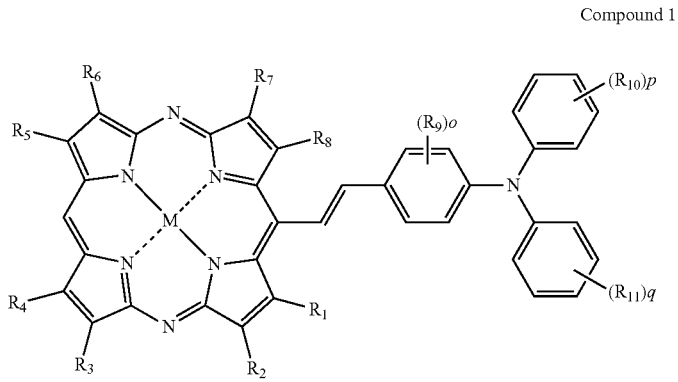

| | R1 | R2 | R3 | R4 | R5 | R6 | R7 | R8 | R9 | R10 | R11 | M |
|---|---|---|---|---|---|---|---|---|---|---|---|---|
| Compd. 1-1 | Et | Et | Et | Et | Et | Et | Et | Et | H | p-OMe | p-OMe | 2H |
| Compd. 1-2 | Et | Me | Me | Et | Et | Me | Me | Et | H | p-nBu | p-nBu | 2H |
| Compd. 1-3 | nPr | Me | Me | nPr | nPr | Me | Me | nPr | H | p-Me | p-Me | 2H |
| Compd. 1-4 | *1 | Me | Me | *1 | *1 | Me | Me | *1 | H | p-Me | p-Me | 2H |
| Compd. 1-5 | Et | Et | Et | Et | Et | Et | Et | Et | H | p-OMe | p-OMe | Zn |
| Compd. 1-6 | Et | Me | Me | Et | Et | Me | Me | Et | H | p-nBu | p-nBu | Ni |
| Compd. 1-7 | nPr | Me | Me | nPr | nPr | Me | Me | nPr | H | p-Me | p-Me | Zn |

*1: —$CH_2CH_3COOH$

TABLE C2

Compound 2

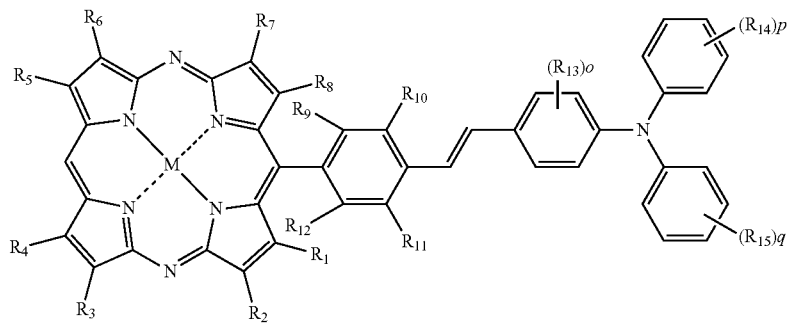

| | R1 | R2 | R3 | R4 | R5 | R6 | R7 | R8 | R9 | R10 | R11 | R12 | R13 | R14 | R15 | M |
|---|---|---|---|---|---|---|---|---|---|---|---|---|---|---|---|---|
| Compd. 2-1 | Et | Et | Et | Et | Et | Et | Et | Et | H | H | H | H | H | p-Me | p-Me | 2H |
| Compd. 2-2 | Et | Me | Me | Et | Et | Me | Et | Me | H | H | H | H | H | p-Me | p-Me | 2H |
| Compd. 2-3 | nPr | Me | Me | nPr | nPr | Me | nPr | Me | H | H | H | H | H | p-Me | p-Me | 2H |
| Compd. 2-4 | *1 | Me | Me | *1 | *1 | Me | *1 | Me | H | H | H | H | H | p-Me | p-Me | 2H |
| Compd. 2-5 | Et | Et | Et | Et | Et | Et | Et | Et | H | H | H | H | H | p-Me | p-Me | Mn |
| Compd. 2-6 | Et | Me | Me | Et | Et | Me | Et | Me | H | H | H | H | H | p-Me | p-Me | Zn |
| Compd. 2-7 | nPr | Me | Me | nPr | nPr | Me | nPr | Me | H | H | H | H | H | p-Me | p-Me | Zn |

*1: —CH$_2$CH$_3$COOH

TABLE C3

Compound 3

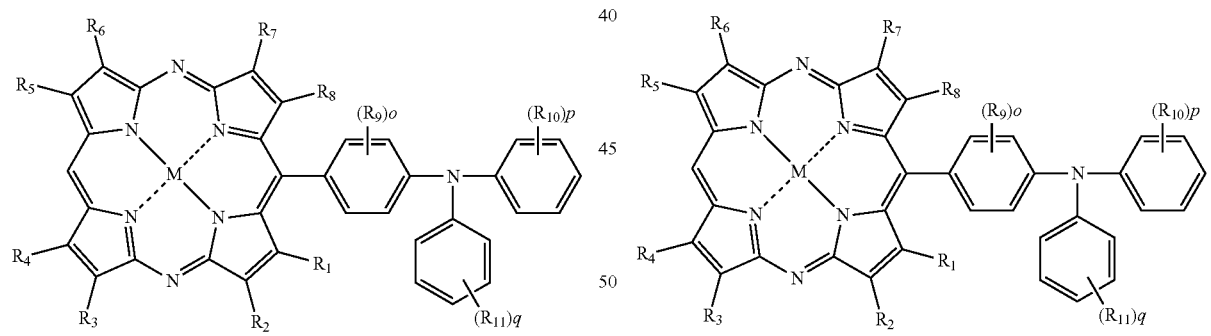

| | R1 | R2 | R3 | R4 | R5 | R6 | R7 | R8 | R9 | R10 | R11 | M |
|---|---|---|---|---|---|---|---|---|---|---|---|---|
| Compd. 3-1 | Et | Et | Et | Et | Et | Et | Et | Et | H | H | p-nHex | 2H |
| Compd. 3-2 | Et | Me | Me | Et | Et | Me | Me | Et | H | H | p-nHex | 2H |
| Compd. 3-3 | nPr | Me | Me | nPr | nPr | Me | Me | nPr | H | H | p-Ome | 2H |
| Compd. 3-4 | *1 | Me | Me | *1 | *1 | Me | Me | *1 | H | H | p-nHex | 2H |
| Compd. 3-5 | Et | Me | Me | Et | Et | Me | Me | Et | H | H | p-nHex | Cu |
| Compd. 3-6 | nPr | Me | Me | nPr | nPr | Me | Me | nPr | H | H | p-Ome | Ni |
| Compd. 3-7 | *1 | Me | Me | *1 | *1 | Me | Me | *1 | H | H | p-nHex | Zn |

*1: —CH$_2$CH$_3$COOH

TABLE C4

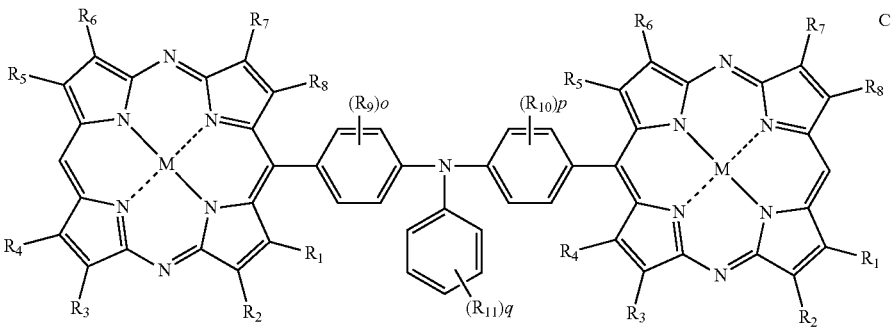

Compound 4

| | R1 | R2 | R3 | R4 | R5 | R6 | R7 | R8 | R9 | R10 | R11 | R12 | R13 | R14 | R15 | R16 | R17 | R18 | R19 | M |
|---|---|---|---|---|---|---|---|---|---|---|---|---|---|---|---|---|---|---|---|---|
| Compd. 4-1 | Et | Et | Et | Et | Et | Et | Et | Et | Et | Et | Et | Et | Et | Et | Et | H | H | p-Hex | | 2H |
| Compd. 4-2 | Et | Me | Me | Et | Et | Me | Me | Et | Et | Me | Me | Et | Et | Me | Me | Et | H | H | p-Me | 2H |
| Compd. 4-3 | nPr | Me | Me | nPr | nPr | Me | Me | nPr | nPr | Me | Me | nPr | nPr | Me | Me | nPr | H | H | p-Hex | 2H |
| Compd. 4-4 | *1 | Me | Me | *1 | *1 | Me | Me | *1 | *1 | Me | Me | *1 | *1 | Me | Me | *1 | H | H | p-Me | 2H |
| Compd. 4-5 | Et | Me | Me | Et | Et | Me | Me | Et | Et | Me | Me | Et | Et | Me | Me | Et | H | H | p-Me | Ni |
| Compd. 4-6 | nPr | Me | Me | nPr | nPr | Me | Me | nPr | nPr | Me | Me | nPr | nPr | Me | Me | nPr | H | H | p-Hex | Zn |
| Compd. 4-7 | *1 | Me | Me | *1 | *1 | Me | Me | *1 | *1 | Me | Me | *1 | *1 | Me | Me | *1 | H | H | p-Me | Zn |

*1: —CH$_2$CH$_3$COOH

TABLE C5

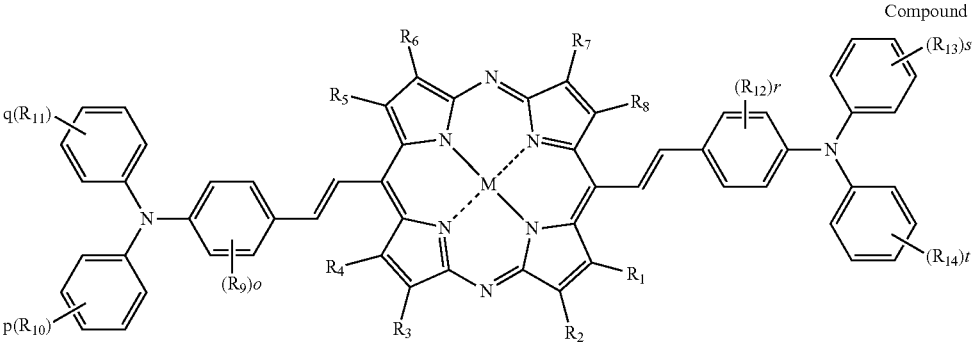

Compound 5

| | R1 | R2 | R3 | R4 | R5 | R6 | R7 | R8 | R9 | R10 | R11 | R12 | R13 | R14 | M |
|---|---|---|---|---|---|---|---|---|---|---|---|---|---|---|---|
| Compd. 5-1 | Et | Et | Et | Et | Et | Et | Et | Et | H | p-OMe | p-OMe | H | p-OMe | p-OMe | 2H |
| Compd. 5-2 | Et | Me | Me | Et | Et | Me | Me | Et | H | p-nBu | p-nBu | H | p-nBu | p-nBu | 2H |
| Compd. 5-3 | nPr | Me | Me | nPr | nPr | Me | Me | nPr | H | p-Me | p-Me | H | p-Me | p-Me | 2H |
| Compd. 5-4 | *1 | Me | Me | *1 | *1 | Me | Me | *1 | H | p-Me | p-Me | H | p-Me | p-Me | 2H |
| Compd. 5-5 | nPr | Me | Me | nPr | nPr | Me | Me | nPr | H | p-Me | p-Me | H | p-Me | p-Me | Zn |
| Compd. 5-6 | *1 | Me | Me | *1 | *1 | Me | Me | *1 | H | p-Me | p-Me | H | p-Me | p-Me | Zn |

*1: —CH$_2$CH$_3$COOH

TABLE C6

Compound 6

| | R1 | R2 | R3 | R4 | R5 | R6 | R7 | R8 | R9 | R10 | R11 | R12 | R13 | R14 | R15 | R16 | R17 | R18 | R19 | R20 | R21 | R22 | M |
|---|---|---|---|---|---|---|---|---|---|---|---|---|---|---|---|---|---|---|---|---|---|---|---|
| Compd. 6-1 | Et | Me | Me | Et | Et | Me | Et | Me | H | H | H | H | H | p-Me | p-Me | H | H | H | H | H | p-Me | p-Me | 2H |
| Compd. 6-3 | nPr | Me | Me | nPr | nPr | Me | nPr | Me | H | H | H | H | H | p-Me | p-Me | H | H | H | H | H | p-Me | p-Me | Zn |
| Compd. 6-3 | *1 | Me | Me | *1 | *1 | Me | *1 | Me | H | H | H | H | H | p-Me | p-Me | H | H | H | H | H | p-Me | p-Me | 2H |

*1: —CH$_2$CH$_3$COOH

TABLE C7

Compound 7

| | R1 | R2 | R3 | R4 | R5 | R6 | R7 | R8 | R9 | R10 | R11 | R12 | R13 | R14 | M |
|---|---|---|---|---|---|---|---|---|---|---|---|---|---|---|---|
| Compd. 7-1 | Et | Et | Et | Et | Et | Et | Et | Et | H | H | p-nHex | H | H | p-nHex | 2H |
| Compd. 7-2 | Et | Me | Me | Et | Et | Me | Me | Et | H | H | p-nHex | H | H | p-nHex | Zn |
| Compd. 7-3 | nPr | Me | Me | nPr | nPr | Me | Me | nPr | H | H | p-Ome | H | H | p-Ome | 2H |
| Compd. 7-4 | *1 | Me | Me | *1 | *1 | Me | Me | *1 | H | H | p-nHex | H | H | p-nHex | 2H |

*1: —CH$_2$CH$_3$COOH

EXAMPLES

The present invention will next be described in more detail by way of examples, which should not be construed as limiting the present invention thereto.

Examples A-1 to A-16

Each of the above-given compounds Nos. 1, 2, 4, 5, 6, 7, 10, 11, 15, 16, 17, 20, 24, 25, 27 and 28 of the present invention was dissolved in tetrahydrofuran, and the resultant solution was measured for its two-photon absorption cross-sectional area according to the below-described evaluation method therefor. The results are shown in Table A1.

Comparative Example A-1

The following compound (29) was dissolved in tetrahydrofuran, and the resultant solution was measured for its two-photon absorption cross-sectional area according to the below-described evaluation method therefor. The results are shown in Table A1.

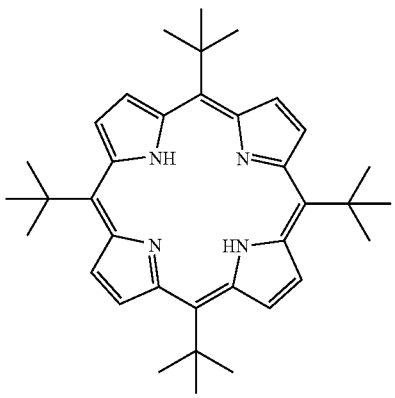

(29)

Comparative Example A-2

The following compound (30) was dissolved in tetrahydrofuran, and the resultant solution was measured for its two-photon absorption cross-sectional area according to the below-described evaluation method therefor. The results are shown in Table A1.

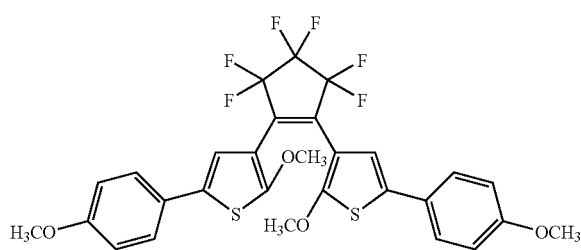

(30)

[Method for Measuring Two-Photon Absorption Cross-Sectional Area]

Figure 8:
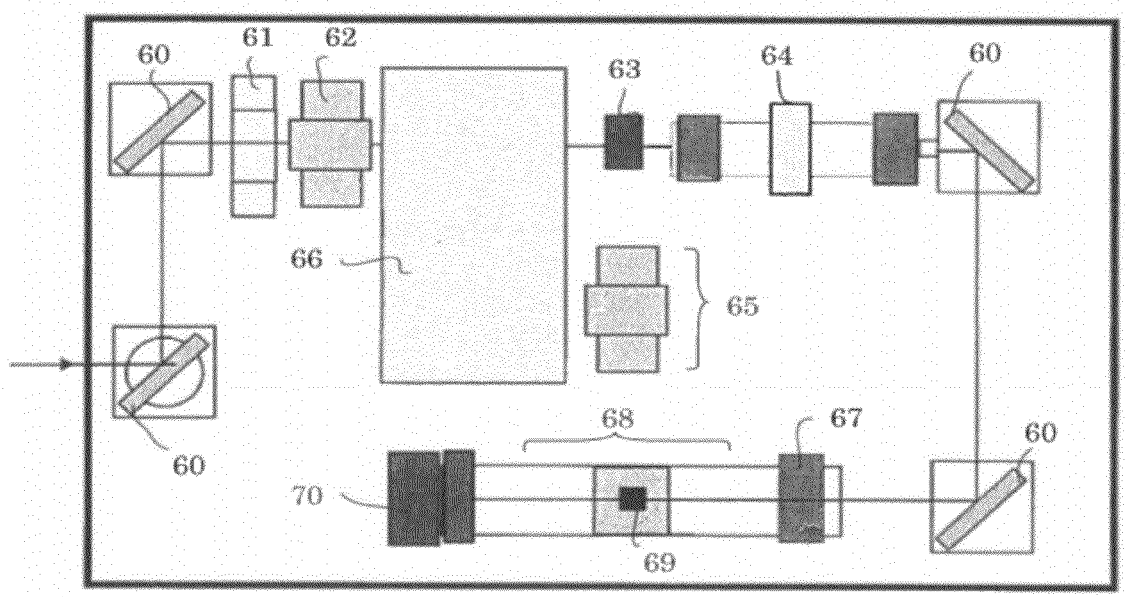
FIG. 8 schematically shows a measurement system used in the present invention, wherein reference numerals 60, 61, 62, 63, 64, 65, 66, 67, 68, 69, 70 denote a mirror, a λ/2 wavelength plate, a Glan laser prism, a λ/4 wavelength plate, a spatial filter, a microscope equipped with a CCD camera, a Kerr cell high-speed shutter, an objective lens, a movable sample stage, a quartz cell and a detector, respectively.

FIG. 8 schematically illustrates a system of the method.

Measuring light source: femtosecond titanium sapphire laser
  Wavelength: 800 nm
  Pulse width: 100 fs
  Repetition frequency: 80 MHz
  Light power: 800 mW
  Measuring method: Z scan method
  Wavelength of light source: 800 nm
  Inner diameter of cuvette: 10 mm
  Light power for measurement: about 500 mW
  Repetition frequency: 80 MHz
  Collective lens: f=75 mm
  Collection diameter: 40 µm to 50 µm A quartz cell filled with each sample solution was placed in a light path through which a focused laser beam was passed. Then, the cell was moved along the light path for Z-scan measurement.

The sample solution was measured for its transmittance, and the thus-obtained value and the following theoretical equation (1) were used to determine a nonlinear absorption coefficient of the sample.

$$T=[\ln(1+I0L0\beta)]/I0L0\beta \quad (1)$$

where T denotes a transmittance (%), I0 denotes an excited light density [GW/cm$^2$], L0 denotes a sample cell length [cm], and β denotes a nonlinear absorption coefficient [cm/GW].

The thus-determined nonlinear absorption coefficient and the following equation (2) were used to calculate a two-photon absorption cross-sectional area σ. Note that the unit of σ is GM (1 GM=1×10$^{-50}$ cm$^4$·s·photon$^{-1}$).

$$\sigma=1{,}000 \times h\nu\beta/NAC\beta \quad (2)$$

where h denotes the Planck's constant [J·s], ν denotes a frequency of an incident laser beam [s$^{-1}$], NA denotes the Avogadro's number, and C denotes a concentration of a solution [mol/L].

TABLE A1

| Sample | Compound No. | Two-photon absorption cross-sectional area (GM) |
|---|---|---|
| Ex. A-1 | 1 | 980 |
| Ex. A-2 | 2 | 560 |
| Ex. A-3 | 4 | 1,010 |
| Ex. A-4 | 5 | 1,480 |
| Ex. A-5 | 6 | 730 |
| Ex. A-6 | 7 | 1,000 |
| Ex. A-7 | 10 | 860 |
| Ex. A-8 | 11 | 890 |
| Ex. A-9 | 15 | 880 |
| Ex. A-10 | 16 | 720 |
| Ex. A-11 | 17 | 840 |
| Ex. A-12 | 20 | 820 |
| Ex. A-13 | 24 | 990 |
| Ex. A-14 | 25 | 1,020 |
| Ex. A-15 | 27 | 870 |
| Ex. A-16 | 28 | 590 |
| Comp. Ex. A-1 | 29 | ≈0 |
| Comp. Ex. A-2 | 30 | 15 |

As is clear from the values shown in Table A1, the two-photon absorption materials of the present invention were found to show two-photon absorption cross-sectional areas at least 10 times those of conventionally known two-photon absorption materials and thus, exhibit improved two-photon absorptivity.

Unlike porphyrins, the porphyrin derivatives of the present invention were found to show large two-photon absorption cross-sectional areas.

The compounds of the present invention excellent in two-photon absorptivity require no high-output laser; i.e., require an intensity about ⅒ times the intensity required for conventionally known materials. Thus, the present invention can provide materials which can be used for various applications with an inexpensive laser; i.e., can provide promising materials applicable to three-dimensional memory, light restricting devices, optical molding materials, dyes used for two-photon fluorescence microscopy, etc.

In Table A1, when the value of Example A-1 is compared with that of Example A-2, and the value of Example A-4 is compared with that of Example A-14, it is clear that a trifluoromethyl group contributes to improvement in two-photon absorptivity.

In addition, as is clear from the values of Examples A-3, A-4, A-7 and A-13, Zn is a suitable central metal. Further, from the values of Examples A-5, A-6 and A-14, the porphyrin derivatives having Zn as a central metal were found to exhibit excellent results.

Example A-17

Compounds Nos. 1, 2, 5, 7, 22, 23, 24 and 25 were measured for saturation solubility to THF. The values of Compound Nos. 1, 5, 7, 22, 23, 24 and 25 were each divided by the value of Compound No. 2; i.e., the saturation solubility of Compound No. 2 being regarded as 1.0. Table A2 shows the relative values as calculated above.

TABLE A2

| Compound No. | Saturation solubility (relative value) |
|---|---|
| No. 1 | 1.7 |
| No. 2 | 1.0 |
| No. 5 | 4.8 |
| No. 7 | 2.0 |
| No. 22 | 2.6 |
| No. 23 | 1.1 |
| No. 24 | 4.6 |
| No. 25 | 2.5 |

In comparison of No. 1 with No. 2 in Table A2, the porphyrin derivative having a trifluoromethyl group was found to exhibit solubility 1.7 times higher than that of the porphyrin having no trifluoromethyl group. In addition, from the values of Nos. 5, 7 and 25, the effect of a trifluoromethyl group was observed.

Furthermore, when the value of No. 1 is compared with that of No. 24, and the value of No. 22 is compared with that of No. 23, a triphenylamine group—a bulky electron-donating group—contributes to further improved solubility.

As described above, when a trifluoromethyl group or a triphenylamine group is introduced into porphyrin derivatives, two-photon absorption porphyrin derivatives excellent in film-forming property can be produced.

Examples B-1 to B-36

Each of Compounds (1), (2), (57), (58), (59), (60), (3), (4), (61), (62), (25), (26), (63), (64), (65), (66), (45), (67), (68), (69), (70), (71), (72), (5), (9), (13), (19), (27), (31), (32), (34), (36), (39), (44), (53) and (55) was dissolved in tetrahydrofuran, and the resultant tetrahydrofuran solution was measured for its two-photon absorption cross-sectional area according to the below-described evaluation method therefor.

This measurement was performed under the following conditions:

Sample concentration: $10^{-2}$ mol to $10^{-5}$ mol (this range covering optimal concentrations of the samples (at which measurements are easily performed));

Light path length of cell: 10 mm (corresponding to the inner diameter of cuvette);

Light: variable femtosecond laser having a wavelength of 710 nm to 990 nm; and

Light power: 10 mW to 800 mW. The results are shown in Table C1.

Comparative Example B-1

The following compound (73) was dissolved in tetrahydrofuran, and the resultant solution was measured for its two-photon absorption cross-sectional area according to the below-described evaluation method therefor. The results are shown in Table B1.

(73)

Comparative Example B-2

The following compound (74) was dissolved in tetrahydrofuran, and the resultant solution was measured for its two-photon absorption cross-sectional area according to the below-described evaluation method therefor. The results are shown in Table B1.

(74)

[Method for Measuring Two-Photon Absorption Cross-Sectional Area]

FIG. 8 schematically illustrates a system of the method.

Measuring light source: femtosecond titanium sapphire laser
Wavelength: 780 nm to 960 nm
Pulse width: 100 fs
Repetition frequency: 80 MHz
Light power: 800 mW
Measuring method: Z scan method
Inner diameter of cuvette: 10 mm
Light power for measurement: about 500 mW
Repetition frequency: 80 MHz
Collective lens: f=75 mm
Collection diameter: 40 µm to 50 µm A quartz cell filled with each sample solution was placed in a light path through which a focused laser beam was passed. Then, the cell was moved along the light path for Z-scan measurement.

The sample solution was measured for its transmittance, and the thus-obtained value and the following theoretical equation (I) were used to determine a nonlinear absorption coefficient of the sample.

$$T=[\ln(1+I0L0\beta)]/I0L0\beta \quad (I)$$

where T denotes a transmittance (%), I0 denotes an excited light density [GW/cm²], L0 denotes a sample cell length [cm], and β denotes a nonlinear absorption coefficient [cm/GW].

The thus-determined nonlinear absorption coefficient and the following equation (ii) were used to calculate a two-photon absorption cross-sectional area σ. Note that the unit of σ is GM (1 GM=1×10$^{-50}$ cm$^4$·s·photon$^{-1}$).

$$\sigma = 1{,}000 \times h\nu\beta/NAC\beta \quad\quad (ii)$$

where h denotes the Planck's constant [J·s], ν denotes a frequency of an incident laser beam [s$^{-1}$], NA denotes the Avogadoro's number, and C denotes a concentration of a solution [mol/L].

TABLE B1

| Sample | Compound No. | Central metal | Two-photon absorption cross-sectional area (GM) |
|---|---|---|---|
| Ex. B-1 | (1) | H$_2$ | 790 |
| Ex. B-2 | (2) | Zn | 1,060 |
| Ex. B-3 | (57) | Ni | 880 |
| Ex. B-4 | (58) | Cu | 800 |
| Ex. B-5 | (59) | Pd | 860 |
| Ex. B-6 | (60) | VO | 840 |
| Ex. B-7 | (3) | H$_2$ | 840 |
| Ex. B-8 | (4) | Zn | 1,180 |
| Ex. B-9 | (61) | Ni | 900 |
| Ex. B-10 | (62) | Cu | 840 |
| Ex. B-11 | (25) | H$_2$ | 860 |
| Ex. B-12 | (26) | Zn | 1,120 |
| Ex. B-13 | (63) | Ni | 900 |
| Ex. B-14 | (64) | Pd | 890 |
| Ex. B-15 | (65) | Co | 810 |
| Ex. B-16 | (66) | Cu | 820 |
| Ex. B-17 | (45) | Zn | 1,200 |
| Ex. B-18 | (67) | H$_2$ | 990 |
| Ex. B-19 | (68) | Ni | 1,020 |
| Ex. B-20 | (69) | Cu | 920 |
| Ex. B-21 | (70) | Co | 900 |
| Ex. B-22 | (71) | Pd | 1,000 |
| Ex. B-23 | (72) | VO | 940 |
| Ex. B-24 | (5) | H$_2$ | 980 |
| Ex. B-25 | (9) | H$_2$ | 880 |
| Ex. B-26 | (13) | Zn | 1,030 |
| Ex. B-27 | (19) | H$_2$ | 870 |
| Ex. B-28 | (27) | H$_2$ | 810 |
| Ex. B-29 | (31) | Pd | 890 |
| Ex. B-30 | (32) | Ni | 900 |
| Ex. B-31 | (34) | Zn | 1,010 |
| Ex. B-32 | (36) | Co | 860 |
| Ex. B-33 | (39) | H$_2$ | 890 |
| Ex. B-34 | (44) | Zn | 1,000 |
| Ex. B-35 | (53) | H$_2$ | 840 |
| Ex. B-36 | (55) | H$_2$ | 850 |
| Comp. Ex. B-1 | (73) | H$_2$ | ≈0 |
| Comp. Ex. B-2 | (74) |  | 15 |

As is clear from the values shown in Table B1, the two-photon absorption materials of the present invention were found to show two-photon absorption cross-sectional areas at least 10 times those of conventionally known two-photon absorption materials and thus, exhibit improved two-photon absorptivity.

Unlike porphyrins, the porphyrin derivatives of the present invention were found to show large two-photon absorption cross-sectional areas.

The porphyrin derivatives of the present invention were found to show two-photon absorption cross-sectional areas about 10 times that (about 100 GM) of a conventional two-photon absorption material having a similar structure (disclosed in JP-A No. 2005-500394).

In Table B1, the porphyrin derivatives of Examples B-1 to B-6 have the same skeleton and different central atoms, and the same apply to the porphyrin derivatives of Examples B-7 to B-10, the porphyrin derivatives of Examples B-11 to B-16, and the porphyrin derivatives of Examples B-17 to B-23. As is clear form the values in each group, it is found that an optimal central metal is Zn.

The compounds of the present invention excellent in two-photon absorptivity require no high-output laser; i.e., require an intensity about $\frac{1}{10}$ times the intensity required for conventionally known materials. Thus, the present invention can provide materials which can be used for various applications with an inexpensive laser; i.e., can provide promising materials applicable to three-dimensional memory, light restricting devices, optical molding materials, dyes used for two-photon fluorescence microscopy, etc.

Example C-1

Compound 1-7 (porphyrin derivative) of the present invention was dissolved in tetrahydrofuran, and the resultant tetrahydrofuran solution was measured for its two-photon absorption cross-sectional area according to the below-described evaluation method therefor.

Figure 9A:
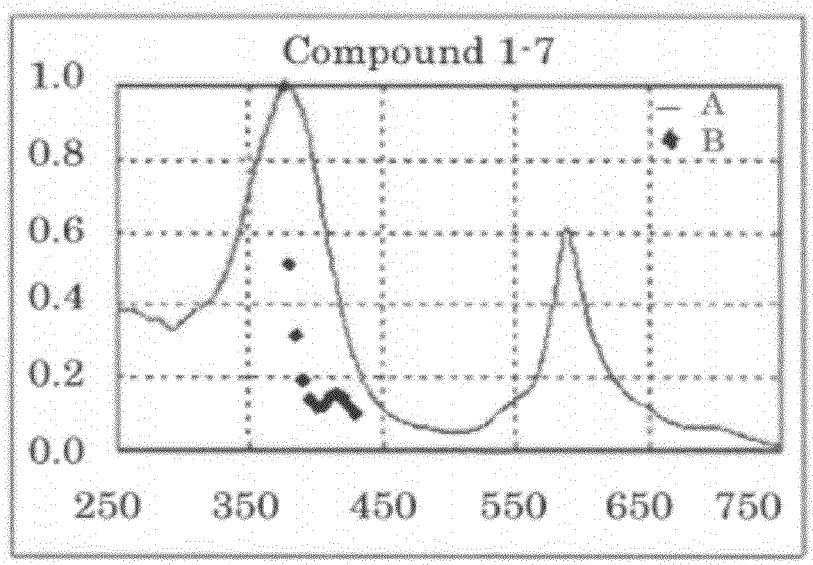
FIG. 9A shows a two-photon absorption spectral chart obtained in Example C-1, wherein the vertical axis corresponds to absorption characteristics, the horizontal axis wavelength (nm); the line indicated by symbol A corresponds to one-photon absorption, and the dots indicated by B two-photon absorption.
Figure 9B:
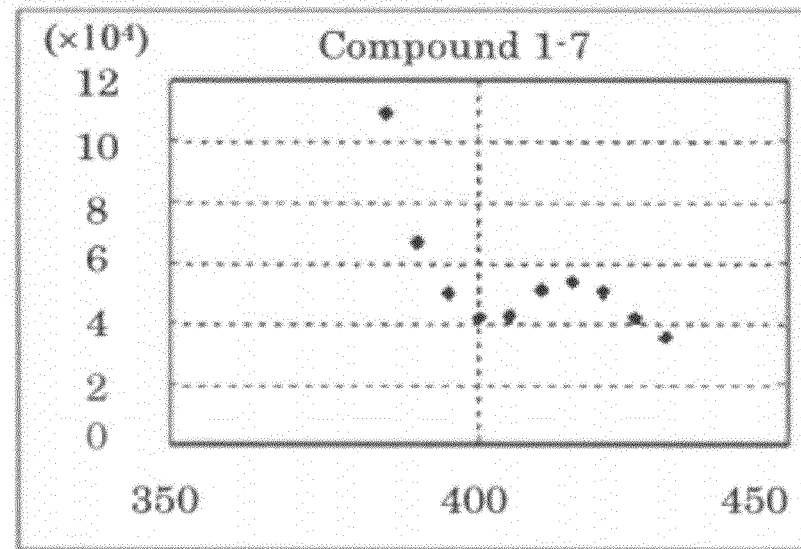
FIG. 9B shows a two-photon absorption spectral chart obtained in Example C-1, wherein two-photon absorption spectra are enlarged, the vertical axis corresponds to two-photon absorption cross-sectional area σ2 (GM), and the horizontal axis wavelength (nm).

Table C8 shows the value of the thus-measured two-photon absorption cross-sectional area, and FIGS. 9A and 9B each show a two-photon absorption spectral chart thereof.

Example C-2

Similarly, Compound 2-7 was measured for its two-photon absorption cross-sectional area.

Figure 10A:
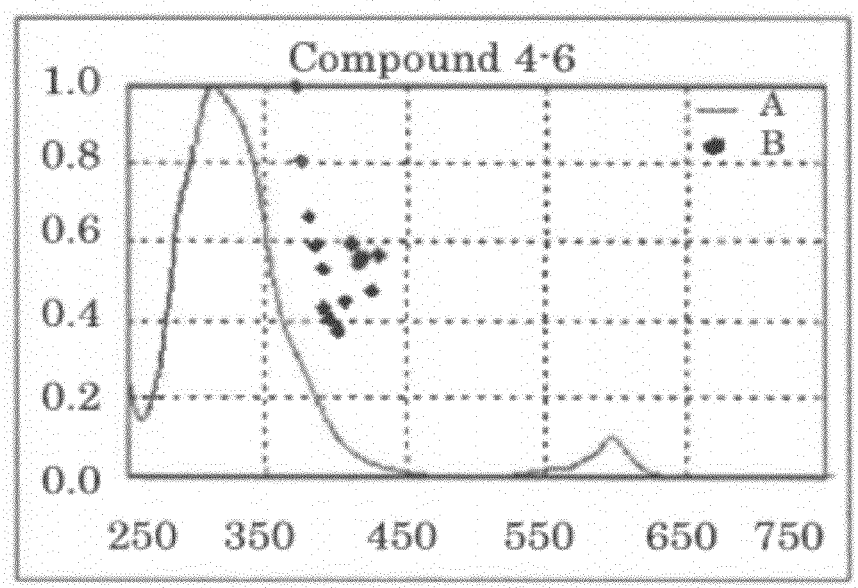
FIG. 10A shows a two-photon absorption spectral chart obtained in Example C-3, wherein the vertical axis corresponds to absorption characteristics, the horizontal axis wavelength (nm); the line indicated by symbol A corresponds to one-photon absorption, and the dots indicated by B two-photon absorption.
Figure 10B:
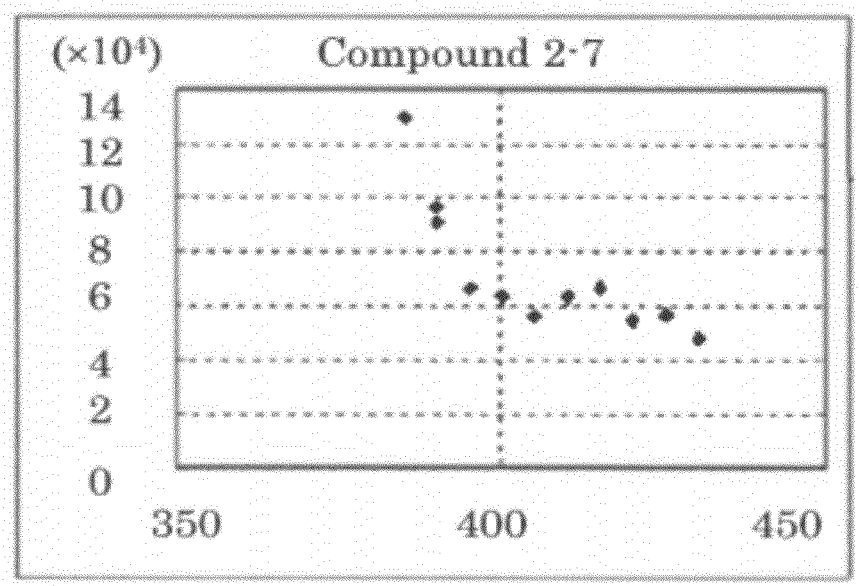
FIG. 10B shows a two-photon absorption spectral chart obtained in Example C-2, wherein two-photon absorption spectra are enlarged, the vertical axis corresponds to two-photon absorption cross-sectional area σ2 (GM), and the horizontal axis wavelength (nm).
Figure 11A:
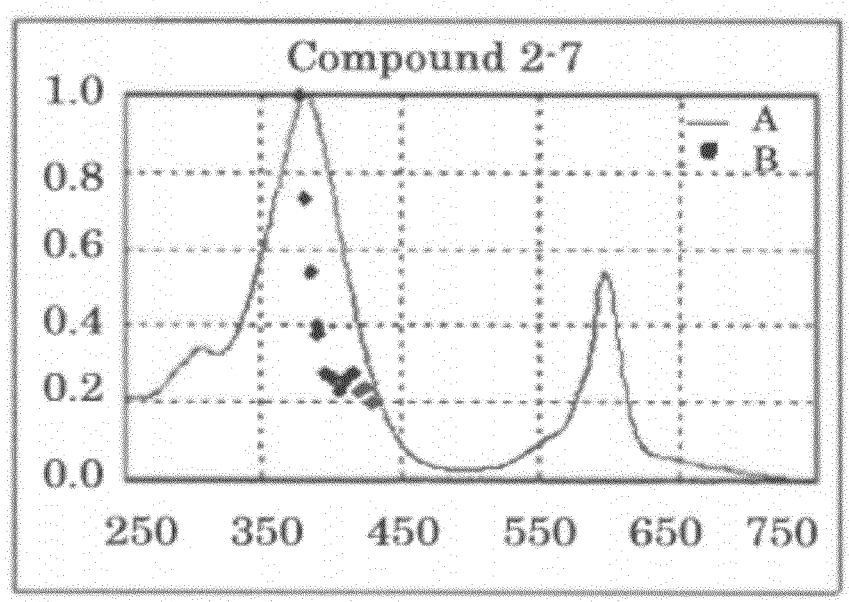
FIG. 11A shows a two-photon absorption spectral chart obtained in Example C-2, wherein the vertical axis corresponds to absorption characteristics, the horizontal axis wavelength (nm); the line indicated by symbol A corresponds to one-photon absorption, and the dots indicated by B two-photon absorption.

Table C8 shows the value of the thus-measured two-photon absorption cross-sectional area, and FIGS. 10B and 11A each show a two-photon absorption spectral chart thereof.

Example C-3

Similarly, Compound 4-6 was measured for its two-photon absorption cross-sectional area.

Figure 11B:
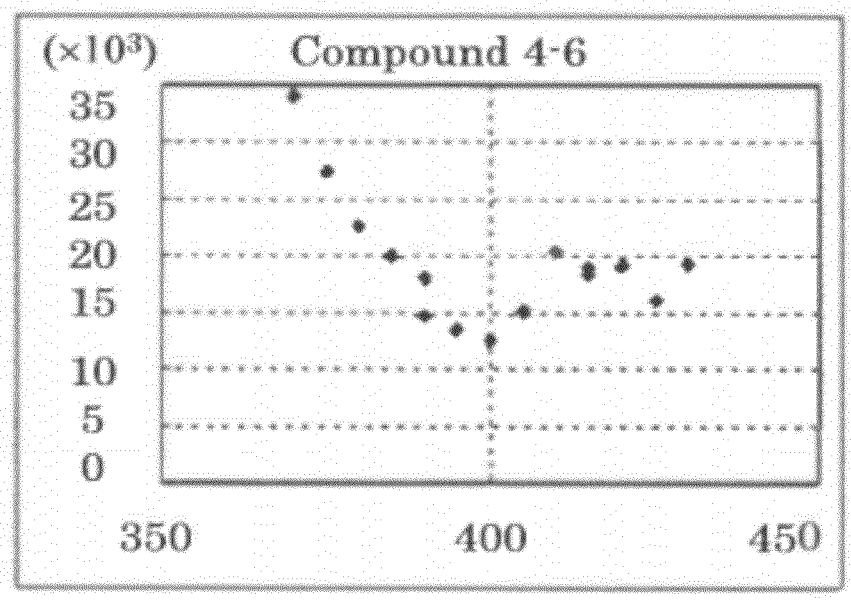
FIG. 11B shows a two-photon absorption spectral chart obtained in Example C-3, wherein two-photon absorption spectra are enlarged, the vertical axis corresponds to two-photon absorption cross-sectional area σ2 (GM), and the horizontal axis wavelength (nm).

Table C8 shows the value of the thus-measured two-photon absorption cross-sectional area, and FIGS. 10A and 11B each show a two-photon absorption spectral chart thereof.

Example C-4

Similarly, Compound 2-6 was measured for its two-photon absorption cross-sectional area. Table C8 shows the value of the thus-measured two-photon absorption cross-sectional area.

Example C-5

Similarly, Compound 3-3 was measured for its two-photon absorption cross-sectional area. Table C8 shows the value of the thus-measured two-photon absorption cross-sectional area.

Example C-6

Similarly, Compound 4-7 was measured for its two-photon absorption cross-sectional area. Table C8 shows the value of the thus-measured two-photon absorption cross-sectional area.

Example C-7

Similarly, Compound 5-6 was measured for its two-photon absorption cross-sectional area. Table C8 shows the value of the thus-measured two-photon absorption cross-sectional area.

Example C-8

Similarly, Compound 6-2 was measured for its two-photon absorption cross-sectional area. Table C8 shows the value of the thus-measured two-photon absorption cross-sectional area.

Example C-9

Similarly, Compound 7-2 was measured for its two-photon absorption cross-sectional area. Table C8 shows the value of the thus-measured two-photon absorption cross-sectional area.

Comparative Example C-1

The following Comparative Compound 1 was dissolved in tetrahydrofuran, and the resultant tetrahydrofuran solution was measured for its two-photon absorption cross-sectional area according to the below-described evaluation method therefor. The result is shown in Table C8.

Comparative Compound 1

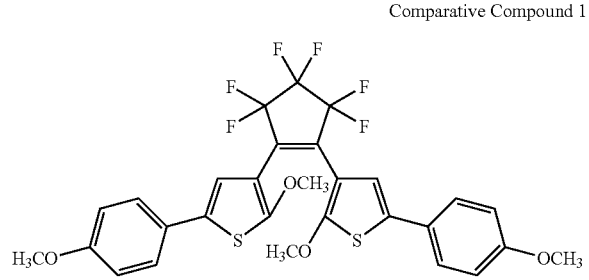

Comparative Example C-2

The following Comparative Compound 2, having a typical porphyrin structure, was dissolved in tetrahydrofuran, and the resultant tetrahydrofuran solution was measured for its two-photon absorption cross-sectional area in a similar manner. The result is shown in Table C8.

Comparative Compound 2

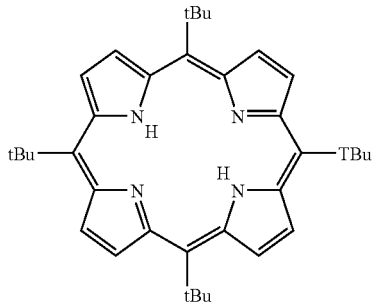

Comparative Example C-3

The following Comparative Compound 3, having a conventional, typical diazaporphyrin structure, was dissolved in tetrahydrofuran, and the resultant tetrahydrofuran solution was measured for its two-photon absorption cross-sectional area. The result is shown in Table C8.

Comparative Compound 3

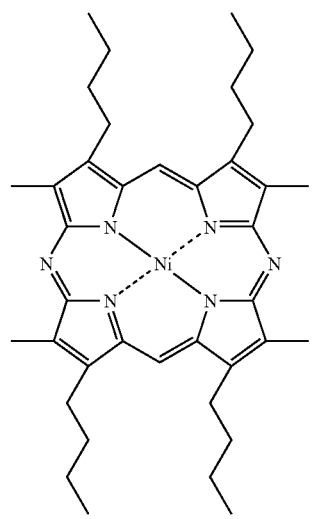

[Method for Measuring Two-Photon Absorption Cross-Sectional Area]

FIG. 8 schematically illustrates a system of the method.

Measuring light source: femtosecond titanium sapphire laser

Wavelength: 720 nm to 920 nm

Pulse width: 100 fs

Repetition frequency: 80 MHz

Light power: 800 mW

Measuring method: Z scan method

Wavelength of light source: 780 nm to 900 nm

Inner diameter of cuvette: 10 mm

Light power for measurement: about 500 mW

Repetition frequency: 80 MHz

Collective lens: f=75 mm

Collection diameter: ~40 μm

A quartz cell filled with each sample solution was placed in a light path through which a focused laser beam was passed. Then, the cell was moved along the light path for Z-scan measurement. The sample solution was measured for its transmittance, and the thus-obtained value and the following theoretical equation (I) were used to determine a nonlinear absorption coefficient of the sample.

$$T = [\ln(1 + I0L0\beta)]/I0L0\beta \quad (I)$$

where T denotes a transmittance (%), I0 denotes an excited light density [GW/cm$^2$], L0 denotes a sample cell length [cm], and β denotes a nonlinear absorption coefficient [cm/GW].

The thus-determined nonlinear absorption coefficient and the following equation (II) were used to calculate a two-photon absorption cross-sectional area σ2. Note that the unit of 2σ is GM (1 GM=1×10$^{-50}$ cm$^4$·s·photon$^{-1}$).

$$\sigma 2 = 1,000 \times h\nu\beta/NAC\beta \quad (II)$$

where h denotes the Planck's constant [J·s], ν denotes a frequency of an incident laser beam [s$^{-1}$], NA denotes the Avogadro's number, and C denotes a concentration of a solution [mol/L].

Evaluation Results

TABLE C8

| Sample | Wavelength (nm) | Two-photon absorption cross-sectional area (GM) |
| --- | --- | --- |
| Ex. C-1 | 830 | 21,000 |
| Ex. C-2 | 840 | 14,000 |
| Ex. C-3 | 830 | 16,000 |
| Ex. C-4 | 840 | 15,500 |
| Ex. C-5 | 830 | 14,500 |
| Ex. C-6 | 840 | 15,000 |
| Ex. C-7 | 840 | 18,000 |
| Ex. C-8 | 850 | 16,500 |
| Ex. C-9 | 840 | 23,000 |
| Comp. Ex. C-1 | 800 | 15 |
| Comp. Ex. C-2 | 780 to 900 | ≈0 |
| Comp. Ex. C-3 | 840 | 2,263 |

Unlike the compound having a typical porphyrin structure, the porphyrin derivatives of the present invention were found to exhibit large two-photon absorption cross-sectional areas.

Also, the porphyrin derivatives of the present invention were found to exhibit a two-photon absorption cross-sectional area 10 times that of the compound having a conventional diazaporphyrin structure.

The compound of the present invention having excellent two-photon absorption properties can provide high-quality, three-dimensional memory materials, light restricting materials, photocurable resins for optical molding (curable materials), materials for photo-chemotherapy, and fluorescent dyes for two-photon fluorescence microscopy.

What is claimed is:

1. A compound represented by the following General Formula (I):

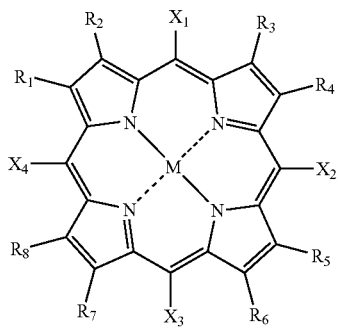

General Formula (1)

where $R_1$ to $R_8$ each represent a hydrogen atom, a halogen atom, a carboxyl group, a carboxylic acid ester group, a substituted or unsubstituted aryl group, or a substituted or unsubstituted alkyl group; wherein at least one of $X_1$ and $X_3$ is a phenyl group having, as a substitutent, an alkyl group, an alkoxy group, a trifluoromethyl group, a nitro group, a cyano group or a carboxylic acid ester group, or a substituted or unsubstituted pyridinyl group, with the proviso that when only one of $X_1$ and $X_3$ is the phenyl group or the pyridinyl group, the other is a hydrogen atom or a halogen atom; and at least one of $X_2$ and $X_4$ is a substituent represented by (a) or (b) given below, with the proviso that when only one of $X_2$ and $X_4$ is the substitutent, the other is a hydrogen atom or a halogen atom,

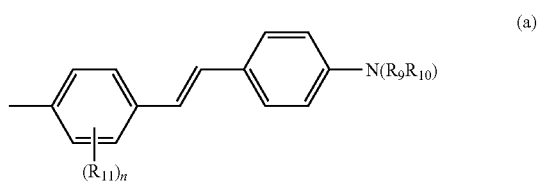

where $R_{11}$ represents an alkyl group or an alkoxy group, $R_9$ and $R_{10}$ each represent a hydrogen atom, an alkyl group or a substituted or unsubstituted phenyl group, and n is an integer of 1 or 2,

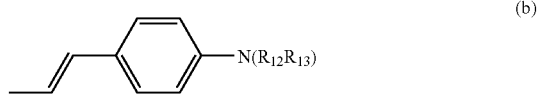

where $R_{12}$ and $R_{13}$ each represent a hydrogen atom, an alkyl group or a substituted or unsubstituted phenyl group; and M represents two hydrogen atoms or a divalent, trivalent or tetravalent metal atom which may have an oxygen atom or a halogen atom.

2. A compound represented by the following General Formula (A):

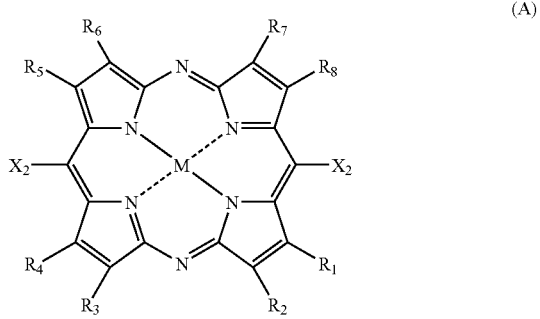

where $R_1$ to $R_8$ each represent a hydrogen atom, a halogen atom, a nitro group, a cyano group, a hydroxyl group, a carboxyl group, a substituted or unsubstituted alkyl group, a substituted or unsubstituted alkoxy group, a substituted or unsubstituted aryl group, a substituted or unsubstituted amino group, or a substituted or unsubstituted acyl group; $X_1$ and $X_2$ each represent a hydrogen atom, a halogen atom, a nitro group, a cyano group, a hydroxyl group, a carboxyl group, a substituted or unsubstituted alkyl group, a substituted or unsubstituted alkoxy group, a substituted or unsubstituted aryl group, a substituted or unsubstituted amino group, a substituted or unsubstituted acyl group, or a group having a substituted or unsubstituted triphenylamine structure which group may be bonded via a linking group to a diazaporphyrin skeleton; at least one of $X_1$ and $X_2$ represents the group having a substituted or unsubstituted triphenylamine structure which group may be bonded via a linking group to a diazaporphyrin skeleton; and M represents two hydrogen atoms, a divalent, trivalent or tetravalent metal atom which may have an oxygen atom or a halogen atom, or a metal atom which may have at least one selected from groups $(OR_9)a$, $(OSiR_{10}R_{11}R_{12})b$, $(OPOR_{13}R_{14})c$ and $(OCOR_{15})d$ (in the groups, $R_9$ to $R_{15}$ each represent a hydrogen atom or a substituted or unsubstituted aliphatic group or aromatic hydrocarbon group, and each of a, b, c and d is an integer of 0 to 2).

3. The compound according to claim 2, wherein the compound is represented by the following formula (1):

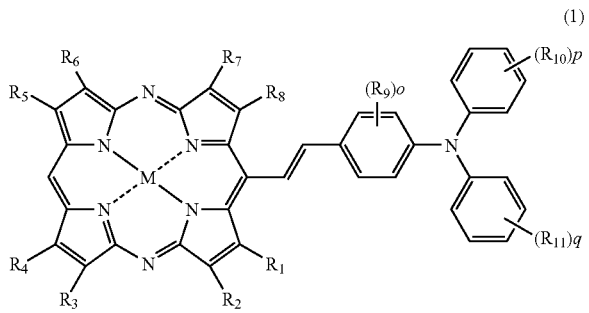

(1)

where $R_1$ to $R_8$ each represent a hydrogen atom, a halogen atom, a nitro group, a cyano group, a hydroxyl group, a carboxyl group, a substituted or unsubstituted alkyl group, a substituted or unsubstituted alkoxy group, a substituted or unsubstituted aryl group, a substituted or unsubstituted amino group, or a substituted or unsubstituted acyl group; $R_9$ to $R_{11}$ each represent a hydrogen atom, a substituted or unsubstituted alkyl group, or a substituted or unsubstituted alkoxy group; o is an integer of 1 to 4; each of p and q is an integer of 1 to 5; and M represents two hydrogen atoms, a divalent, trivalent or tetravalent metal atom which may have an oxygen atom or a halogen atom, or a metal atom which may have at least one selected from groups $(OR_9)$a, $(OSiR_{10}R_{11}R_{12})$b, $(OPOR_{13}R_{14})$c and $(OCOR_{15})$d (in the groups, $R_9$ to $R_{15}$ each represent a hydrogen atom or a substituted or unsubstituted aliphatic group or aromatic hydrocarbon group, and each of a, b, c and d is an integer of 0 to 2).

4. The compound according to claim 2, wherein the compound is represented by the following formula (2):

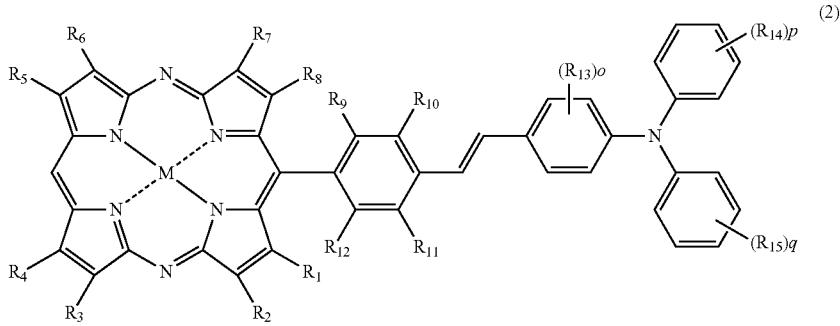

(2)

where $R_1$ to $R_8$ each represent a hydrogen atom, a halogen atom, a nitro group, a cyano group, a hydroxyl group, a carboxyl group, a substituted or unsubstituted alkyl group, a substituted or unsubstituted alkoxy group, a substituted or unsubstituted aryl group, a substituted or unsubstituted amino group, or a substituted or unsubstituted acyl group; $R_9$ to $R_{15}$ each represent a hydrogen atom, a substituted or unsubstituted alkyl group, or a substituted or unsubstituted alkoxy group; o is an integer of 1 to 4; each of p and q is an integer of 1 to 5; and M represents two hydrogen atoms, a divalent, trivalent or tetravalent metal atom which may have an oxygen atom or a halogen atom, or a metal atom which may have at least one selected from groups $(OR_9)$a, $(OSiR_{10}R_{11}R_{12})$b, $(OPOR_{13}R_{14})$c and $(OCOR_{15})$d (in the groups, $R_9$ to $R_{15}$ each represent a hydrogen atom or a substituted or unsubstituted aliphatic group or aromatic hydrocarbon group, and each of a, b, c and d is an integer of 0 to 2).

5. The compound according to claim 2, wherein the compound is represented by the following formula (3):

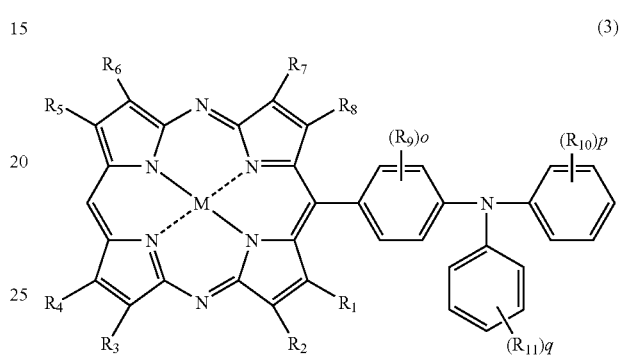

(3)

where $R_1$ to $R_8$ each represent a hydrogen atom, a halogen atom, a nitro group, a cyano group, a hydroxyl group, a carboxyl group, a substituted or unsubstituted alkyl group, a substituted or unsubstituted alkoxy group, a substituted or unsubstituted aryl group, a substituted or unsubstituted amino group, or a substituted or unsubstituted acyl group; $R_9$ to $R_{11}$ each represent a hydrogen atom, a substituted or unsubstituted alkyl group, or a substituted or unsubstituted alkoxy group; o is an integer of 1 to 4; each of p and q is an integer of 1 to 5; and M represents two hydrogen atoms, a divalent, trivalent or tetravalent metal atom which may have an oxygen atom or a halogen atom, or a metal atom which may have at least one selected from groups $(OR_9)$a, $(OSiR_{10}R_{11}R_{12})$b, $(OPOR_{13}R_{14})$c and $(OCOR_{15})$d (in the groups, $R_9$ to $R_{15}$ each represent a hydrogen atom or a substituted or unsubstituted aliphatic group or aromatic hydrocarbon group, and each of a, b, c and d is an integer of 0 to 2).

6. The compound according to claim 2, wherein the compound is represented by the following formula (4):

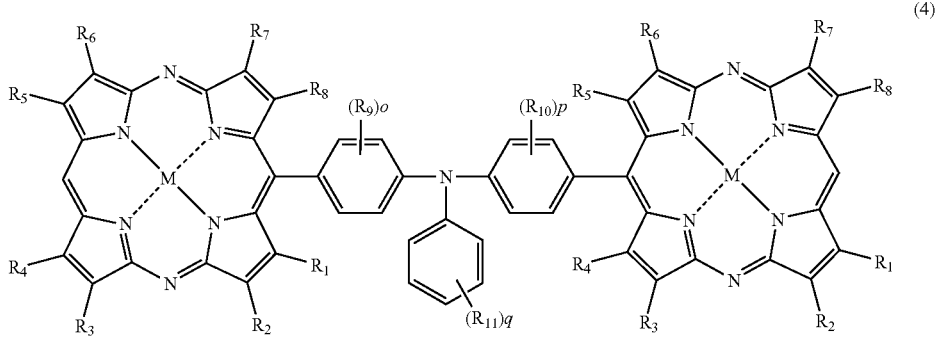

(4)

where $R_1$ to $R_8$ each represent a hydrogen atom, a halogen atom, a nitro group, a cyano group, a hydroxyl group, a carboxyl group, a substituted or unsubstituted alkyl group, a substituted or unsubstituted alkoxy group, a substituted or unsubstituted aryl group, a substituted or unsubstituted amino group, or a substituted or unsubstituted acyl group; $R_9$ to $R_{11}$ each represent a hydrogen atom, a substituted or unsubstituted alkyl group, or a substituted or unsubstituted alkoxy group; o is an integer of 1 to 4; each of p and q is an integer of 1 to 5; and M represents two hydrogen atoms, a divalent, trivalent or tetravalent metal atom which may have an oxygen atom or a halogen atom, or a metal atom which may have at least one selected from groups $(OR_9)a$, $(OSiR_{10}R_{11}R_{12})b$, $(OPOR_{13}R_{14})c$ and $(OCOR_{15})d$ (in the groups, $R_9$ to $R_{15}$ each represent a hydrogen atom or a substituted or unsubstituted aliphatic group or aromatic hydrocarbon group, and each of a, b, c and d is an integer of 0 to 2).

7. The compound according to claim 2, wherein the compound is represented by the following formula (5):

where $R_1$ to $R_8$ each represent a hydrogen atom, a halogen atom, a nitro group, a cyano group, a hydroxyl group, a carboxyl group, a substituted or unsubstituted alkyl group, a substituted or unsubstituted alkoxy group, a substituted or unsubstituted aryl group, a substituted or unsubstituted amino group, or a substituted or unsubstituted acyl group; $R_9$ to $R_{14}$ each represent a hydrogen atom, a substituted or unsubstituted alkyl group, or a substituted or unsubstituted alkoxy group; each of o and r is an integer of 1 to 4; each of p, q, s and t is an integer of 1 to 5; and M represents two hydrogen atoms, a divalent, trivalent or tetravalent metal atom which may have an oxygen atom or a halogen atom, or a metal atom which may have at least one selected from groups $(OR_9)a$, $(OSiR_{10}R_{11}R_{12})b$, $(OPOR_{13}R_{14})c$ and $(OCOR_{15})d$ (in the groups, $R_9$ to $R_{15}$ each represent a hydrogen atom or a substituted or unsubstituted aliphatic group or aromatic hydrocarbon group, and each of a, b, c and d is an integer of 0 to 2).

8. The compound according to claim 2, wherein the compound is represented by the following formula (6):

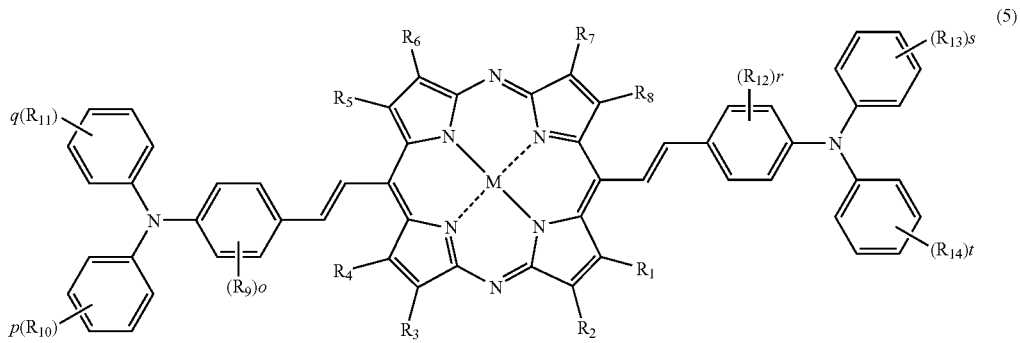

(5)

(6)

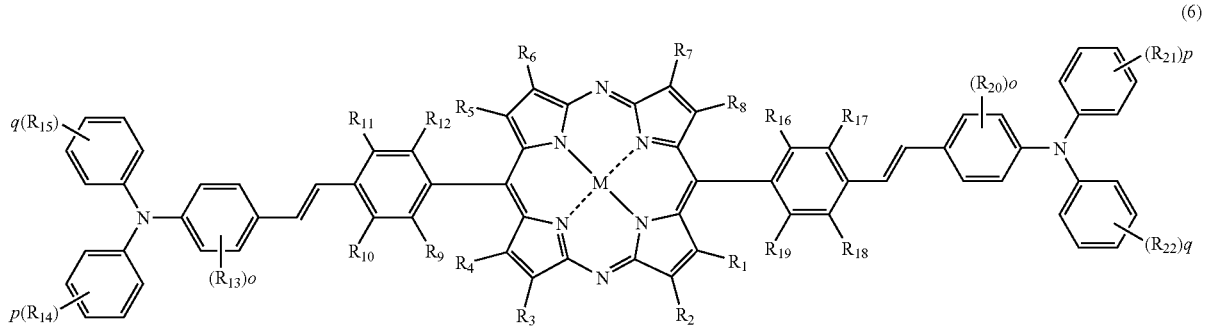

where $R_1$ to $R_8$ each represent a hydrogen atom, a halogen atom, a nitro group, a cyano group, a hydroxyl group, a carboxyl group, a substituted or unsubstituted alkyl group, a substituted or unsubstituted alkoxy group, a substituted or unsubstituted aryl group, a substituted or unsubstituted amino group, or a substituted or unsubstituted acyl group; $R_9$ to $R_{22}$ each represent a hydrogen atom, a substituted or unsubstituted alkyl group, or a substituted or unsubstituted alkoxy group; each of o and r is an integer of 1 to 4; each of p, q, s and t is an integer of 1 to 5; and M represents two hydrogen atoms, a divalent, trivalent or tetravalent metal atom which may have an oxygen atom or a halogen atom, or a metal atom which may have at least one selected from groups $(OR_9)a$, $(OSiR_{10}R_{11}R_{12})b$, $(OPOR_{13}R_{14})c$ and $(OCOR_{15})d$ (in the groups, $R_9$ to $R_{15}$ each represent a hydrogen atom or a substituted or unsubstituted aliphatic group or aromatic hydrocarbon group, and each of a, b, c and d is an integer of 0 to 2).

9. The compound according to claim 2, wherein the compound is represented by the following formula (7):

where $R_1$ to $R_8$ each represent a hydrogen atom, a halogen atom, a nitro group, a cyano group, a hydroxyl group, a carboxyl group, a substituted or unsubstituted alkyl group, a substituted or unsubstituted alkoxy group, a substituted or unsubstituted aryl group, a substituted or unsubstituted amino group, or a substituted or unsubstituted acyl group; $R_9$ to $R_{14}$ each represent a hydrogen atom, a substituted or unsubstituted alkyl group, or a substituted or unsubstituted alkoxy group; each of o and r is an integer of 1 to 4; each of p, q, s and t is an integer of 1 to 5; and M represents two hydrogen atoms, a divalent, trivalent or tetravalent metal atom which may have an oxygen atom or a halogen atom, or a metal atom which may have at least one selected from groups $(OR_9)a$, $(OSiR_{10}R_{11}R_{12})b$, $(OPOR_{13}R_{14})c$ or $(OCOR_{15})d$ (in the groups, $R_9$ to $R_{15}$ each represent a hydrogen atom or a substituted or unsubstituted aliphatic group or aromatic hydrocarbon group, and each of a, b, c and d is an integer of 0 to 2).

10. A compound represented by the following General Formula (III):

(7)

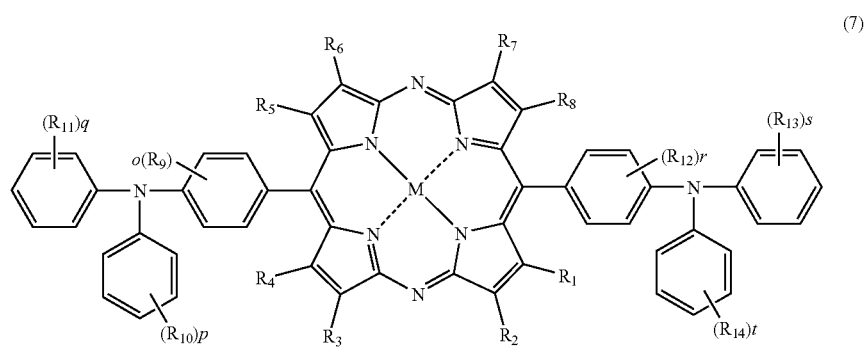

General Formula (III)

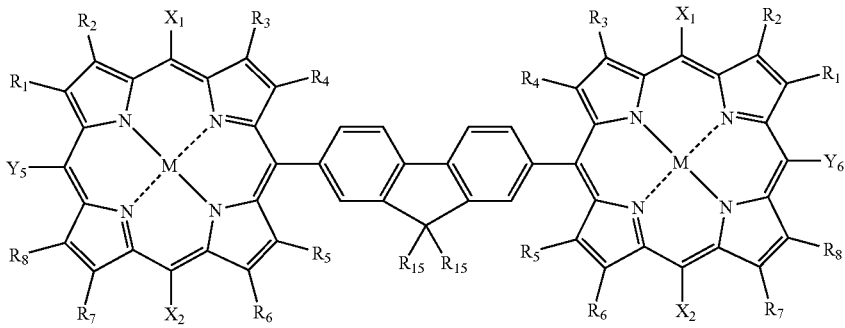

where $R_1$ to $R_8$ each represent a hydrogen atom, a halogen atom, a carboxyl group, a carboxylic acid ester group, a substituted or unsubstituted aryl group, or a substituted or unsubstituted alkyl group; $R_{15}$ represents an alkyl group or a hydrogen atom; at least one of $X_1$ and $X_2$ is a phenyl group having, as a substitutent, an alkyl group, an alkoxy group, a trifluoromethyl group, a nitro group, a cyano group or a carboxylic acid ester group, or a substituted or unsubstituted pyridinyl group, with the proviso that when only one of $X_1$ and $X_2$ is the phenyl group or the pyridinyl group, the other is a hydrogen atom or a halogen atom; $Y_5$ and $Y_6$ each represent a substituent represented by (a) or (b) given below, a hydrogen atom or a halogen atom; and M represents two hydrogen atoms or a divalent, trivalent or tetravalent metal atom which may have an oxygen atom or a halogen atom, (a)

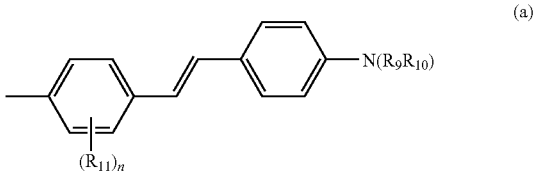

where $R_{11}$ represents an alkyl group or an alkoxy group, $R_9$ and $R_{10}$ each represent a hydrogen atom, an alkyl group or a substituted or unsubstituted phenyl group, and n is an integer of 1 or 2, (b)

where $R_{12}$ and $R_{13}$ each represent a hydrogen atom, an alkyl group or a substituted or unsubstituted phenyl group.

11. The compound according to claim 1, wherein M is a zinc atom.

12. An optical recording material, comprising the compound according to claim 1.

13. An optical molding material, comprising the compound according to claim 1.

14. A light restricting material, comprising the compound according to claim 1.

15. A two-photon excitation fluorescence material, comprising the compound according to claim 1.

16. A three-dimensional optical recording medium, comprising the compound according to claim 1.

* * * * *